US011299543B2

(12) United States Patent
Farsaci et al.

(10) Patent No.: US 11,299,543 B2
(45) Date of Patent: Apr. 12, 2022

(54) USE OF AN ANTI-PD-1 ANTIBODY IN COMBINATION WITH AN ANTI-CD30 ANTIBODY IN CANCER TREATMENT

(71) Applicants: Bristol-Myers Squibb Company, Princeton, NJ (US); Seattle Genetics, Inc., Bothell, WA (US)

(72) Inventors: Benedetto Farsaci, Princeton, NJ (US); Neil Josephson, Bothell, WA (US); Anthony Cao, Sammamish, WA (US); Ryan Heiser, Lake Stevens, WA (US)

(73) Assignees: Bristol-Myers Squibb Company, Princeton, NJ (US); Seattle Genetics. Tnc., Bothell, WA (US)

( * ) Notice: Subject to any disclaimer, the term of this patent is extended or adjusted under 35 U.S.C. 154(b) by 346 days.

(21) Appl. No.: 16/306,282

(22) PCT Filed: Jun. 1, 2017

(86) PCT No.: PCT/US2017/035521
§ 371 (c)(1),
(2) Date: Nov. 30, 2018

(87) PCT Pub. No.: WO2017/210473
PCT Pub. Date: Dec. 7, 2017

(65) Prior Publication Data
US 2019/0218293 A1    Jul. 18, 2019

Related U.S. Application Data

(60) Provisional application No. 62/344,866, filed on Jun. 2, 2016, provisional application No. 62/382,839, filed on Sep. 2, 2016.

(51) Int. Cl.
C07K 16/28 (2006.01)
A61P 35/00 (2006.01)
A61K 39/395 (2006.01)
A61K 39/00 (2006.01)

(52) U.S. Cl.
CPC .......... *C07K 16/2818* (2013.01); *A61P 35/00* (2018.01); *C07K 16/2878* (2013.01); *A61K 2039/505* (2013.01); *A61K 2039/507* (2013.01); *C07K 2317/76* (2013.01)

(58) Field of Classification Search
CPC ................... C07K 16/2878; C07K 2317/76
See application file for complete search history.

(56) References Cited

U.S. PATENT DOCUMENTS

| | | | |
|---|---|---|---|
| 6,808,710 B1 | 10/2004 | Wood et al. | |
| 7,488,802 B2 | 2/2009 | Collins et al. | |
| 7,595,048 B2 | 9/2009 | Honjo et al. | |
| 7,943,743 B2 | 5/2011 | Korman et al. | |
| 8,008,449 B2 | 8/2011 | Korman et al. | |
| 8,168,179 B2 | 5/2012 | Honjo et al. | |
| 8,168,757 B2 | 5/2012 | Finnefrock et al. | |
| 8,217,149 B2 | 7/2012 | Irving et al. | |
| 8,354,509 B2 | 1/2013 | Carven et al. | |
| 8,609,089 B2 | 12/2013 | Langermann et al. | |
| 8,728,474 B2 | 5/2014 | Honjo et al. | |
| 8,779,105 B2 | 7/2014 | Korman et al. | |
| 8,779,108 B2 | 7/2014 | Queva et al. | |
| 8,900,587 B2 | 12/2014 | Carven et al. | |
| 9,067,999 B1 | 6/2015 | Honjo et al. | |
| 9,073,994 B2 | 7/2015 | Honjo et al. | |
| 9,084,776 B2 | 7/2015 | Korman et al. | |
| 9,212,224 B2 | 12/2015 | Cogswell et al. | |
| 9,358,289 B2 | 6/2016 | Korman et al. | |
| 9,387,247 B2 | 7/2016 | Korman et al. | |
| 9,393,301 B2 | 7/2016 | Honjo et al. | |
| 9,402,899 B2 | 8/2016 | Honjo et al. | |
| 9,439,962 B2 | 9/2016 | Honjo et al. | |
| 9,492,539 B2 | 11/2016 | Korman et al. | |
| 9,492,540 B2 | 11/2016 | Korman et al. | |
| 9,856,320 B2 | 1/2018 | Cogswell et al. | |
| 10,072,082 B2 | 9/2018 | Cogswell et al. | |
| 10,138,299 B2 | 11/2018 | Cogswell et al. | |
| 10,266,594 B1 | 4/2019 | Cogswell et al. | |
| 10,266,595 B2 | 4/2019 | Cogswell et al. | |
| 10,266,596 B1 | 4/2019 | Cogswell et al. | |
| 10,308,714 B2 | 6/2019 | Cogswell et al. | |
| 10,316,090 B2 | 6/2019 | Cogswell et al. | |
| 10,316,091 B2 | 6/2019 | Cogswell et al. | |

(Continued)

FOREIGN PATENT DOCUMENTS

WO    WO-2004004771 A1    1/2004
WO    WO-2006121168 A1    11/2006
(Continued)

OTHER PUBLICATIONS

Clinical Trial No. NCT02572167, version 1, posted on Oct. 7, 2015.*
Padlan, Advances in Protein Chemistry, 1996, 49:57-133.*
Berglund etal, Protein Science, 2008, 17:606-613.*
Tzartos et al., Methods in Molecular Biology, 1996, 66:55-66.*
Clinical Trial NCT01896999 (v127), posted on Aug. 26, 2015.*
Clinical Trial NCT02572167 (v1), posted on Oct. 7, 2015.*
Adcetris® (brentuximab vedotin) package insert. Seattle Genetics: Bothell, WA; Mar. 2016, 26 pages.

(Continued)

*Primary Examiner* — Hong Sang
(74) *Attorney, Agent, or Firm* — Sterne, Kessler, Goldstein & Fox P.L.L.C.

(57) ABSTRACT

This disclosure provides methods for treating a tumor in a subject comprising administering to the subject an anti-PD-1 antibody and an anti-CD30 antibody. In some embodiments, the tumor is derived from a lymphoma (e.g., a Hodgkin lymphoma or a non-Hodgkin lymphoma). In certain embodiments, the anti-CD30 antibody is an antibody-drug conjugate, e.g., brentuximab vedotin.

10 Claims, 17 Drawing Sheets

(56) References Cited

U.S. PATENT DOCUMENTS

| | | | |
|---|---|---|---|
| 10,323,092 | B2 | 6/2019 | Cogswell et al. |
| 10,323,093 | B2 | 6/2019 | Cogswell et al. |
| 10,344,090 | B2 | 7/2019 | Yuan et al. |
| 10,441,655 | B2 | 10/2019 | Korman et al. |
| 2006/0110383 | A1 | 5/2006 | Honjo et al. |
| 2009/0217401 | A1 | 8/2009 | Korman et al. |
| 2009/0297518 | A1 | 12/2009 | Honjo et al. |
| 2011/0081341 | A1 | 4/2011 | Honjo et al. |
| 2013/0017199 | A1 | 1/2013 | Langermann et al. |
| 2013/0133091 | A1 | 5/2013 | Korman et al. |
| 2013/0309250 | A1 | 11/2013 | Cogswell et al. |
| 2014/0212422 | A1 | 7/2014 | Korman et al. |
| 2014/0294852 | A1 | 10/2014 | Korman et al. |
| 2014/0314714 | A1 | 10/2014 | Honjo et al. |
| 2014/0328833 | A1 | 11/2014 | Korman et al. |
| 2014/0341917 | A1 | 11/2014 | Nastri et al. |
| 2014/0348743 | A1 | 11/2014 | Korman et al. |
| 2014/0356353 | A1 | 12/2014 | Queva et al. |
| 2015/0079109 | A1 | 3/2015 | Li et al. |
| 2015/0093380 | A1 | 4/2015 | Honjo et al. |
| 2015/0125463 | A1* | 5/2015 | Cogswell ............ A61P 35/04 424/142.1 |
| 2015/0165025 | A1 | 6/2015 | Korman et al. |
| 2015/0197572 | A1 | 7/2015 | Honjo et al. |
| 2016/0090417 | A1 | 3/2016 | Cogswell et al. |
| 2016/0158355 | A1 | 6/2016 | Honjo et al. |
| 2016/0158356 | A1 | 6/2016 | Honjo et al. |
| 2017/0051060 | A1 | 2/2017 | Honjo et al. |
| 2017/0088615 | A1 | 3/2017 | Korman et al. |
| 2018/0273624 | A1 | 9/2018 | Cogswell et al. |
| 2018/0282413 | A1 | 10/2018 | Cogswell et al. |
| 2018/0282414 | A1 | 10/2018 | Cogswell et al. |
| 2018/0312590 | A1 | 11/2018 | Cogswell et al. |
| 2018/0319887 | A1 | 11/2018 | Cogswell et al. |
| 2019/0092863 | A1 | 3/2019 | Cogswell et al. |
| 2019/0100589 | A1 | 4/2019 | Cogswell et al. |
| 2019/0100590 | A1 | 4/2019 | Cogswell et al. |
| 2019/0112376 | A1 | 4/2019 | Cogswell et al. |
| 2019/0112377 | A1 | 4/2019 | Cogswell et al. |
| 2019/0135920 | A1 | 5/2019 | Cogswell et al. |
| 2019/0153099 | A1 | 5/2019 | Cogswell et al. |
| 2019/0290757 | A1 | 9/2019 | Farsaci et al. |

FOREIGN PATENT DOCUMENTS

| | | | | |
|---|---|---|---|---|
| WO | WO-2012145493 | A1 | 10/2012 | |
| WO | WO-2013173223 | A1 | 11/2013 | |
| WO | WO-2014179664 | A2 | 11/2014 | |
| WO | WO-2014194302 | A2 | 12/2014 | |
| WO | WO-2015069703 | A1 * | 5/2015 | ......... C07K 16/2878 |
| WO | WO-2015085847 | A1 | 6/2015 | |
| WO | WO-2015112800 | A1 | 7/2015 | |
| WO | WO-2015112900 | A1 | 7/2015 | |
| WO | WO-2016149201 | A2 | 9/2016 | |
| WO | WO-2017210473 | A1 | 12/2017 | |

OTHER PUBLICATIONS

Ansell, S.M., et al., "PD-1 Blockade with Nivolumab in Relapsed or Refractory Hodgkin's Lymphoma," The New England Journal of Medicine 372(4):311-319, Massachusetts Medical Society, United States (Jan. 22, 2015).

Brahmer., J.R., et al., "Phase I Study of Single-agent Anti-programmed Death-1 (MDX-1106) in Refractory Solid Tumors: Safety, Clinical Activity, Pharmacodynamics, and Immunologic Correlates," Journal of Clinical Oncology 28(19):3167-3175, American Society of Clinical Oncology, United States (Jul. 2010).

Brahmer, J., et al., "Nivolumab versus Docetaxel in Advanced Squamous-Cell Non-Small-Cell Lung Cancer," New England Journal of Medicine 373:123-135, Massachusetts Medical Society, United States (Jul. 9, 2015).

Brody, J., et al., "Active and passive immunotherapy for lymphoma: proving principles and improving results," Journal of Clinical Oncology 29(14):1864-1875, American Society of Clinical Oncology, United States (2011).

Chen, B.J., et al., "PD-L1 Expression Is Characteristic of a Subset of Aggressive B-cell Lymphomas and Virus-associated Malignancies," Clinical Cancer Research 19(13):3462-3473, The Association, United States (Jul. 2013).

Cheson, B.D., et al., "Recommendations for Initial Evaluation, Staging, and Response Assessment of Hodgkin and Non-hodgkin Lymphoma: The Lugano Classification," Journal of Clinical Oncology 32(27):3059-3068, American Society of Clinical Oncology, United States (Sep. 2014).

ClinicalTrials, "A Study of Brentuximab Vedotin Combined With Nivolumab for Relapsed or Refractory Hodgkin Lymphoma," NCT02572167, accessed at https://clinicaltrials.gov/ct2/show/NCT02572167, accessed on Mar. 14, 2018.

ClinicalTrials, "An Investigational Immuno-therapy Safety and Effectiveness Study of Nivolumab in Combination With Brentuximab Vedotin to Treat Non-Hodgkin Lymphomas (CheckMate 436)," NCT02581631, accessed at https://clinicaltrials.gov/ct2/show/NCT02581631, accessed on Jun. 19, 2018.

Condeelis, J. and Weissleder, R., "In Vivo Imaging in Cancer," Cold Spring Harbor Perspectives in Biology 2(12):a003848, Cold Spring Harbor Laboratory Press, United States (Dec. 2010).

Drake, "Safety, Durable Clinical Benefit, and Remission Resulting from Nivolumanb (Anti-PD-1; BMS-936558; ONO-4538) in a Phase 1 Trial In Patients With Previously Treated Metastatic Renal Cell Carcinoma (mRCC); Long-Term Patient Follow-Up, Abstracts of the 12th International Kidney Cancer Symposium. Oct. 25-26, 2013. Chicago, Illinois, USA," BJU International 112 (Suppl 3):1-17, Blackwell Science, England (Nov. 2013).

Dunleavy, K. and Wilson, W.H., "Primary Mediastinal B-cell Lymphoma and Mediastinal Gray Zone Lymphoma: Do They Require a Unique Therapeutic Approach?," Blood 125(1):33-39, American Society of Hematology, United States (Jan. 2015).

Duvic, M., et al., "Results of a Phase II Trial of Brentuximab Vedotin forCD30+ Cutaneous T-Cell Lymphoma and Lymphomatoid Papulosis," J. Clin. Oncology 33(32):3759-3765, American Society of Clinical Oncology, United States (Nov. 10, 2015).

Francisco, J.A., et al., "Cac10-vcmmae, an Anti-cd30-monomethyl Auristatin E Conjugate with Potent and Selective Antitumor Activity," Blood 102(4):1458-1465, American Society of Hematology, United States (2003).

Gardai, S.J., et al., Abstract 2469: Brentuximab Vedotin-mediated Immunogenic Cell Death, In: Proceedings of the 106th Annual Meeting of the American Association for Cancer Research, vol. 75(15 Suppl), Abstract 2469, Apr. 2015.

Genbank, "Homo sapiens TNF receptor superfamily member 8 (TNFRSF8), transcript variant 1, mRNA," accession No. NM_001243.4, accessed at https://www.ncbi.nlm.nih.gov/nuccore/NM_001243.4, Jun. 30, 2018.

GenBank, "Human hPD-1 (hPD-1) mRNA, complete cds," Accession No. U64863.1, accessed on https://www.ncbi.nlm.nih.gov/nuccore/U64863, Oct. 12, 2005.

GenBank, "RecName: Full=Programmed cell death 1 ligand 1; Short=PD-L1; Short=PDCD1 ligand 1; Short=Programmed death ligand 1; AltName: Full=B7 homolog 1; Short=B7-H1; AltName: CD_antigen=CD274; Flags: Precursor," Accession No. Q9NZQ7.1, accessed on https://www.ncbi.nlm.nih.gov/protein/Q9NZQ7, Nov. 2, 2016.

Hamid, O. and Carvajal, R.D., "Anti-programmed Death-1 and Anti-programmed Death-ligand 1 Antibodies in Cancer Therapy," Expert Opinion on Biological Therapy 13(6):847-861, Taylor & Francis, England (Jun. 2013).

Hamid, O., et al., "Safety and Tumor Responses with Lambrolizumab (Anti-Pd-1) in Melanoma," The New England Journal of Medicine 369(2):134-144, Massachusetts Medical Society, United States of America (Jul. 2013).

Han, X., et al., "Lymphoma Survival Patterns by Who Subtype in the United States, 1973-2003," Cancer Causes & Control 19(8):841-858, Kluwer Academic Publishers, Netherlands (Oct. 2008).

Herbst, R.S., et al., "A Study of MPDL3280A, an Engineered PD-L1 Antibody in Patients with Locally Advanced or Metastatic

(56) References Cited

OTHER PUBLICATIONS

Tumors," Journal of Clinical Oncology 31(Suppl):Abstract 3000, American Society of Clinical Oncology, United States (2013).
Hodi, F.S., et al., "Improved Survival with Ipilimumab in Patients with Metastatic Melanoma," The New England Journal of Medicine 363(8):711-723, Massachusetts Medical Society, United States (Aug. 2010).
Horwitz, S.M., et al., "Objective responses in relapsed T-cell lymphomas with single-agent brentuximab vedotin," Blood 123(20):3095-3100, American Society of Hematology, United States (2014).
Howlader, N., et al., "SEER Cancer Statistics Review, 1975-2014," National Cancer Institute, Bethesda, accessed at https://seer.cancer.gov/csr/1975_2014/, accessed on Nov. 2016.
International Search Report and Written Opinion for International Application No. PCT/US2017/035521, dated Aug. 4, 2017, 10 pages.
Jacobsen, E.D., et al., "Brentuximab vedotin demonstrates objective responses in a phase 2 study of relapsed/refractory DLBCL with variable CD30 expression," Blood 125(9): 1394-1402, American Society of Hematology, United States (Feb. 26, 2015).
Johnson, D.B., et al., "Severe Cutaneous and Neurologic Toxicity in Melanoma Patients during Vemurafenib Administration Following Anti-PD-1 Therapy," Cancer Immunology Research 1(6):373-377, American Association for Cancer Research, United States (Dec. 2013).
Jourdain, A., et al., "Outcome of and prognostic factors for relapse in children and adolescents with mature B-cell lymphoma and leukemia treated in three consecutive prospective "Lymphomes Malins B" protocols. A Société Franaise des Cancers de l'Enfant study," Haematologica 100(6):810-817, Ferrata Storti Foundation, Italy (Jun. 2015).
Khleif, S., et al., "MEDI4736, An Anti-PD-L1 Antibody with Modified Fc Domain: Preclinical Evaluation and Early Clinical Results from a Phase 1 Study in Patients with Advanced Solid Tumors," Abstract 802, in Proceedings from the European Cancer Congress 2013, Amsterdam, The Netherlands (Sep. 27-Oct. 1, 2013).
Lesokhin, A.M., et al., "Nivolumab in Patients With Relapsed or Refractory Hematologic Malignancy: Preliminary Results of a Phase Ib Study," J. Clinical Oncology 34(23):2698-2704, American Society of Clinical Oncology, United States (Aug. 10, 2016).
Li, F., et al., "Intracellular Released Payload Influences Potency and Bystander-Killing Effects of Antibody-Drug Conjugates in Preclinical Models," Cancer Research 76(9):2710-2719, American Association for Cancer Research, United States (May 2016).
Maly, J. and Alinari, L., "Pembrolizumab in Classical Hodgkin's Lymphoma," European Journal of Haematology 97(3):219-227, Blackwell, England (Sep. 2016).
McCabe, K.E. and Wu, A.M., "Positive Progress in ImmunoPET—not Just a Coincidence," Cancer Biotherapy & Radiopharmaceuticals 25(3):253-261, Mary Ann Liebert, Inc, United States (Jun. 2010).
McDermott, D.F., and Atkins, M.B., "PD-1 as a Potential Target in Cancer Therapy," Cancer Medicine 2(5):662-673, John Wiley & Sons Ltd., United States (Oct. 2013).
Morton, L.M., et al., "Lymphoma Incidence Patterns by Who Subtype in the United States, 1992-2001," Blood 107(1):265-276, American Society of Hematology, United States (Jan. 2006).
Motzer, R. J., et al., "Nivolumab versus Everolimus in Advanced Renal-Cell Carcinoma," the New England Journal of Medicine 373:1803-1813, Massachusetts Medical Society, United States (Nov. 2015).
NCCN Guidelines® (2014), available at http://www.nccn.org/professionals/physician_gls/f_guidelines.asp, last accessed May 14, 2014, 4 pages.
NCI Drug Dictionary, anti-PD-1 Fusion Protein AMP-224, accessed on Dec. 1, 2016, retrieved from the Internet URL: https://www.cancer.gov/publications/dictionaries/cancer-drug?cdrid=700595.

NCI Drug Dictionary, anti-PD-1 monoclonal antibody MEDI0680, accessed on Dec. 1, 2016, retrieved from the Internet URL: https://www.cancer.gov/publications/dictionaries/cancer-drug?cdrid=756047.
NCI Drug Dictionary, pembrolizumab, accessed on Dec. 1, 2016, retrieved from the Internet URL: https://www.cancer.gov/drugdictionary?cancer-drug?cdrid=695789, 3 pages.
Oflazoglu, E., et al., "Macrophages Contribute to the Antitumor Activity of the Anti-CD30 Antibody SGN-30," Blood 110(13):4370-4372, American Society of Hematology, United States (Dec. 2007).
Olafsen, T., et al., "ImmunoPET Imaging of B-Cell Lymphoma Using 124I-Anti-CD20 scFv Dimers (Diabodies)," Protein Engineering, Design & Selection 23(4):243-249, Oxford University Press, England (Apr. 2010).
OPDIVO® (nivolumab) package insert. Bristol-Myers Squibb: Princeton, NJ; Jan. 2016, 62 pages.
Pro, B., et al., "Brentuximab vedotin (SGN-35) in patients with relapsed or refractory systemic anaplastic large-cell lymphoma: results of a phase II study," J. Clinical Oncology 30(18):2190-2196, American Society of Clinical Oncology, United States (2012).
Rini, B.I., et al., "Phase 1 Dose-escalation Trial of Tremelimumab Plus Sunitinib in Patients with Metastatic Renal Cell Carcinoma," Cancer 117(14):758-767, Wiley, United States (Feb. 2011).
Schreiber, R.D., et al., "Cancer immunoediting: integrating immunity's roles in cancer suppression and promotion," Science 331 (6024):1565-1570, American Association for the Advancement of Science, United States (2011).
Sjoblom, T., et al., "The Consensus Coding Sequences of Human Breast and Colorectal Cancers," Science 314(5797):268-274, American Association for the Advancement of Science, United States (Oct. 2006).
Taube, J.M., et al., "Colocalization of Inflammatory Response with B7-H1 Expression in Human Melanocytic Lesions Supports an Adaptive Resistance Mechanism of Immune Escape," Science Translational Medicine 4(127):127ra37, American Association for the Advancement of Science, United States (Mar. 2012).
Topalian, S.L., et al., "Safety, Activity and Immune Correlates of Anti-PD-1 Antibody in Cancer," The New England Journal of Medicine 366(26):2443-2454, Massachusetts Medical Society, United States (Jun. 2012).
Topalian, S.L., et al., "Survival, Durable Tumor Remission, and Long-term Safety in Patients with Advanced Melanoma Receiving Nivolumab," Journal of Clinical Oncology 32(10):1020-1030, American Society of Clinical Oncology, United States (Apr. 2014).
Topalian, S.L., et al., "Targeting the PD-1/B7-H1(PD-L1) Pathway to Activate Anti-tumor Immunity," Current Opinion in Immunology 24(2):207-212, Elsevier, England (Apr. 2012).
United States Adopted Name (USAN) Drug Finder, Pembrolizumab: Statement on a nonproprietary name adopted by the USAN Council (ZZ-165), published Nov. 27, 2013, accessed at https://searchusan.ama-amaassn.org/usan/documentDownload?uri=%2Funstructured%2Fbina[Y%2Fusan%2Fpembroli zab.pdf, accessed on Dec. 8, 2016, 2 pages.
Wang, C., et al., "In Vitro Characterization of the Anti-PD-1 Antibody Nivolumab, BMS-936558, and in Vivo Toxicology in Non-human Primates," Cancer Immunology Research 2(9):846-856, American Association for Cancer Research, United States (Sep. 2014).
Weber, J.S., et al., "Nivolumab versus chemotherapy in patients with advanced melanoma who progressed after anti-CTLA-4 treatment (CheckMate 037): a randomised, controlled, openlabel, phase 3 trial," Lancet Oncol 16(4):375-384, Elsevier, Netherlands (Apr. 2015).
Younes, A., et al., "Results of a pivotal phase II study of brentuximab vedotin for patients with relapsed or refractory Hodgkin's lymphoma," J. Clinical Oncology 30(18):2183-2189, American Society of Clinical Oncology, United States (2012).
Armand, P., et al., "Nivolumab in patients with relapsed or refractory lymphoid malignancies and classical Hodgkin lymphoma: updated safety and efficacy results of a phase 1 study," Haematologica (Suppl 1):S808 (abstract) (Jun. 22, 2015).

(56) References Cited

OTHER PUBLICATIONS

Foyil, K. V., and Bartlett, N. L., "Anti-CD30 Antibodies for Hodgkin Lymphoma," *Current Hematologic Malignancy Reports* 5:140-147, Springer Science + Business Media, United States (May 6, 2010).

History of Changes for Study: NCT01896999, "Ipilimumab, Nivolumab, and Brentuximab Vedotin in Treating Patients With Relapse or Refractory Hodgkin Lymphoma," retrieved from https://clinicaltrials.gov/ct2/history/NCT018969997V_198=View#StudyPagetop, dated Aug. 23, 2021, 25 pages.

History of Changes for Study: NCT02581631, "A Safety and Effectiveness Study of Nivolumab in Combination with Brentuximab Vedotin To Treat Non-Hodgkin Lymphoma: 436," retrieved from https://clinicaltrials.gov/ct2/history/NCT025816317V_16=View#StudyPagetop, dated Aug. 23, 2021, 4 pages.

History of Changes for Study: NCT02572167, "A Study of Brentuximab Vedotin Combined With Nivolumab for Relapsed or Refractory Hodgkin Lymphoma," retrieved from https://clinicaltrials.gov/ct2/history/NCT025721677V_8=View#StudyPagetop, dated Aug. 23, 2021, 4 pages.

Japanese Office Action dated Jun. 22, 2021, in Japanese Patent Application No. 2018-563009, 16 pages.

Yoshida, T., et al., "Pharmacological profile and clinical efficacy of human anti-human PD-1 antibody nivolumab (OPDIVO®) as a new immune checkpoint inhibitor," Nihon Yahurigaku Zasshi 146(2):106-14, J-Stage, Japan (Aug. 2015).

\* cited by examiner

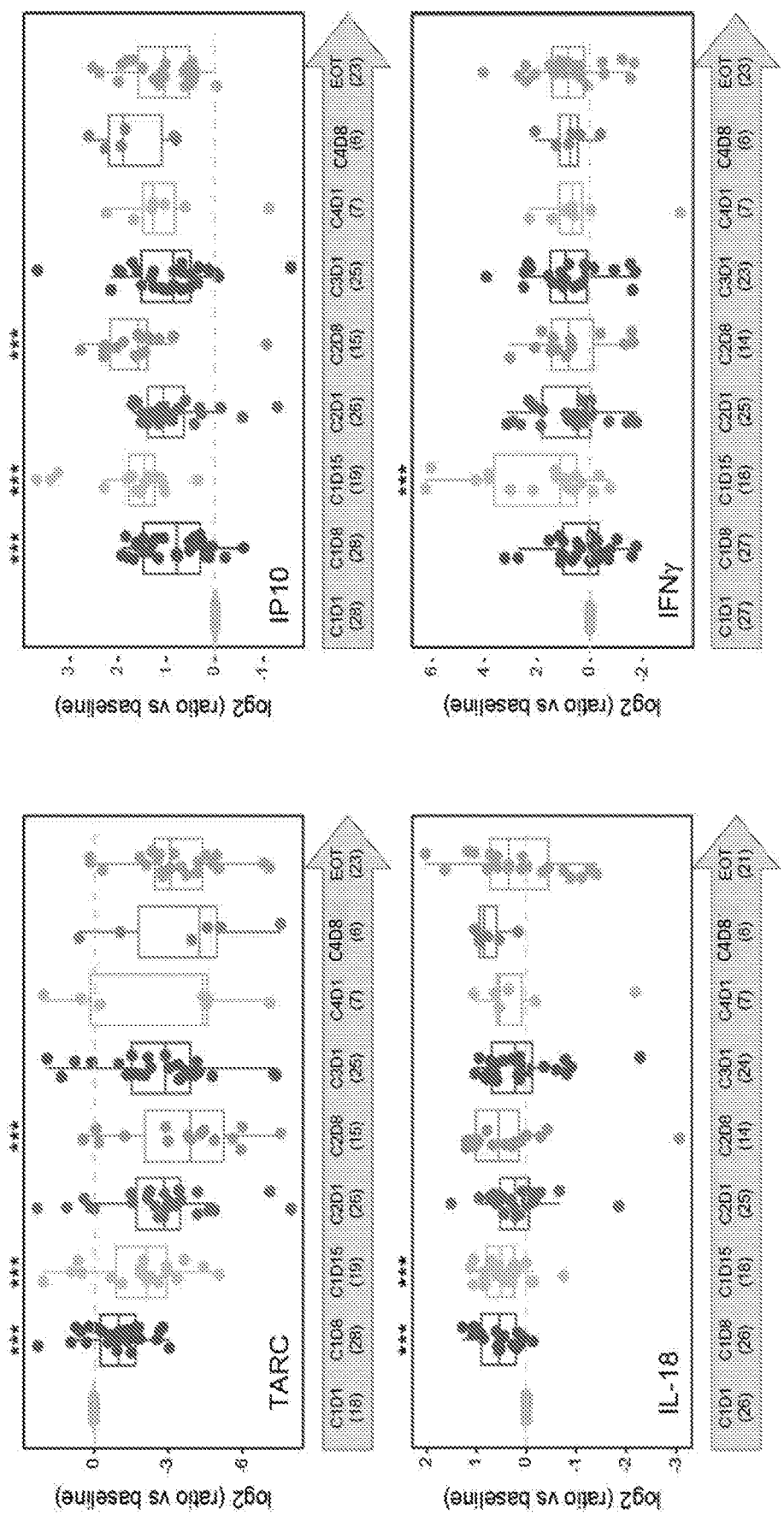

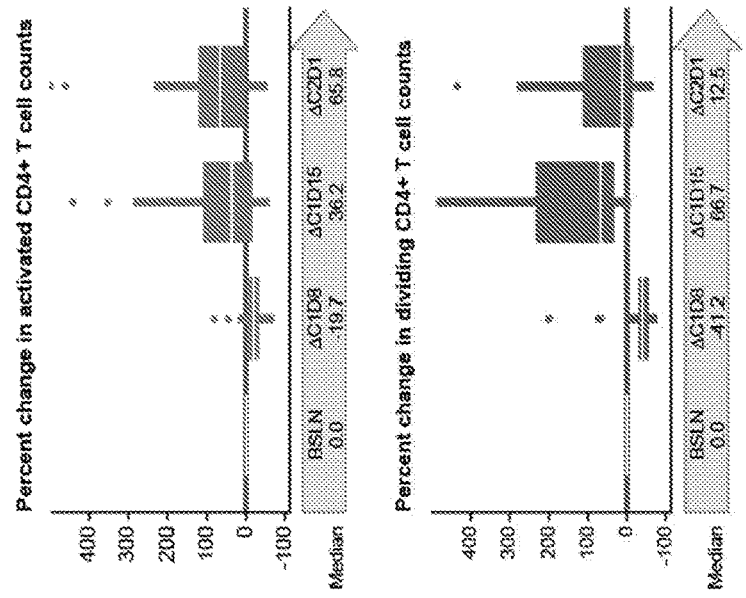
FIG. 7B
FIG. 7C
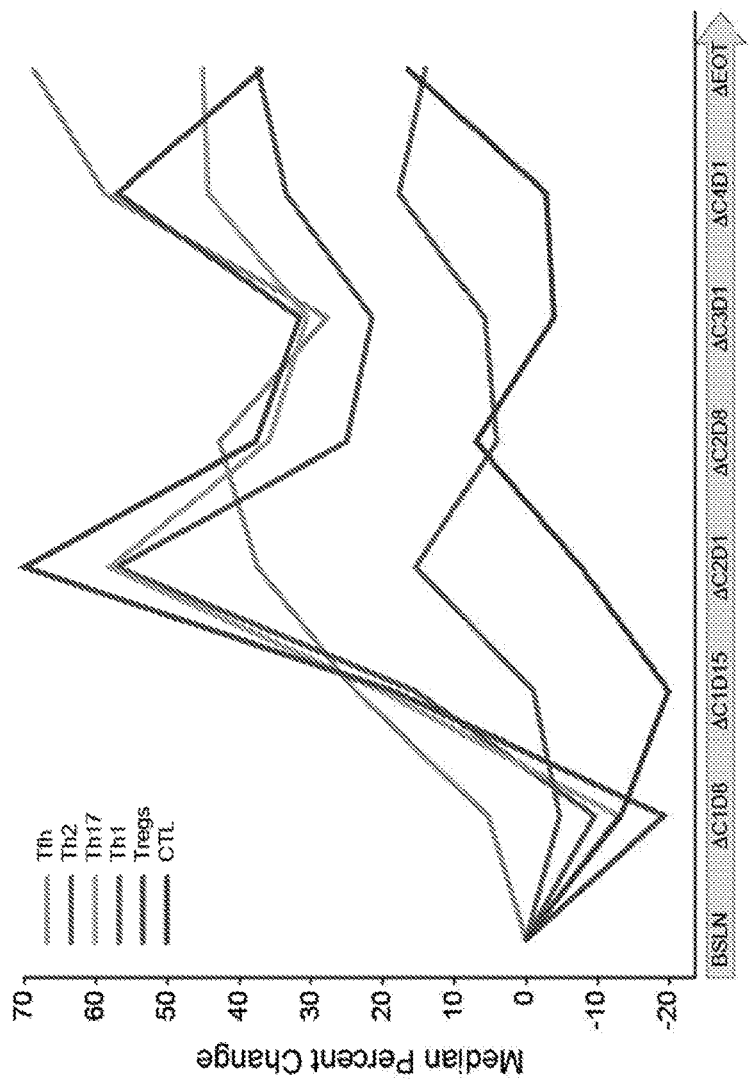
FIG. 7A

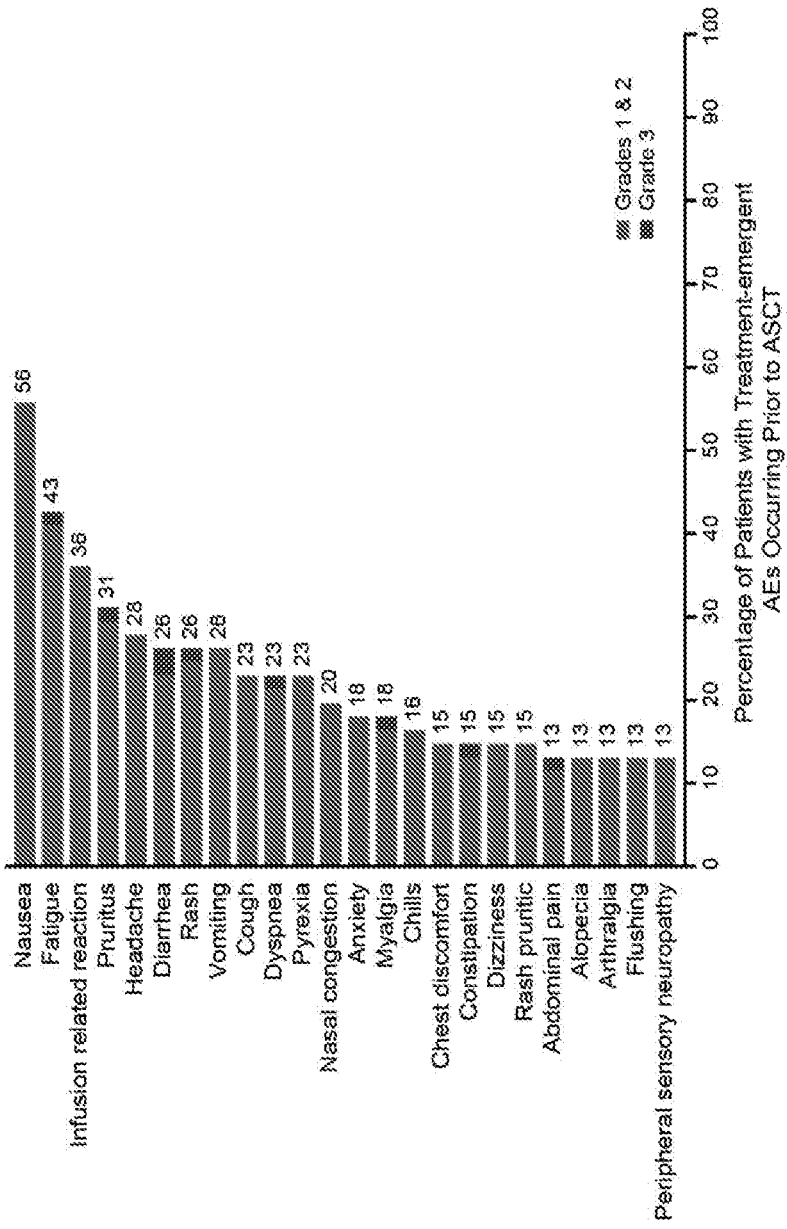

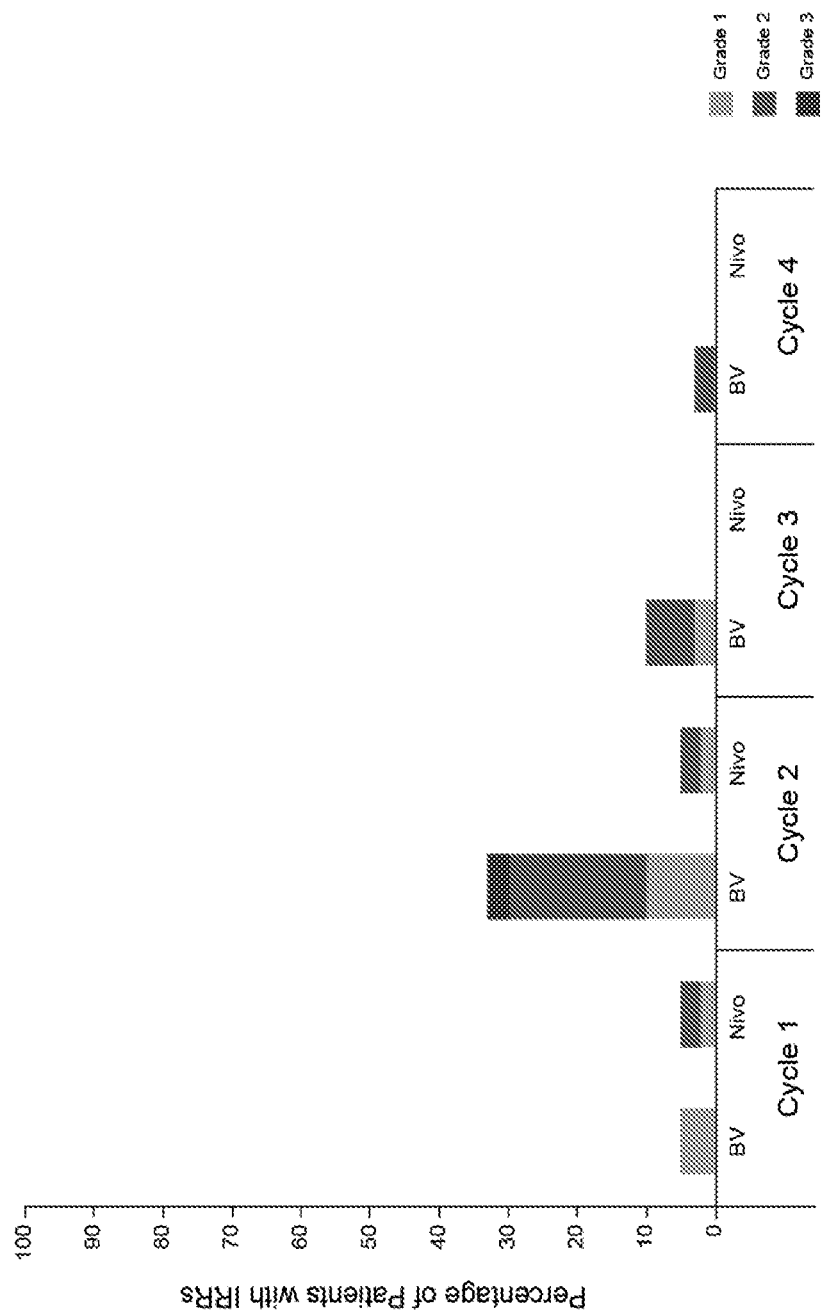

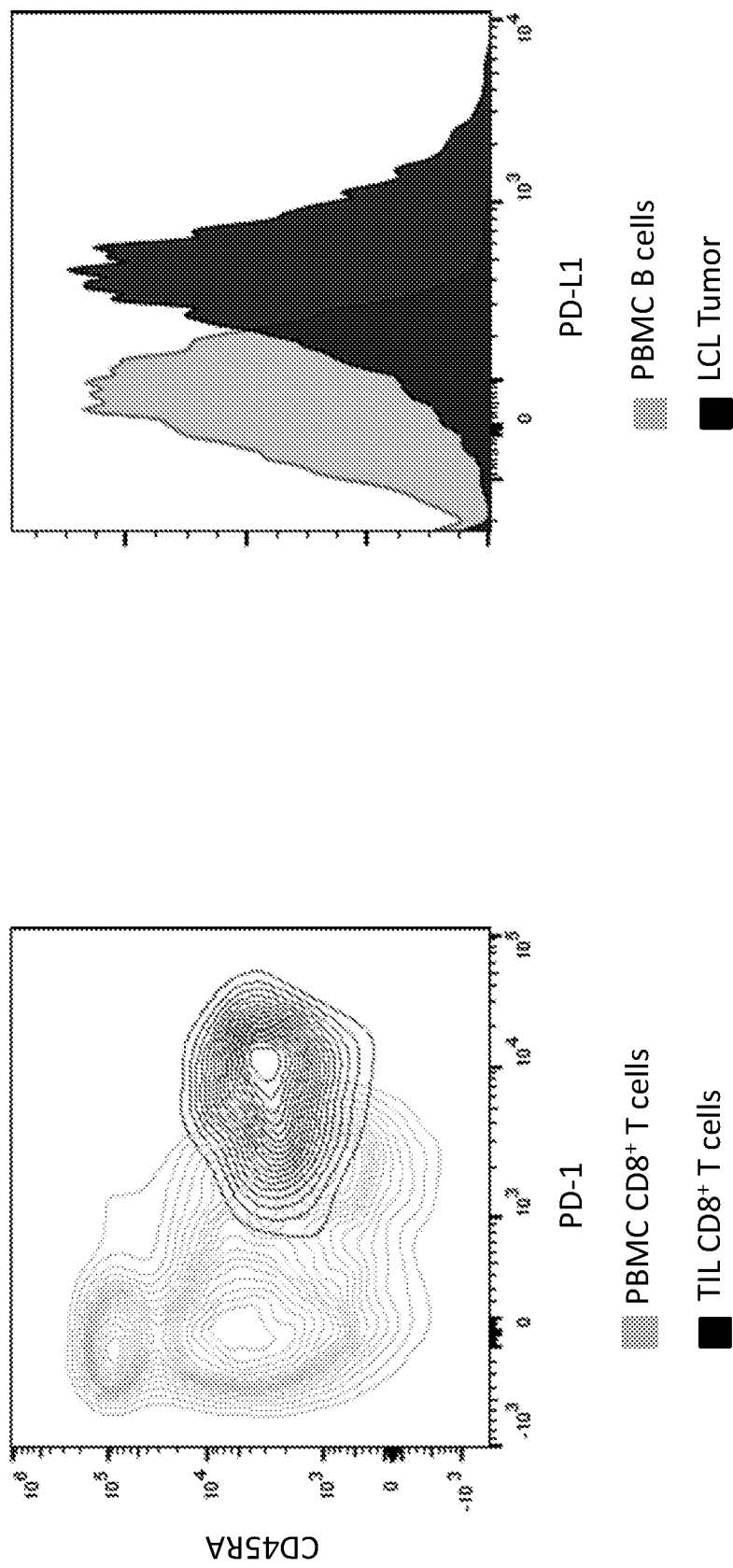

FIG. 15B

| Group | Day 50 Mean+/- SEM tumor volume (mm³) | p-values (one-tailed t-test) | | | | |
|---|---|---|---|---|---|---|
| | | Untreated | hIgG-MMAE | Nivolumab | hIgG-MMAE + Nivo | BV |
| Untreated | 694 +/- 77 | | | | | |
| hIgG-MMAE | 669 +/- 154 | 0.44 | | | | |
| Nivolumab | 792 +/- 68 | 0.19 | 0.23 | | | |
| hIgG-MMAE + Nivo | 531 +/- 81 | 0.09 | 0.21 | 0.02 | | |
| BV | 345 +/- 95 | 0.008 | 0.05 | 0.003 | 0.08 | |
| BV + Nivo | 160 +/- 49 | 0.0001 | 0.003 | 0.0001 | 0.002 | 0.06 |

USE OF AN ANTI-PD-1 ANTIBODY IN COMBINATION WITH AN ANTI-CD30 ANTIBODY IN CANCER TREATMENT

FIELD OF THE DISCLOSURE

This disclosure relates to methods for treating a tumor in a subject comprising administering to the subject an anti-Programmed Death-1 (PD-1) antibody and an anti-CD30 antibody. In some embodiments, the tumor is derived from a lymphoma. In certain embodiments, the tumor is derived from a Hodgkin lymphoma, a non-Hodgkin lymphoma, or a combination thereof.

BACKGROUND OF THE DISCLOSURE

Human cancers harbor numerous genetic and epigenetic alterations, generating neoantigens potentially recognizable by the immune system (Sjoblom et al., (2006) *Science* 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

Until recently, cancer immunotherapy had focused substantial effort on approaches that enhance anti-tumor immune responses by adoptive-transfer of activated effector cells, immunization against relevant antigens, or providing non-specific immune-stimulatory agents such as cytokines. In the past decade, however, intensive efforts to develop specific immune checkpoint pathway inhibitors have begun to provide new immunotherapeutic approaches for treating cancer, including the development of an antibody, ipilimumab (YERVOY®), that binds to and inhibits CTLA-4 for the treatment of patients with advanced melanoma (Hodi et al., 2010 *N Engl J Med* 363:711-23) and the development of antibodies, such as nivolumab and pembrolizumab (formerly lambrolizumab; USAN Council Statement, 2013), that bind specifically to the Programmed Death-1 (PD-1) receptor and block the inhibitory PD-1/PD-1 ligand pathway (Topalian et al., *N Engl J Med* 366:2443-54 (2012a); Topalian et al., *Curr Opin Immunol* 24:207-12 (2012b); Topalian et al., *J Clin Oncol* 32(10):1020-30 (2014); Hamid et al., *N Engl J Med* 369:134-144 (2013); Hamid and Carvajal, *Expert Opin Biol Ther* 13(6):847-61 (2013); and McDermott and Atkins, *Cancer Med* 2(5):662-73 (2013)).

Targeted therapy of multiple non-redundant molecular pathways regulating immune responses can enhance antitumor immunotherapy. However, not all combinations have acceptable safety and/or efficacy. There remains a need for combination therapies with an acceptable safety profile and high efficacy that enhance antitumor immune responses compared to monotherapy and other immunotherapy combinations.

SUMMARY OF THE DISCLOSURE

The present disclosure relates to a method of treating a subject afflicted with a tumor derived from a non-Hodgkin lymphoma comprising administering to the subject: (a) an antibody or an antigen-binding portion thereof that binds specifically to a Programmed Death-1 (PD-1) receptor and inhibits PD-1 activity ("anti-PD-1 antibody"); and (b) an antibody or an antigen-binding portion thereof that specifically binds to CD30 ("anti-CD30 antibody"). In some embodiments, the non-Hodgkin lymphoma is relapsed or refractory non-Hodgkin lymphoma. In certain embodiments, the non-Hodgkin lymphoma is selected from the group consisting of diffuse large B-cell lymphoma (DLBCL), peripheral T-cell lymphoma (PTCL), cutaneous T-cell lymphoma (CTCL), and any combination thereof.

The present disclosure further relates to a method of treating a subject afflicted with a tumor derived from a Hodgkin lymphoma comprising administering to the subject: (a) an anti-PD-1 antibody; and (b) an anti-CD30 antibody. In some embodiments, the Hodgkin lymphoma is classical Hodgkin lymphoma (cHL).

In some embodiments, the tumor comprises one or more cells that express CD30. In certain embodiments, at least 1% of the tumor cells express CD30.

In some embodiments, the anti-CD30 antibody cross-competes for binding to CD30 with cAC10. In some embodiments, the anti-CD30 antibody comprises cAC10. In some embodiments, the anti-CD30 antibody is an anti-CD30 antibody conjugated to a therapeutic agent ("anti-CD30 antibody-drug conjugate"). In certain embodiments, the therapeutic agent comprises monomethyl auristatin E (MMAE). In one particular embodiment, the anti-CD30 antibody is brentuximab vedotin.

In some embodiments, the anti-PD-1 antibody cross-competes with nivolumab for binding to human PD-1. In some embodiments, the anti-PD-1 antibody binds to the same epitope as nivolumab. In one particular embodiment, the anti-PD-1 antibody is nivolumab.

In certain embodiments, the anti-PD-1 antibody is administered at a dose of at least about 3 mg/kg body weight once about every 2 weeks. In some embodiments, the anti-CD30 antibody is administered at a dose of 1.8 mg/kg body weight once about every 3 weeks.

In some embodiments, the tumor comprises one or more cells that express PD-L1, PD-L2, or both.

In some embodiments, the subject received at least one prior chemotherapy treatment. In certain embodiments, the subject was not responsive to a prior chemotherapy treatment.

In some embodiments, the method further comprises administering a stem cell transplant to the patient after administering the anti-PD-1 antibody and the anti-CD30 antibody.

The present disclosure is further directed to a kit for treating a subject afflicted with a cancer, the kit comprising: (a) a dosage ranging from about 4 mg to about 500 mg of an anti-PD-1 antibody; (b) a dosage ranging from about 0.1 mg to about 500 mg of an anti-CD30 antibody; and (c) instructions for using the anti-PD-1 antibody and the anti-CD30 antibody in the method.

The present disclosure is further directed to a kit for treating a subject afflicted with a lymphoma, the kit comprising: (a) a dosage ranging from about 4 mg to about 500 mg of an anti-PD-1 antibody; (b) a dosage ranging from about 0.1 mg to about 500 mg of brentuximab vedotin; and (c) instructions for using the anti-PD-1 antibody and the brentuximab vedotin in the method.

EMBODIMENTS

E1. A method of treating a subject afflicted with a tumor derived from a non-Hodgkin lymphoma comprising administering to the subject: (a) an antibody or an antigen-binding portion thereof that binds specifically to a Programmed Death-1 (PD-1) receptor and inhibits PD-1 activity ("anti- PD-1 antibody"); and (b) an antibody or an antigen-binding portion thereof that specifically binds to CD30 ("anti-CD30 antibody").

E2. The method of embodiment E1, wherein the non-Hodgkin lymphoma is relapsed or refractory non-Hodgkin lymphoma.

E3. The method of embodiment E1 or E2, wherein the non-Hodgkin lymphoma is selected from the group consisting of diffuse large B-cell lymphoma (DLBCL), peripheral T-cell lymphoma (PTCL), cutaneous T-cell lymphoma (CTCL), and any combination thereof.

E4. A method of treating a subject afflicted with a tumor derived from a Hodgkin lymphoma comprising administering to the subject: (a) an anti-PD-1 antibody; and (b) an anti-CD30 antibody.

E5. The method of embodiment E4, wherein the Hodgkin lymphoma is classical Hodgkin lymphoma (cHL).

E6. The method of any one of embodiments E1 to E5, wherein the tumor comprises one or more cells that express CD30.

E7. The method of embodiment E6, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of the tumor cells express CD30.

E8. The method of embodiment E6 or E7, wherein about at least 1% of the tumor cells express CD30.

E9. The method of any one of embodiments E1 to E8, wherein the administering treats the tumor.

E10. The method of any one of embodiments E1 to E9, wherein the anti-CD30 antibody cross-competes for binding to CD30 with cAC10.

E11. The method of any one of embodiments E1 to E9, wherein the anti-CD30 antibody comprises cAC10.

E12. The method of any one of embodiments E1 to E11, wherein the anti-CD30 antibody is an anti-CD30 antibody conjugated to a therapeutic agent ("anti-CD30 antibody-drug conjugate").

E13. The method of embodiment E12, wherein the therapeutic agent comprises an anti-neoplastic agent.

E14. The method of embodiment E13, wherein the anti-neoplastic agent is an anti-mitotic agent.

E15. The method of any one of embodiments E12 to E14, wherein the therapeutic agent comprises monomethyl auristatin E (MMAE).

E16. The method of anyone of embodiments E12 to E15, wherein the anti-CD30 antibody-drug conjugate further comprises a linker between the therapeutic agent and the antibody.

E17. The method of embodiment E16, wherein the linker is a cleavable linker.

E18. The method of anyone of embodiments E1 to E17, wherein the anti-CD30 antibody is brentuximab vedotin.

E19. The method of any one of embodiments E1 to E18, wherein the anti-PD-1 antibody cross-competes with nivolumab for binding to human PD-1.

E20. The method of any one of embodiments E1 to E19, wherein the anti-PD-1 antibody binds to the same epitope as nivolumab.

E21. The method of any one of embodiments E1 to E20, wherein the anti-PD-1 antibody is a chimeric antibody, a humanized antibody, a human monoclonal antibody, or a portion thereof.

E22. The method of any one of embodiments E1 to E21, wherein the anti-PD-1 antibody comprises a heavy chain constant region which is of a human IgG1 or IgG4 isotype.

E23. The method of any one of embodiments E1 to E22, wherein the anti-PD-1 antibody is nivolumab.

E24. The method of any one of embodiments E1 to E22, wherein the anti-PD-1 antibody is pembrolizumab.

E25. The method of any one of embodiments E1 to E24, wherein the anti-PD-1 antibody is administered at a dose ranging from at least about 0.1 mg/kg to at least about 10.0 mg/kg body weight once about every 1, 2 or 3 weeks.

E26. The method of embodiment E25, wherein the anti-PD-1 antibody is administered at a dose of at least about 3 mg/kg body weight once about every 2 weeks.

E27. The method of any one of embodiments E1 to E24, wherein the anti-PD-1 antibody is administered at a flat dose.

E28. The method of any one of embodiments E1 to E24 and E27, wherein the anti-PD-1 antibody is administered at a flat dose of at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, or at least about 550 mg.

E29. The method of any one of embodiments E1 to E24, E27, and E28, wherein the anti-PD-1 antibody is administered at a flat dose about once every 1, 2, 3, or 4 weeks.

E30. The method of any one of embodiments E1 to E29, wherein the anti-PD-1 antibody is administered for as long as clinical benefit is observed or until unmanageable toxicity or disease progression occurs.

E31. The method of any one of embodiments E1 to E30, wherein the anti-CD30 antibody is administered at a dose ranging from at least about 0.1 mg/kg to at least about 180 mg/kg body weight once about every 1, 2, or 3 weeks.

E32. The method of any one of embodiments E1 to E31, wherein the anti-CD30 antibody is administered at a dose ranging from at least about 1.0 mg/kg to at least about 10 mg/kg body weight once about every 1, 2, or 3 weeks.

E33. The method of any one of embodiments E1 to E32, wherein the anti-CD30 antibody is administered at a dose of at least about 2 mg/kg body weight once about every 3 weeks.

E34. The method of any one of embodiments E1 to E32, wherein the anti-CD30 antibody is administered at a dose of 1.8 mg/kg body weight once about every 3 weeks.

E35. The method of any of embodiments E1 to E34, wherein the anti-CD30 antibody is administered for as long as clinical benefit is observed or until unmanageable toxicity or disease progression occurs.

E36. The method of any one of embodiments E1 to E35, wherein the anti-PD-1 and anti-CD30 antibodies are formulated for intravenous administration.

E37. The method of any one of embodiments E1 to E36, wherein the anti-PD-1 and anti-CD30 antibodies are administered sequentially.

E38. The method of any one of embodiments E1 to E37, wherein the anti-PD-1 and anti-CD30 antibodies are administered within 30 minutes of each other.

E39. The method of any one of embodiments E1 to E38, wherein the anti-PD-1 antibody is administered before the anti-CD30 antibody.

E40. The method of any one of embodiments E1 to E39, wherein the anti-CD30 antibody is administered before the anti-PD-1 antibody.

E41. The method of any one of embodiments E1 to E36, wherein the anti-PD-1 antibody and the anti-CD30 antibody are administered concurrently in separate compositions.

E42. The method of any one of embodiments E1 to E36, wherein the anti-PD-1 antibody and the anti-CD30 antibody are admixed as a single composition for concurrent administration.

E43. The method of any one of embodiments E1 to E42, wherein the anti-PD-1 antibody is administered at a subtherapeutic dose.

E44. The method any one of embodiments E1 to E43, wherein the anti-CD30 antibody is administered at a subtherapeutic dose.

E45. The method any one of embodiments E1 to E44, wherein the anti-PD-1 antibody and the anti-CD30 antibody are each administered at a subtherapeutic dose.

E46. The method of any one of embodiments E1 to E45, wherein the tumor comprises one or more cells that express PD-L1, PD-L2, or both.

E47. The method of any one of embodiments E1 to E46, wherein the subject exhibits progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the initial administration.

E48. The method of any one of embodiments E1 to E47, wherein the anti-CD30 antibody is ADCETRIS®.

E49. The method of any one of embodiments E1 to E48, wherein the anti-PD-1 antibody is OPDIVO®.

E50. The method of any one of embodiments E1 to E49, wherein the subject received at least one prior chemotherapy treatment.

E51. The method of any one of embodiments E1 to E50, wherein the subject received at least two prior chemotherapy treatments.

E52. The method of any one of embodiments E1 to E51, wherein the subject was not responsive to a prior chemotherapy treatment.

E53. The method of any one of embodiments E1 to E52, further comprising administering a stem cell transplant to the patient after administering the anti-PD-1 antibody and the anti-CD30 antibody.

E54. The method of embodiment E53, wherein the stem cell transplant comprises autologous stem cells.

E55. A kit for treating a subject afflicted with a cancer, the kit comprising: (a) a dosage ranging from about 4 mg to about 500 mg of an anti-PD-1 antibody; (b) a dosage ranging from about 0.1 mg to about 500 mg of an anti-CD30 antibody; and (c) instructions for using the anti-PD-1 antibody and the anti-CD30 antibody in the method of any of embodiments E1 to E54.

E56. A kit for treating a subject afflicted with a lymphoma, the kit comprising: (a) a dosage ranging from about 4 mg to about 500 mg of an anti-PD-1 antibody; (b) a dosage ranging from about 0.1 mg to about 500 mg of brentuximab vedotin; and (c) instructions for using the anti-PD-1 antibody and the brentuximab vedotin in the method of any of embodiments E1 to E54.

E57. The method of any one of embodiments E4 to E54, wherein the Hodgkin lymphoma is relapsed or refractory Hodgkin lymphoma.

E58. The method of embodiment E25, wherein the anti-PD-1 antibody is administered at a dose of at least about 3 mg/kg body weight once about every 3 weeks.

E59. The method of any one of embodiments E1 to E24, wherein the anti-CD30 antibody is administered to the subject on day 1 of a first 21-day cycle and the anti-PD-1 antibody is administered to the subject on day 8 of the first 21-day cycle.

E60. The method of embodiment E59, further comprising administering a combination of the anti-CD30 antibody and the anti-PD-1 antibody on day 1 of each of a second 21-day cycle, a third 21-day cycle, and a fourth 21-day cycle, wherein the second 21-day cycle, the third 21-day cycle, and the fourth 21-day cycle follow in succession after the first 21-day cycle.

E61. The method of embodiment E59 or E60, wherein the anti-CD30 antibody is administered at a dose of about 1.8 mg/kg.

E62. The method of any one of embodiments E59 to E61, wherein the anti-PD-1 antibody is administered at a dose of about 3 mg/kg.

E63. The method of any one of embodiments E59 to E62, wherein the anti-CD30 antibody, the anti-PD-1 antibody, or both the anti-CD30 antibody and the anti-PD-1 antibody are administered to the subject intravenously.

E64. The method of any one of embodiments E59 to E63, wherein the anti-CD30 antibody comprises brentuximab vedotin.

E65. The method of any one of embodiments E59 to E64, wherein the anti-PD-1 antibody comprises nivolumab.

BRIEF DESCRIPTION OF THE DRAWINGS

FIGS. 6A-6D show priming of the immune system of patients treated with brentuximab vedotin (BV) in combination with nivolumab. Serum TARC levels were significantly lower compared to baseline following single agent BV administration and following BV and nivolumab dosing (FIG. 6A). T-cell chemokine IP10 levels were significantly higher after C1D1 BV and following C1D8 nivolumab dosing (FIG. 6B). Pro-inflammatory cytokine IL-18 levels were significantly higher after C1D1 BV dosing and remained stable with BV and nivolumab dosing (FIG. 6C). Pro-inflammatory cytokines such as IFNγ were significantly higher after BV and nivolumab dosing (C1D15) compared to baseline (FIG. 6D).

FIGS. 7A-7C show peripheral blood immunophenotyping. T helper subsets, such as Tregs, (FIG. 7A), activated $CD4^+$ T cells (FIG. 7B), and proliferating $CD4^+$ T cells (FIG. 7C), which were reduced after single agent BV dosing, expanded after BV and nivolumab combination dosing.

FIG. 8 shows adverse events associated with BV and nivolumab dosing.

FIG. 9 shows infusion-related reactions (IRRs) associated with BV and nivolumab dosing.

FIGS. 14A-14D show immune cell infiltration into autologous tumors following BV and nivolumab combination therapy. CD8+ T cell and NK cell counts relative to tumor mass (FIG. 14A) and total cell count (FIG. 14B) were increased after BV and nivolumab combination dosing. CD8+ T cells and LCL tumor cells expressed increased levels of PD-1 (FIG. 14C) and PD-L1 (FIG. 14D). TIL=tumor infiltrating lymphocyte; PBMC=peripheral blood mononuclear cell.

FIGS. 15A-15B show BV enhances immune-mediated tumor clearance alone and in combination with nivolumab. Relative tumor volume decreased over time following treatment (FIG. 15A), and mean tumor volume substantially decreased after treatment with BV and nivolumab in combination (FIG. 15B). BV=brentuximab vedotin; Nivo=nivolumab; PBMC=peripheral blood mononuclear cell; hIgG-MMAE=control.

DETAILED DESCRIPTION OF THE DISCLOSURE

Figure 1:
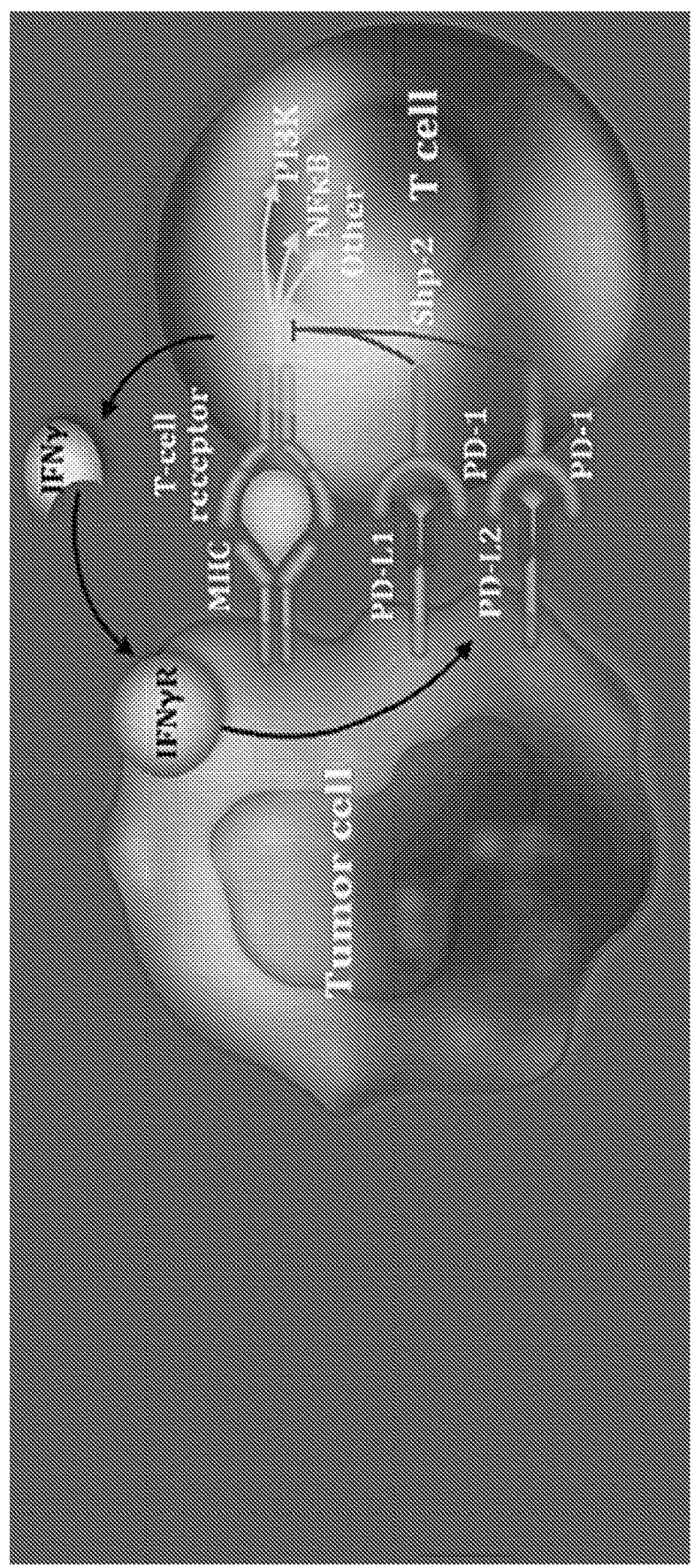
FIG. 1 shows a schematic drawing of the PD-1 pathway and the mode of action of nivolumab. MHC=major histocompatibility complex; NFKB=nuclear factor kappa B; PI3K=phosphoinositide-3 kinase; Shp2=Src homology 2 domain-containing tyrosine phosphatase.

This disclosure relates to methods for treating a tumor in a subject comprising administering to the subject an anti-Programmed Death-1 (PD-1) antibody and an anti-CD30 antibody. In some embodiments, the tumor is derived from a lymphoma. In certain embodiments, the tumor is derived from a Hodgkin lymphoma, a non-Hodgkin lymphoma, or a combination thereof.

Terms

In order that the present disclosure can be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of a therapeutic agent to a subject, using any of the various methods and delivery systems known to those skilled in the art. Exemplary routes of administration for the anti-PD-1 antibody include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. A therapeutic agent can be administered via a non-parenteral route, or orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, or disease associated with the use of a medical treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises at least three constant domains, $C_{H1}$, $C_{H2}$ and $C_{H3}$. Each light chain comprises a light chain variable region (abbreviated herein as $V_L$) and a light chain constant region. The light chain constant region comprises one constant domain, $C_L$. The $V_H$ and $V_L$ regions can be further subdivided into regions of hypervariability, termed complementarity determining regions (CDRs), interspersed with regions that are more conserved, termed framework regions (FRs). Each $V_H$ and $V_L$ comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

An immunoglobulin can derive from any of the commonly known isotypes, including but not limited to IgA, secretory IgA, IgG, and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes. The term "antibody" includes, by way of example, both naturally occurring and non-naturally occurring antibodies; monoclonal and polyclonal antibodies; chimeric and humanized antibodies; human or non-human antibodies; wholly synthetic antibodies; and single chain antibodies. A non-human antibody can be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

An "isolated antibody" refers to an antibody that is substantially free of other antibodies having different antigenic specificities (e.g., an isolated antibody that binds specifically to PD-1 is substantially free of antibodies that bind specifically to antigens other than PD-1). An isolated antibody that binds specifically to PD-1 can, however, have cross-reactivity to other antigens, such as PD-1 molecules from different species. Moreover, an isolated antibody can be substantially free of other cellular material and/or chemicals. In one embodiment, an antibody includes a conjugate attached to another agent (e.g., small molecule drug). In some embodiments, an anti-CD30 antibody includes a conjugate of an anti-CD30 antibody with a small molecule drug (e.g., MMAE).

The term "monoclonal antibody" (mAb) refers to a non-naturally occurring preparation of antibody molecules of single molecular composition, i.e., antibody molecules whose primary sequences are essentially identical, and which exhibits a single binding specificity and affinity for a particular epitope. A monoclonal antibody is an example of an isolated antibody. Monoclonal antibodies can be produced by hybridoma, recombinant, transgenic, or other techniques known to those skilled in the art.

A "human antibody" (HuMAb) refers to an antibody having variable regions in which both the FRs and CDRs are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human antibodies" and "fully human antibodies" and are used synonymously.

A "humanized antibody" refers to an antibody in which some, most, or all of the amino acids outside the CDRs of a non-human antibody are replaced with corresponding amino acids derived from human immunoglobulins. In one embodiment of a humanized form of an antibody, some, most, or all of the amino acids outside the CDRs have been replaced with amino acids from human immunoglobulins, whereas some, most, or all amino acids within one or more CDRs are unchanged. Small additions, deletions, insertions, substitutions or modifications of amino acids are permissible as long as they do not abrogate the ability of the antibody to bind to a particular antigen. A "humanized antibody" retains an antigenic specificity similar to that of the original antibody. In some embodiments, the CDRs of a humanized antibody contain CDRs from a non-human, mammalian antibody. In other embodiments, the CDRs of a humanized antibody contain CDRs from an engineered, synthetic antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen antibody" refers to an antibody that binds specifically to the antigen. For example, an anti-PD-1 antibody binds specifically to PD-1 and an anti-CD30 antibody binds specifically to CD30.

An "antigen-binding portion" of an antibody (also called an "antigen-binding fragment") refers to one or more fragments of an antibody that retain the ability to bind specifically to the antigen bound by the whole antibody.

A "cancer" refers a broad group of various diseases characterized by the uncontrolled growth of abnormal cells in the body. A "cancer" or "cancer tissue" can include a tumor. Unregulated cell division and growth results in the formation of malignant tumors that invade neighboring tissues and can also metastasize to distant parts of the body through the lymphatic system or bloodstream. Following metastasis, the distal tumors can be said to be "derived from" the pre-metastasis tumor. For example, a "tumor derived from" a non-Hodgkin lymphoma refers to a tumor that is the result of a metastasized non-Hodgkin lymphoma. Because the distal tumor is derived from the pre-metastasis tumor, the "derived from" tumor can also comprise the pre-metastasis tumor, e.g., a tumor derived from a non-Hodgkin lymphoma can comprise a non-Hodgkin lymphoma.

"CD30" or "TNFRSF8" refers to a receptor that is a member of the tumor necrosis factor receptor superfamily. CD30 is a transmembrane glycoprotein expressed on activated $CD4^+$ and $CD8^+$ T cells and B cells, and virally-infected lymphocytes. CD30 interacts with TRAF2 and TRAF3 to mediate signal transduction that leads to activation of NF-κB. CD30 acts as a positive regulator of apoptosis, and it has been shown to limit the proliferative potential of auto-reactive CD8 effector T cells. CD30 is also expressed by various forms of lymphoma, including Hodgkin lymphoma (CD30 is expressed by Reed-Sternberg cells) and non-Hodgkin lymphoma (e.g., diffuse large B-cell lymphoma (DLBCL), peripheral T-cell lymphoma (PTCL), and cutaneous T-cell lymphoma (CTCL).

The term "immunotherapy" refers to the treatment of a subject afflicted with, at risk of contracting, or suffering a recurrence of a disease by a method comprising inducing, enhancing, suppressing, or otherwise modifying an immune response.

"Treatment" or "therapy" of a subject refers to any type of intervention or process performed on, or the administration of an active agent to, the subject with the objective of reversing, alleviating, ameliorating, inhibiting, slowing down, or preventing the onset, progression, development, severity, or recurrence of a symptom, complication, condition, or biochemical indicia associated with a disease.

"Programmed Death-1" (PD-1) refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

"Programmed Death Ligand-1" (PD-L1) is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

A "subject" includes any human or non-human animal. The term "nonhuman animal" includes, but is not limited to, vertebrates such as nonhuman primates, sheep, dogs, and rodents such as mice, rats, and guinea pigs. In some embodiments, the subject is a human. The terms "subject" and "patient" are used interchangeably herein.

A "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

As used herein, "subtherapeutic dose" means a dose of a therapeutic compound (e.g., an antibody) that is lower than the usual or typical dose of the therapeutic compound when administered alone for the treatment of a hyperproliferative disease (e.g., cancer).

By way of example, an "anti-cancer agent" promotes cancer regression in a subject. In some embodiments, a therapeutically effective amount of the drug promotes cancer regression to the point of eliminating the cancer. "Promoting cancer regression" means that administering an effective amount of the drug, alone or in combination with an anti-cancer agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity or other adverse physiological effects at the cellular, organ and/or organism level (adverse effects) resulting from administration of the drug.

By way of example for the treatment of tumors, a therapeutically effective amount of an anti-cancer agent inhibits cell growth or tumor growth by at least about 10%, by at least about 20%, by at least about 30%, by at least about 40%, by at least about 50%, by at least about 60%, by at least about 70%, or by at least about 80%, by at least about 90%, at least about 95%, or at least about 100% relative to untreated subjects.

In other embodiments of the disclosure, tumor regression can be observed and continue for a period of at least about 20 days, at least about 30 days, at least about 40 days, at least about 50 days, or at least about 60 days. Notwithstanding these ultimate measurements of therapeutic effectiveness, evaluation of immunotherapeutic drugs must also make allowance for "immune-related response patterns".

An "immune-related response pattern" refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

A therapeutically effective amount of a drug includes a "prophylactically effective amount," which is any amount of the drug that, when administered alone or in combination with an anti-cancer agent to a subject at risk of developing a cancer (e.g., a subject having a pre-malignant condition) or of suffering a recurrence of cancer, inhibits the development or recurrence of the cancer. In some embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

The term "weight-based dose", as referred to herein, means that a dose administered to a patient is calculated based on the weight of the patient. For example, when a patient with 60 kg body weight requires 3 mg/kg of an anti-PD-1 antibody, one can calculate and use the appropriate amount of the anti-PD-1 antibody (i.e., 180 mg) for administration.

The use of the term "fixed dose" with regard to a method of the disclosure means that two or more different antibodies in a single composition (e.g., anti-PD-1 antibody and anti-CD30 antibody) are present in the composition in particular (fixed) ratios with each other. In some embodiments, the fixed dose is based on the weight (e.g., mg) of the antibodies. In certain embodiments, the fixed dose is based on the concentration (e.g., mg/ml) of the antibodies. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody (e.g., anti-PD-1 antibody) to mg second antibody (e.g., anti-CD30 antibody). For example, the 3:1 ratio of an anti-PD-1 antibody and an anti-CD30 antibody can mean that a vial can contain about 240 mg of the anti-PD-1 antibody and 80 mg of the anti-CD30 antibody or about 3 mg/ml of the anti-PD-1 antibody and 1 mg/ml of the anti-CD30 antibody.

The use of the term "flat dose" with regard to the methods and dosages of the disclosure means a dose that is administered to a patient without regard for the weight or body surface area (BSA) of the patient. The flat dose is therefore not provided as a mg/kg dose, but rather as an absolute amount of the agent (e.g., the anti-CD30 antibody and/or anti-PD-1 antibody). For example, a 60 kg person and a 100 kg person would receive the same dose of an antibody (e.g., 240 mg of an anti-PD-1 antibody).

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

The terms "once about every week," "once about every two weeks," or any other similar dosing interval terms as used herein mean approximate numbers. "Once about every week" can include every seven days±one day, i.e., every six days to every eight days. "Once about every two weeks" can include every fourteen days±three days, i.e., every eleven days to every seventeen days. Similar approximations apply, for example, to once about every three weeks, once about every four weeks, once about every five weeks, once about every six weeks, and once about every twelve weeks. In some embodiments, a dosing interval of once about every six weeks or once about every twelve weeks means that the first dose can be administered any day in the first week, and then the next dose can be administered any day in the sixth or twelfth week, respectively. In other embodiments, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively.

As described herein, any concentration range, percentage range, ratio range, or integer range is to be understood to include the value of any integer within the recited range and, when appropriate, fractions thereof (such as one tenth and one hundredth of an integer), unless otherwise indicated.

Various aspects of the disclosure are described in further detail in the following subsections.

Methods of the Disclosure

The present disclosure is directed to a method for treating a tumor or a subject afflicted with a tumor comprising administering to the subject a therapeutically effective amount of an antibody or an antigen-binding portion thereof that binds specifically to a Programmed Death-1 (PD-1) receptor and inhibits PD-1 activity ("anti-PD-1 antibody") or an antibody or an antigen-binding portion thereof that binds specifically to a Programmed Death Ligand1 (PD-L1) receptor and inhibits PD-L1 activity ("anti-PD-L1 antibody") and a therapeutically effective amount of an antibody or an antigen-binding portion thereof that binds specifically to CD30 ("anti-CD30 antibody").

In some embodiments, the tumor is derived from a Hodgkin lymphoma (HL), a non-Hodgkin lymphoma (NHL), or a combination thereof. In certain embodiments, the subject has received one, two, three, four, five or more prior cancer treatments. In other embodiments, the subject is treatment-naïve. In some embodiments, the subject has progressed on other cancer treatments. In some embodiments, the tumor has reoccurred. In some embodiments, the tumor is metastatic. In other embodiments, the tumor is not metastatic.

In certain embodiments, the tumor is derived from an HL (e.g., a tumor comprising an HL). In certain embodiments, the HL is a classical HL (cHL; e.g., a nodular sclerosing HL, a mixed cellularity HL, a lymphocyte rich HL, or a lymphocyte depleted HL). In other embodiments, the HL is a nodular lymphocyte predominant type HL.

In other embodiments, the tumor is derived from a NHL. In some embodiments, the tumor comprises an NHL. In certain embodiments, the NHL is a relapsed or refractor NHL. In some embodiments, the NHL is a B-cell lymphoma, e.g., a diffuse large B-cell lymphoma (DLBCL), a follicular lymphoma (FL), a Burkitt lymphoma, an immunoblastic large cell lymphoma, a precursor B-lymphoblastic lymphoma, a mantle cell lymphoma, or any combination thereof. In some embodiments, the NHL is a T-cell lymphoma, e.g., a cutaneous T-cell lymphoma (CTCL), a peripheral T-cell lymphoma (PTCL), a mycosis fungoides, an anaplastic large cell lymphoma, a precursor T-lymphoblastic lymphoma, or any combination thereof. In certain embodiments, the NHL is selected from a DLBCL, a PTCL, a CTCL, and any combination thereof.

In other embodiments, the present methods comprise administering an effective amount of an anti-PD-1 antibody and an effective amount of an anti-CD30 antibody. An effective amount of an anti-PD-1 antibody and/or an anti-CD30 antibody can be a flat dose or a weight based dose.

In some embodiments, the disclosure includes a method of treating a cancer or a subject afflicted with cancer comprising administering an anti-PD-1 antagonist in combination with an anti-CD30 antibody to treat cancer. An "anti-PD-1 antagonist" as referred herein includes any molecule that inhibits interaction between PD-1 (receptor) and PD-L1 (ligand) such that the signal pathway of PD-1/PD-L1 is blocked. In other embodiments, an anti-PD-1 antagonist is a PD-1-Fc fusion protein. In certain embodiments, an anti-PD-1 antagonist includes an anti-PD-1 fusion protein, an antisense molecule, a small molecule, a ribozyme, or a nanobody that inhibits or prevents interaction between PD-1 and PD-L1.

In certain embodiments, the therapy of the present disclosure (e.g., administration of an anti-PD-1 antibody and the anti-CD30 antibody) effectively increases the duration of survival of the subject. For example, the duration of survival of the subject is increased by at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 1 year or more when compared to another subject treated with only either another therapy or, only one of the two members of the combination therapy alone (e.g., an anti-PD-1 antibody alone) or an alternative combination therapy. In other embodiments, the combination therapy of an anti-PD-1 antibody and an anti-CD30 antibody increases the duration of survival of the subject at a level similar to the duration of survival of the subject using a combination therapy of an anti-PD-L1 antibody and brentuximab vedotin (anti-CD30 antibody). In still other embodiments, the combination therapy of an anti-PD-1 antibody (e.g., nivolumab or pembrolizumab) and an anti-CD30 antibody (e.g., brentuximab vedotin) increases the duration of survival of the subject at a level higher than (about one month higher than, about two months higher than, about three months higher than, about four months higher than, about five months higher than, about six months higher than, about seven months higher than, about eight months higher than, about nine months higher than, about ten months higher than, about eleven months higher than, or about one year higher than the duration of survival of the subject using a combination therapy of an anti-PD-L1 antibody (e.g., MPDL3280A or atezolizumab) and brentuximab vedotin (anti-CD30 antibody).

In certain embodiments, the therapy of the present disclosure effectively increases the duration of progression-free survival of the subject. For example, the progression free survival of the subject is increased by at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 1 year when compared to another subject treated with only either another therapy or only one of the two members of the combination therapy alone (e.g., an anti-PD-1 antibody alone) or an alternative combination therapy.

In certain embodiments, the therapy of the present disclosure effectively increases the response rate in a group of subjects. For example, the response rate in a group of subjects is increased by at least about 2%, at least about 3%, at least about 4%, at least about 5%, at least about 10%, at least about 15%, at least about 20%, at least about 25%, at least about 30%, at last about 35%, at least about 40%, at least about 45%, at least about 50%, at least about 55%, at least about 60%, at least about 70%, at least about 75%, at least about 80%, at least about 85%, at least about 90%, at least about 95%, at least about 99% or at least about 100% when compared to another group of subjects treated with only either another therapy or, only one of the two members of the combination therapy alone (e.g., an anti-PD-1 antibody alone) or an alternative combination therapy.

In certain embodiments, the methods of the present disclosure lower a serum thymus and activation-regulated chemokine (TARC) level in the subject after the administration of the anti-PD-1 antibody and the anti-CD30 antibody in combination, compared to the serum TARC level at the baseline (no administration or before the administration) or after the administration of the anti-PD-1 antibody or the anti-CD30 antibody alone (monotherapy). In some embodiments, the serum TARC level is lowered after the administration at least one fold, at least 1.5 fold, at least two fold, at least three fold, at least four fold, at least five fold, at least six fold, at least seven fold, at least eight fold, at least nine fold, at least ten fold, at least 11 fold, at least 12 fold, at least 13 fold, at least 14 fold, at least 15 fold, at least 16 fold, at least 17 fold, at least 18 fold, at least 19 fold, or at least 20 fold compared to the serum TARC level at the baseline (no administration or before the administration) or after the monotherapy. In other embodiments, the methods of the present disclosure increase the level of a pro-inflammatory cytokine, e.g., Interleukin-18 (IL-18) and/or Interferon-γ, in the subject after the administration of the anti-PD-1 antibody and the anti-CD30 antibody in combination, compared to the level of the pro-inflammatory cytokine at the baseline (no administration or before the administration) or after the administration of the anti-PD-1 antibody or the anti-CD30 antibody alone (monotherapy). The level of the pro-inflammatory cytokine can be increased at least 1 fold, at least 1.5 fold, at least 2 fold, at least 3 fold, at least 5 fold, at least 6 fold, at least 7 fold, at least 8 fold, at least 9 fold, at least 10 fold, at least 11 fold, at least 12 fold, at least 13 fold, at least 14 fold, at least 15 fold, at least 16 fold, at least 17 fold, at least 18 fold, at least 19 fold, or at least 20 fold after the administration of the combination therapy. In yet other embodiments, the methods of the present disclosure increase the level of a T cell chemokine, e.g., IP10, in the subject after the administration of the anti-PD-1 antibody and the anti-CD30 antibody in combination, compared to the level of the T cell chemokine at the baseline (no administration or before the administration) or after the administration of the anti-PD-1 antibody or the anti-CD30 antibody alone (monotherapy). In some embodiments, the level of the T cell chemokine is increased at least 1 fold, at least 1.5 fold, at least 2 fold, at least 3 fold, at least 5 fold, at least 6 fold, at least 7 fold, at least 8 fold, at least 9 fold, at least 10 fold, at least 11 fold, at least 12 fold, at least 13 fold, at least 14 fold, at least 15 fold, at least 16 fold, at least 17 fold, at least 18 fold, at least 19 fold, or at least 20 fold after the administration of the combination therapy.

In other embodiments, the present method provides a method of reducing the serum level of TARC in a subject afflicted with a tumor derived from a Hodgkin lymphoma (HL), a non-Hodgkin lymphoma (NHL), or a combination thereof comprising administering to the subject a therapeutically effective amount of an anti-PD-1 antibody and an anti-CD30 antibody. In some embodiments, the serum TARC level is lowered after the administration at least one fold, at least 1.5 fold, at least two fold, at least three fold, at least four fold, at least five fold, at least six fold, at least seven fold, at least eight fold, at least nine fold, at least ten fold, at least 11 fold, at least 12 fold, at least 13 fold, at least 14 fold, at least 15 fold, at least 16 fold, at least 17 fold, at least 18 fold, at least 19 fold, or at least 20 fold compared to the serum TARC level at the baseline (no administration or before the administration) or after the monotherapy.

In some embodiments, the present method provides a method of increasing the level of a pro-inflammatory cytokine (e.g., IL-18 and/or IFNγ) and/or a T cell chemokine (e.g., IP10) in a subject afflicted with a tumor derived from a Hodgkin lymphoma (HL), a non-Hodgkin lymphoma (NHL), or a combination thereof comprising administering to the subject a therapeutically effective amount of an anti-PD-1 antibody and an anti-CD30 antibody. In some embodiments, the level of the pro-inflammatory cytokine and/or T cell chemokine is increased at least 1 fold, at least 1.5 fold, at least 2 fold, at least 3 fold, at least 5 fold, at least 6 fold, at least 7 fold, at least 8 fold, at least 9 fold, at least 10 fold, at least 11 fold, at least 12 fold, at least 13 fold, at least 14 fold, at least 15 fold, at least 16 fold, at least 17 fold, at least 18 fold, at least 19 fold, or at least 20 fold after the administration of the combination therapy.

In certain embodiments, the present methods (e.g., combination therapy of an anti-PD-1 antibody and an anti-CD30 antibody) also activate and/or proliferate T cells, e.g., CD4+ T cells, e.g., Follicular helper CD4 T cells (Tfh), T helper cells (Th1 and/or Th2), T helper 17 (T17) cells, and/or regulatory T cells (Tregs), or CD8+ T cells, compared to the administration of the anti-CD30 antibody alone or the baseline (no administration or before the administration). In some embodiments, the present methods increase the number of T cells, e.g., CD4+ T cells, regulatory T cells (Tregs) compared to the administration of the anti-CD30 antibody alone or the baseline (no administration or before the administration).

In some embodiments, the anti-PD-1 and anti-CD30 antibodies are formulated for intravenous administration. In certain embodiments, the anti-PD-1 and anti-CD30 antibodies are administered sequentially. In certain embodiments, the anti-PD-1 and anti-CD30 antibodies are administered within 30 minutes of each other. In one embodiment, the anti-PD-1 antibody or antigen-binding portion thereof is administered before the anti-CD30 antibody or antigen-binding portion thereof. In another embodiment, the anti CD30 antibody or antigen-binding portion thereof is administered before the anti-PD-1 antibody or antigen-binding portion thereof. In another embodiment, the anti-PD-1 antibody or antigen-binding portion thereof and the anti-CD30 antibody or antigen-binding portion thereof are administered concurrently in separate compositions. In a further embodiment, the anti-PD-1 antibody or antigen-binding portion thereof and the anti-CD30 antibody or antigen-binding portion thereof are admixed as a single composition for concurrent administration.

In some embodiments, the anti-PD-1 antibody and anti-CD30 antibody are administered in a fixed dose.

Anti-PD-1 and Anti-PD-L1 Antibodies

The combination therapy of the present disclosure can utilize an anti-PD-1 antibody or an antigen-binding fragment thereof. PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to down regulate T cell activation and cytokine secretion upon binding to PD-1. Inhibition of the PD-1/PD-L1 interaction mediates potent antitumor activity in preclinical models.

Human monoclonal antibodies that bind specifically to PD-1 with high affinity have been disclosed in U.S. Pat. No. 8,008,449. Other anti-PD-1 mABs have been described in, for example, U.S. Pat. Nos. 6,808,710, 7,488,802, 8,168,757 and 8,354,509, and PCT Publication No. WO 2012/145493. Each of the anti-PD-1 human monoclonal antibodies disclosed in U.S. Pat. No. 8,008,449 has been demonstrated to exhibit one or more of the following characteristics: (a) binds to human PD-1 with a KD of $1\times10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates antibody responses; and/or (j) inhibits tumor cell growth in vivo. Anti-PD-1 antibodies usable in the present disclosure include monoclonal antibodies that bind specifically to human PD-1 and exhibit at least one, at least two, at least three, at least four, or at least five of the preceding characteristics.

In one embodiment, the anti-PD-1 antibody is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 Cancer Immunol Res. 2(9): 846-56). Nivolumab has shown activity in a variety of advanced solid tumors including renal cell carcinoma (renal adenocarcinoma, or hypernephroma), melanoma, and non-small cell lung cancer (NSCLC) (Topalian et al., 2012a; Topalian et al., 2014; Drake et al., 2013; WO 2013/173223). In another embodiment, the anti-PD-1 antibody or fragment thereof cross-competes with nivolumab. In some embodiments, the anti-PD-1 antibody binds to the same epitope as nivolumab. In certain embodiments, the anti-PD-1 antibody has the same CDRs as nivolumab.

In another embodiment, the anti-PD-1 antibody (or antigen-binding portion thereof) cross-competes with pembrolizumab. In some embodiments, the anti-PD-1 antibody binds to the same epitope as pembrolizumab. In certain embodiments, the anti-PD-1 antibody has the same CDRs as pembrolizumab. In another embodiment, the anti-PD-1 antibody is pembrolizumab. Pembrolizumab (also known as "KEYTRUDA®", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. No. 8,900,587; see also cancer.gov/drugdictionary?cdrid=695789 (last accessed: Dec. 14, 2014). Pembrolizumab has been approved by the FDA for the treatment of relapsed or refractory melanoma and advanced NSCLC.

In other embodiments, the anti-PD-1 antibody (or antigen-binding portion thereof) cross-competes with MEDI0680. In some embodiments, the anti-PD-1 antibody binds to the same epitope as MEDI0680. In certain embodiments, the anti-PD-1 antibody has the same CDRs as MEDI0680. In other embodiments, the anti-PD-1 antibody is MEDI0680 (formerly AMP-514), which is a monoclonal antibody against the PD-1 receptor. MEDI0680 is described, for example, in U.S. Pat. No. 8,609,089B2 or in cancer.gov/drugdictionary?cdrid=756047 (last accessed Dec. 14, 2014).

In certain embodiments, an immune checkpoint inhibitor is AMP-224, which is a B7-DC Fc fusion protein. AMP-224 is discussed in U.S. Publ. No. 2013/0017199 or in cancer.gov/publications/dictionaries/cancer-drug?cdrid=700595 (last accessed Jul. 8, 2015).

In other embodiments, the anti-PD-1 antibody (or antigen-binding portion thereof) cross-competes with BGB-A317. In some embodiments, the anti-PD-1 antibody binds to the same epitope as BGB-A317. In certain embodiments, the anti-PD-1 antibody has the same CDRs as BGB-A317. In certain embodiments, the anti-PD-1 antibody is BGB-A317, which is a humanized monoclonal antibody. BGB-A317 is described in U.S. Publ. No. 2015/0079109.

In other embodiments, the anti-PD-1 antibody (or antigen-binding portion thereof) cross-competes with INCSHR1210 (SHR-1210). In some embodiments, the anti- PD-1 antibody binds to the same epitope as INCSHR1210 (SHR-1210). In certain embodiments, the anti-PD-1 antibody has the same CDRs as INCSHR1210 (SHR-1210). In certain embodiments, the anti-PD-1 antibody is INCSHR1210 (SHR-1210), which is a human monoclonal antibody. INCSHR1210 (SHR-1210) is described in WO2015/085847.

In other embodiments, the anti-PD-1 antibody (or antigen-binding portion thereof) cross-competes with REGN-2810. In some embodiments, the anti-PD-1 antibody binds to the same epitope as REGN-2810. In certain embodiments, the anti-PD-1 antibody has the same CDRs as REGN-2810. In certain embodiments, the anti-PD-1 antibody is REGN-2810, which is a human monoclonal antibody. REGN-2810 is described in WO2015/112800.

In other embodiments, the anti-PD-1 antibody (or antigen-binding portion thereof) cross-competes with PDR001. In some embodiments, the anti-PD-1 antibody binds to the same epitope as PDR001. In certain embodiments, the anti-PD-1 antibody has the same CDRs as PDR001. In certain embodiments, the anti-PD-1 antibody is PDR001, which is a humanized monoclonal antibody. PDR001 is described in WO2015/112900.

In other embodiments, the anti-PD-1 antibody (or antigen-binding portion thereof) cross-competes with TSR-042 (ANB011). In some embodiments, the anti-PD-1 antibody binds to the same epitope as TSR-042 (ANB011). In certain embodiments, the anti-PD-1 antibody has the same CDRs as TSR-042 (ANB011). In certain embodiments, the anti-PD-1 antibody is TSR-042 (ANB011), which is a humanized monoclonal antibody. TSR-042 (ANB011) is described in WO2014/179664.

In other embodiments, the anti-PD-1 antibody (or antigen-binding portion thereof) cross-competes with STI-1110. In some embodiments, the anti-PD-1 antibody binds to the same epitope as STI-1110. In certain embodiments, the anti-PD-1 antibody has the same CDRs as STI-1110. In certain embodiments, the anti-PD-1 antibody is STI-1110, which is a human monoclonal antibody. STI-1110 is described in WO2014/194302.

Anti-PD-1 antibodies usable in the disclosed methods also include isolated antibodies that bind specifically to human PD-1 and cross-compete for binding to human PD-1 with nivolumab (see, e.g., U.S. Pat. No. 8,008,449; WO 2013/173223). The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar to those of nivolumab by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 as nivolumab are monoclonal antibodies. For administration to human subjects, these cross-competing antibodies can be chimeric antibodies, or can be humanized or human antibodies. Such chimeric, humanized or human monoclonal antibodies can be prepared and isolated by methods well known in the art.

Anti-PD-1 antibodies usable in the methods of the disclosed disclosure also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')2 fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, or any combination thereof.

In certain embodiments, the anti-PD-1 antibody or antigen-binding portion thereof comprises a heavy chain constant region which is of a human IgG1 or IgG4 isotype. In certain other embodiments, the sequence of the IgG4 heavy chain constant region of the anti-PD-1 antibody or antigen-binding portion thereof contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al., 2014). In yet other embodiments, the antibody comprises a light chain constant region which is a human kappa or lambda constant region. In other embodiments, the anti-PD-1 antibody or antigen-binding portion thereof is a monoclonal antibody or an antigen-binding portion thereof. In certain embodiments of any of the therapeutic methods described herein comprising administration of an anti-PD-1 antibody, the anti-PD-1 antibody is nivolumab. In other embodiments, the anti-PD-1 antibody is pembrolizumab. In other embodiments, the anti-PD-1 antibody is chosen from the human antibodies 17D8, 2D3, 4H1, 4A11, 7D3, and 5F4 described in U.S. Pat. No. 8,008,449. In still other embodiments, the anti-PD-1 antibody is MEDI0680 (formerly AMP-514), AMP-224, or BGB-A317.

In other embodiments, the anti-PD-1 antibody or antigen-binding portion thereof is a chimeric, humanized or human monoclonal antibody or a portion thereof. In certain embodiments for treating a human subject, the antibody is a humanized antibody. In other embodiments for treating a human subject, the antibody is a human antibody. Antibodies of an IgG1, IgG2, IgG3, or IgG4 isotype can be used.

In certain embodiments, an anti-PD-1 antibody used in the methods can be replaced with another PD-1 or anti-PD-L1 antagonist. For example, because an anti-PD-L1 antibody prevents interaction between PD-1 and PD-L1, thereby exerting similar effects to the signaling pathway of PD-1, an anti-PD-L1 antibody can replace the use of an anti-PD-1 antibody in the methods disclosed herein. Therefore, in one embodiment, the present disclosure is directed to a method for treating a subject afflicted with a tumor comprising administering to the subject a therapeutically effective amount an anti-PD-L1 antibody and an anti-CD30 antibody.

In certain embodiments, the anti-PD-L1 antibody is BMS-936559 (formerly 12A4 or MDX-1105) (see, e.g., U.S. Pat. No. 7,943,743; WO 2013/173223).

In other embodiments, the anti-PD-L1 antibody is MPDL3280A (also known as RG7446 and atezolizumab) (see, e.g., Herbst et al. (2013) *J Clin Oncol* 31(suppl):3000. Abstract.; U.S. Pat. No. 8,217,149).

In other embodiments, the anti-PD-L1 antibody is MEDI4736 (also called Durvalumab; Khleif (2013) In: Proceedings from the European Cancer Congress 2013; September 27-Oct. 1, 2013; Amsterdam, The Netherlands.

Abstract 802, See U.S. Pat. No. 8,779,108 or US 2014/0356353, filed May 6, 2014).

In further embodiments, the anti-PD-L1 antibody is MSB0010718C (also called Avelumab; See US 2014/0341917).

In other embodiments, the anti-PD-L1 antibody is CX-072 (also called CytomX; See WO2016/149201).

In certain embodiments, the anti-PD-L1 antibodies cross-compete for binding to human PD-L1 with, or bind to the same epitope region of human PD-L1 as the above-references PD-L1 antibodies. In other embodiments, the anti-PD-L1 antibodies useful for the combination therapy with an anti-CD30 antibody are monoclonal antibodies. For administration to human subjects, these cross-competing antibodies can be chimeric antibodies, or can be humanized or human antibodies. Such chimeric, humanized, or human monoclonal antibodies can be prepared and isolated by methods well known in the art.

Anti-CD30 Antibodies

The combination therapy of the present disclosure also utilizes an anti-CD30 antibody or an antigen-binding fragment thereof. CD30 receptors are members of the tumor necrosis factor receptor superfamily involved in limiting the proliferative potential of autoreactive CD8 effector T cells. Antibodies targeting CD30 can potentially be either agonists or antagonists of these CD30 activities.

In some embodiments, the anti-CD30 antibody is cAC10. cAC10 is a chimeric IgG1 monoclonal antibody that specifically binds CD30. cAC10 induces growth arrest of $CD30^+$ cell lines in vitro and has pronounced antitumor activity in severe combined immunodeficiency (SCID) mouse xenograft models of Hodgkin disease. See Francisco et al., *Blood* 102(4):1458-64 (2003).

In some embodiments, the anti-CD30 antibody is conjugated to a therapeutic agent, e.g., the anti-CD30 antibody comprises an anti-CD30 antibody-drug conjugate. In some embodiments, the therapeutic agent comprises an anti-neoplastic agent (e.g., an anti-mitotic agent). In certain embodiments, the therapeutic agent is selected from the group consisting of monomethyl auristatin E (MMAE), auristatin drug analogues, can tansinoids (maytansine; DMs), dolastatins, cryptophycin, duocarmycin, duocarmycin derivatives, esperamicin, calicheamicin, pyrolobenodiazepine (PBD), and any combination thereof. In one particular embodiment, the anti-CD30 antibody is conjugated to MMAE. The antibody can be conjugated to at least one, at least two, at least three, at least four, at least five, at least six, at least seven, at least eight, at least nine, or at least ten molecules of the therapeutic agent. In one embodiment, the anti-CD30 antibody is conjugated to four molecules of the therapeutic agent, e.g., four molecules of MMAE.

In some embodiments, the anti-CD30 antibody-drug conjugate further comprises a linker between the therapeutic agent and the antibody. In some embodiments, the linker comprises one or more naturally occurring amino acids, one or more non-naturally occurring (e.g., synthetic) amino acids, a chemical linker, or any combination thereof. In certain embodiments, the linker is a cleavable linker, e.g., a protease cleavable linker. In certain embodiments, the linker is specifically cleaved upon uptake by a target cell, e.g., upon uptake by a cell expressing CD30. In some embodiments, cleavage of the linker activates a cytotoxic activity of the therapeutic agent.

In one embodiment, the anti-CD30 antibody comprises brentuximab vedotin. In one particular embodiment, the anti-CD30 antibody is brentuximab vedotin. Brentuximab vedotin (BV; also known as "ADCETRIS®") is a CD30-directed antibody-drug conjugate (ADC) comprising a chimeric anti-CD30 antibody (cAC10), a therapeutic agent (MMAE), and a protease-cleavable linker between the cAC10 and the MMAE. BV comprises approximately four molecules of MMAE linked to each cAC10 antibody molecule. In one embodiment, the anti-CD30 antibody is ADCETRIS®. ADCETRIS® is approved by the FDA for treatment of patients with Hodgkin lymphoma after failure of autologous stem cell transplant (ASCT) or after failure of at least two prior multi-agent chemotherapy regimens in patients who are not ASCT candidates and for the treatment of patients with systemic anaplastic large cell lymphoma after failure of at least one prior multi-agent chemotherapy regimen.

In one embodiment, the anti-CD30 antibody is an anti-CD30 antibody or fragment thereof that binds to the same epitope as cAC10, e.g., the same epitope as brentuximab vedotin. In certain embodiments, the anti-CD30 antibody is an antibody that has the same CDRs as cAC10, e.g., the same CDRs as brentuximab vedotin. Antibodies that bind to the same epitope are expected to have functional properties very similar to those of cAC10 by virtue of their binding to the same epitope region of CD30. These antibodies can be readily identified based on their ability to, for example, cross-compete with cAC10 in standard CD30 binding assays such as Biacore analysis, ELISA assays, or flow cytometry.

In certain embodiments, the antibodies that cross-compete for binding to human CD30 with, or bind to the same epitope region of human CD30 as cAC10 are monoclonal antibodies. For administration to human subjects, these cross-competing antibodies can be chimeric antibodies, or can be humanized or human antibodies. Such chimeric, humanized, or human monoclonal antibodies can be prepared and isolated by methods well known in the art. Anti-CD30 antibodies usable in the methods of the disclosed disclosure also include antigen-binding portions of the above antibodies.

In other embodiments, the anti-CD30 antibody or antigen-binding portion thereof is a chimeric, humanized, or human monoclonal antibody or a portion thereof. In certain embodiments for treating a human subject, the antibody is a humanized antibody. In other embodiments for treating a human subject, the antibody is a human antibody. Antibodies of an IgG1, IgG2, IgG3, or IgG4 isotype can be used.

Cancer and Standard-of-Care Therapies

In some embodiments, the methods disclosed herein are used in place of standard of care therapies. In certain embodiments, a standard of care therapy is used in combination with any method disclosed herein. Standard-of-care therapies for different types of cancer are well known by persons of skill in the art. For example, the National Comprehensive Cancer Network (NCCN), an alliance of 21 major cancer centers in the USA, publishes the NCCN Clinical Practice Guidelines in Oncology (NCCN GUIDELINES®) that provide detailed up-to-date information on the standard-of-care treatments for a wide variety of cancers (see NCCN GUIDELINES®, 2014, available at: nccn.org/professionals/physician_gls/f_guidelines.asp, last accessed May 14, 2014).

Lymphoma

The combination therapy of the present disclosure can be used to treat a tumor derived from a lymphoma. Lymphoma is a form of cancer that affects the immune system. The majority of lymphomas fall within two categories: Hodgkin lymphoma (HL) and non-Hodgkin lymphoma (NHL). NHL is the most common form of lymphoma, accounting for about 90% of all cases of lymphoma, whereas HL accounts for only about 10% of all cases of lymphoma. Accordingly, in some embodiments, the lymphoma is an HL. In other embodiments, the lymphoma is an NHL.

NHL will account for an estimated 72,000 new cases (4.3% of all new cancer cases) and 20,000 deaths (3.4% of all cancer-related deaths) in the U.S. in 2017. Howlader N et al., SEER Cancer Statistics Review, 1975-2014, based on November 2016 SEER data submission. Diffuse large B-cell lymphoma (DLBCL), the most common NHL subtype, has an incidence rate of 7.14 per 100,000 persons per year (P-Y), including up to 10% primary mediastinal B-cell lymphoma (PMBL). Dunleavy K et al., *Blood* 2015; 125:33-39. Incidence rates of peripheral T-cell lymphoma (PTCL) and mycosis fungoides/Sézary syndrome (MF/SS) are 0.60 and 0.52 per 100,000 P-Y. Morton L M et al., *Blood* 2006; 107:265-276. Within the two main categories of lymphoma, HL and NHL, there are several specific subgroups of lymphomas. Hodgkin lymphomas can include, but are not limited to, classical HL (cHL; e.g., nodular sclerosing HL, mixed cellularity HL, lymphocyte rich HL, and lymphocyte depleted HL) and nodular lymphocyte predominant type HL. Non-Hodgkin Lymphomas can include, but are not limited to, B-cell lymphomas (e.g., diffuse large B-cell lymphoma (DLBCL), follicular lymphoma (FL), Burkitt lymphoma, immunoblastic large cell lymphoma, precursor B-lymphoblastic lymphoma, and mantle cell lymphoma) and T cell lymphomas (e.g., a cutaneous T-cell lymphoma (CTCL), a peripheral T-cell lymphoma (PTCL), a mycosis fungoides, an anaplastic large cell lymphoma, and a precursor T-lymphoblastic lymphoma).

Treatment guidelines for relapsed/refractory (R/R) NHL recommend multi-agent chemotherapy (combined with targeted therapy for B-cell lymphomas), brentuximab vedotin (BV), autologous or allogeneic hematopoietic stem cell transplantation (HSCT), and/or radiotherapy, with addition of topical therapies for MF/SS. National Comprehensive Cancer Network, Non-Hodgkin Lymphoma (version 3.2016). 5-year relative survival rates are 48%, 44%, and 86% in DLBCL, PTCL, and MF/SS, respectively. Han X et al., *Cancer Causes Control* 2008; 19:841-858.

In certain aspects, the present disclosure is directed to a method of treating a subject afflicted with a tumor derived from a Hodgkin lymphoma (HL) comprising administering to the subject (a) an anti-PD-1 antibody, and (b) an anti-CD30 antibody. In some embodiments, the tumor comprises an HL. In one particular embodiment, the HL is classical HL (cHL).

In certain aspects, the present disclosure is directed to a method of treating a subject afflicted with a tumor derived from a non-Hodgkin lymphoma (NHL) comprising administering to the subject (a) an anti-PD-1 antibody, and (b) an anti-CD30 antibody. In some embodiments, the tumor comprises an NHL. In certain embodiments, the NHL is a relapsed or refractory NHL. In some embodiments, the NHL is a B-cell lymphoma, e.g., a diffuse large B-cell lymphoma (DLBCL), a follicular lymphoma (FL), a Burkitt lymphoma, an immunoblastic large cell lymphoma, a precursor B-lymphoblastic lymphoma, a mantle cell lymphoma, or any combination thereof. In some embodiments, the NHL is a T-cell lymphoma, e.g., a cutaneous T-cell lymphoma (CTCL), a peripheral T-cell lymphoma (PTCL), a mycosis fungoides, an anaplastic large cell lymphoma, a precursor T-lymphoblastic lymphoma, or any combination thereof. In particular embodiments, the NHL is selected from the group consisting of a DLBCL, a PTCL, a CTCL, and any combination thereof.

Various lymphomas are known to express CD30. For example, CD30 is expressed by Reed-Sternberg cells typical of HL, and CD30 expression has been observed in various forms of NHL, including, but not limited to, diffuse large B-cell lymphoma (DLBCL), peripheral T-cell lymphoma (PTCL), and cutaneous T-cell lymphoma (CTCL). Accordingly, in some embodiments, the tumor comprises one or more cells that express CD30. In some embodiments, at least about 0.01%, at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the tumor cells express CD30. In one particular embodiment, at least about 1% of the tumor cells express CD30. In another embodiment, at least about 10% of the tumor cells express CD30. In another embodiment, at least about 20% of the tumor cells express CD30. In another embodiment, at least about 30% of the tumor cells express CD30. In another embodiment, at least about 40% of the tumor cells express CD30. In another embodiment, at least about 50% of the tumor cells express CD30.

The PD-L1 status of a tumor (e.g., a tumor derived from a NHL and/or a HL) in a subject can be measured prior to administering any composition or utilizing any method disclosed herein. PD-L1 expression can be determined by any methods known in the art.

In order to assess the PD-L1 expression, in one embodiment, a test tissue sample can be obtained from the patient who is in need of the therapy. In another embodiment, the assessment of PD-L1 expression can be achieved without obtaining a test tissue sample. In some embodiments, selecting a suitable patient includes (i) optionally providing a test tissue sample obtained from a patient with cancer of the tissue, the test tissue sample comprising tumor cells and/or tumor-infiltrating inflammatory cells; and (ii) assessing the proportion of cells in the test tissue sample that express PD-L1 on the surface of the cells based on an assessment that the proportion of cells in the test tissue sample that express PD-L1 on the cell surface is higher than a predetermined threshold level.

In any of the methods comprising the measurement of PD-L1 expression in a test tissue sample, however, it should be understood that the step comprising the provision of a test tissue sample obtained from a patient is an optional step. It should also be understood that in certain embodiments the "measuring" or "assessing" step to identify, or determine the number or proportion of, cells in the test tissue sample that express PD-L1 on the cell surface is performed by a transformative method of assaying for PD-L1 expression, for example by performing a reverse transcriptase-polymerase chain reaction (RT-PCR) assay or an IHC assay. In certain other embodiments, no transformative step is involved and PD-L1 expression is assessed by, for example, reviewing a report of test results from a laboratory. In certain embodiments, the steps of the methods up to, and including, assessing PD-L1 expression provides an intermediate result that may be provided to a physician or other healthcare provider for use in selecting a suitable candidate for the anti-PD-1 antibody or anti-PD-L1 antibody therapy. In certain embodiments, the steps that provide the intermediate result is performed by a medical practitioner or someone acting under the direction of a medical practitioner. In other embodiments, these steps are performed by an independent laboratory or by an independent person such as a laboratory technician.

In certain embodiments of any of the present methods, the proportion of cells that express PD-L1 is assessed by performing an assay to determine the presence of PD-L1 RNA. In further embodiments, the presence of PD-L1 RNA is determined by RT-PCR, in situ hybridization or RNase protection. In other embodiments, the proportion of cells that express PD-L1 is assessed by performing an assay to determine the presence of PD-L1 polypeptide. In further embodiments, the presence of PD-L1 polypeptide is determined by immunohistochemistry (IHC), enzyme-linked immunosorbent assay (ELISA), in vivo imaging, or flow cytometry. In some embodiments, PD-L1 expression is assayed by IHC. In other embodiments of all of these methods, cell surface expression of PD-L1 is assayed using, e.g., IHC or in vivo imaging. Chen et al., (2013) Clin Cancer Res 19(13): 3462-3473.

Imaging techniques have provided important tools in cancer research and treatment. Recent developments in molecular imaging systems, including positron emission tomography (PET), single-photon emission computed tomography (SPECT), fluorescence reflectance imaging (FM), fluorescence-mediated tomography (FMT), bioluminescence imaging (BLI), laser-scanning confocal microscopy (LSCM) and multiphoton microscopy (MPM), will likely herald even greater use of these techniques in cancer research. Some of these molecular imaging systems allow clinicians to not only see where a tumor is located in the body, but also to visualize the expression and activity of specific molecules, cells, and biological processes that influence tumor behavior and/or responsiveness to therapeutic drugs (Condeelis and Weissleder, "In vivo imaging in cancer," *Cold Spring Harb. Perspect. Biol.* 2(12): a003848 (2010)). Antibody specificity, coupled with the sensitivity and resolution of PET, makes immunoPET imaging particularly attractive for monitoring and assaying expression of antigens in tissue samples (McCabe and Wu, "Positive progress in immunoPET—not just a coincidence," *Cancer Biother. Radiopharm.* 25(3):253-61 (2010); Olafsen et al., "ImmunoPET imaging of B-cell lymphoma using 124I-anti-CD20 scFv dimers (diabodies)," *Protein Eng. Des. Sel.* 23(4):243-9 (2010)). In certain embodiments of any of the present methods, PD-L1 expression is assayed by immunoPET imaging. In certain embodiments of any of the present methods, the proportion of cells in a test tissue sample that express PD-L1 is assessed by performing an assay to determine the presence of PD-L1 polypeptide on the surface of cells in the test tissue sample. In certain embodiments, the test tissue sample is a FFPE tissue sample. In other embodiments, the presence of PD-L1 polypeptide is determined by IHC assay. In further embodiments, the IHC assay is performed using an automated process. In some embodiments, the IHC assay is performed using an anti-PD-L1 monoclonal antibody to bind to the PD-L1 polypeptide.

In one embodiment of the present methods, an automated IHC method is used to assay the expression of PD-L1 on the surface of cells in FFPE tissue specimens. This disclosure provides methods for detecting the presence of human PD-L1 antigen in a test tissue sample, or quantifying the level of human PD-L1 antigen or the proportion of cells in the sample that express the antigen, which methods comprise contacting the test sample, and a negative control sample, with a monoclonal antibody that specifically binds to human PD-L1, under conditions that allow for formation of a complex between the antibody or portion thereof and human PD-L1. In certain embodiments, the test and control tissue samples are FFPE samples. The formation of a complex is then detected, wherein a difference in complex formation between the test sample and the negative control sample is indicative of the presence of human PD-L1 antigen in the sample. Various methods are used to quantify PD-L1 expression.

In a particular embodiment, the automated IHC method comprises: (a) deparaffinizing and rehydrating mounted tissue sections in an autostainer; (b) retrieving antigen using a decloaking chamber and pH 6 buffer, heated to 110° C. for 10 min; (c) setting up reagents on an autostainer; and (d) running the autostainer to include steps of neutralizing endogenous peroxidase in the tissue specimen; blocking non-specific protein-binding sites on the slides; incubating the slides with primary antibody; incubating with a post primary blocking agent; incubating with NovoLink Polymer; adding a chromogen substrate and developing; and counterstaining with hematoxylin.

For assessing PD-L1 expression in tumor tissue samples, a pathologist examines the number of membrane PD-L1$^+$ tumor cells in each field under a microscope and mentally estimates the percentage of cells that are positive, then averages them to come to the final percentage. The different staining intensities are defined as 0/negative, 1+/weak, 2+/moderate, and 3+/strong. Typically, percentage values are first assigned to the 0 and 3+ buckets, and then the intermediate 1+ and 2+ intensities are considered. For highly heterogeneous tissues, the specimen is divided into zones, and each zone is scored separately and then combined into a single set of percentage values. The percentages of negative and positive cells for the different staining intensities are determined from each area and a median value is given to each zone. A final percentage value is given to the tissue for each staining intensity category: negative, 1+, 2+, and 3+. The sum of all staining intensities needs to be 100%. In one embodiment, the threshold number of cells that needs to be PD-L1 positive is at least about 100, at least about 125, at least about 150, at least about 175, or at least about 200 cells. In certain embodiments, the threshold number or cells that needs to be PD-L1 positive is at least about 100 cells.

Staining is also assessed in tumor-infiltrating inflammatory cells such as macrophages and lymphocytes. In most cases macrophages serve as an internal positive control since staining is observed in a large proportion of macrophages. While not required to stain with 3+ intensity, an absence of staining of macrophages should be taken into account to rule out any technical failure. Macrophages and lymphocytes are assessed for plasma membrane staining and only recorded for all samples as being positive or negative for each cell category. Staining is also characterized according to an outside/inside tumor immune cell designation. "Inside" means the immune cell is within the tumor tissue and/or on the boundaries of the tumor region without being physically intercalated among the tumor cells. "Outside" means that there is no physical association with the tumor, the immune cells being found in the periphery associated with connective or any associated adjacent tissue.

In certain embodiments of these scoring methods, the samples are scored by two pathologists operating independently, and the scores are subsequently consolidated. In certain other embodiments, the identification of positive and negative cells is scored using appropriate software.

A histoscore is used as a more quantitative measure of the IHC data. The histoscore is calculated as follows:

Histoscore=[(% tumor×1 (low intensity))+(% tumor×2 (medium intensity))+(% tumor×3 (high intensity))]

To determine the histoscore, the pathologist estimates the percentage of stained cells in each intensity category within a specimen. Because expression of most biomarkers is heterogeneous the histoscore is a truer representation of the overall expression. The final histoscore range is 0 (no expression) to 300 (maximum expression).

An alternative means of quantifying PD-L1 expression in a test tissue sample IHC is to determine the adjusted inflammation score (AIS) score defined as the density of inflammation multiplied by the percent PD-L1 expression by tumor-infiltrating inflammatory cells (Taube et al., "Colocalization of inflammatory response with B7-h1 expression in human melanocytic lesions supports an adaptive resistance mechanism of immune escape," *Sci. Transl. Med.* 4(127):127ra37 (2012)).

In one embodiment, the PD-L1 expression level of a tumor (e.g., a tumor derived from a NHL and/or a HL) is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, at least about 60%, at least about 70%, at least about 75%, at least about 80%, at least about 85%, at least about 90%, at least about 95%, or about 100%. In another embodiment, the PD-L1 status of a tumor is at least about 1%. In other embodiments, the PD-L1 status of a tumor is at least about 5%. In a certain embodiment, the PD-L1 status of a tumor is at least about 10%. In one embodiment, the PD-L1 status of the tumor is at least about 25%. In a particular embodiment, the PD-L1 status of the tumor is at least about 50%.

"PD-L1 positive" as used herein can be interchangeably used with "PD-L1 expression of at least about 1%". In one embodiment, the PD-L1 positive tumors can thus have at least about 1%, at least about 2%, at least about 5%, at least about 10%, at least about 20%, at least about 25%, at least about 30%, at least about 40%, at least about 50%, at least about 60%, at least about 70%, at least about 75%, at least about 80%, at least about 85%, at least about 90%, at least about 95%, or about 100% of the tumor cells expressing PD-L1 as measured by an automated IHC. In certain embodiments, "PD-L1 positive" means that there are at least 100 cells that express PD-L1 on the surface of the cells.

Pharmaceutical Compositions and Dosages

Therapeutic agents of the present disclosure can be constituted in a composition, e.g., a pharmaceutical composition containing an antibody and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. In some embodiments, the carrier for a composition containing an antibody is suitable for intravenous, intramuscular, subcutaneous, parenteral, spinal, or epidermal administration (e.g., by injection or infusion). A pharmaceutical composition of the disclosure can include one or more pharmaceutically acceptable salts, anti-oxidants, aqueous and non-aqueous carriers, and/or adjuvants such as preservatives, wetting agents, emulsifying agents, and dispersing agents.

Dosage regimens are adjusted to provide the optimum desired response, e.g., a maximal therapeutic response and/or minimal adverse effects. In some embodiments, the anti-PD-1 antibody is administered at a weight-based dose. For administration of an anti-PD-1 antibody, the dosage can range from at least about 0.01 mg/kg to at least about 20 mg/kg, from at least about 0.1 mg/kg to at least about 10 mg/kg, from about 0.01 mg/kg to about 5 mg/kg, from about 1 mg/kg to about 5 mg/kg, from about 2 mg/kg to about 5 mg/kg, from about 1 mg/kg to about 3 mg/kg, from about 7.5 mg/kg to about 12.5 mg/kg, or from about 0.1 mg/kg to about 30 mg/kg of the subject's body weight. For example, dosages can be at least about 0.1 mg/kg, at least about 0.3 mg/kg, at least about 1 mg/kg, at least about 2 mg/kg, at least about 3 mg/kg, at least about 5 mg/kg, or at least about 10 mg/kg body weight. In certain embodiments, the dosage of the anti-PD-1 antibody is 3 mg/kg body weight.

In one embodiment, a dosage regimen for an anti-PD-1 antibody comprises about 0.3-1 mg/kg body weight, about 5 mg/kg body weight, 1-5 mg/kg body weight, or about 1-3 mg/kg body weight via intravenous administration, with the antibody being given every about 14-21 days in up to about 6-week or about 12-week cycles until complete response or confirmed progressive disease. In some embodiments, the antibody treatment, or any combination treatment disclosed herein, is continued for at least about 1 month, at least about 3 months, at least about 6 months, at least about 9 months, at least about 1 year, at least about 18 months, at least about 24 months, at least about 3 years, at least about 5 years, or at least about 10 years.

The dosing schedule is typically designed to achieve exposures that result in sustained receptor occupancy (RO) based on typical pharmacokinetic properties of an antibody. An exemplary treatment regime entails administration once per week, once every 2 weeks, once every 3 weeks, once every 4 weeks, once a month, once every 3-6 months or longer. In certain embodiments, an anti-PD-1 antibody such as nivolumab is administered to the subject once every 2 weeks. In other embodiments, the antibody is administered once every 3 weeks. The dosage and scheduling can change during a course of treatment. The anti-PD-1 antibody can be administered in at least two doses, each of the doses is at an amount of about 0.01 mg/kg to about 5 mg/kg, e.g., 3 mg/kg, at a dosing interval of every two weeks between the two doses. In some embodiments, the anti-PD-1 antibody is administered in at least three, four, five, six, or seven doses (i.e., multiple doses), each of the doses is at an amount of about 0.01 mg/kg to about 5 mg/kg, e.g., 3 mg/kg, at a dosing interval of every two weeks between two adjacently given doses. The dosage and scheduling may change during a course of treatment. For example, a dosing schedule for anti-PD-1 monotherapy can comprise administering the antibody: (i) every 2 weeks in 6-week cycles; (ii) every 4 weeks for six dosages, then every three months; (iii) every 3 weeks; or (iv) 3-10 mg/kg once followed by 1 mg/kg every 2-3 weeks. Considering that an IgG4 antibody typically has a half-life of 2-3 weeks, a dosage regimen for an anti-PD-1 antibody of the disclosure comprises 0.3-10 mg/kg body weight, e.g., 1-5 mg/kg body weight, e.g., 1-3 mg/kg body weight via intravenous administration, with the antibody being given every 14-21 days in up to 6-week or 12-week cycles until complete response or confirmed progressive disease.

In particular embodiments, the anti-PD-1 antibody is administered at a dose ranging from at least about 0.1 mg/kg to at least about 10.0 mg/kg body weight once about every 1, 2, or 3 weeks. In further embodiments, the anti-PD-1 antibody (e.g., nivolumab) is administered at a dose of at least about 3 mg/kg body weight once about every 2 weeks. In other embodiments, the anti-PD-1 antibody (e.g., pembrolizumab) is administered at a dose of at least about 200 mg every 3 weeks or 2 mg/kg (up to 200 mg) every three weeks. In some embodiments, the anti-PD-1 antibody (e.g., avelumab) is administered at a dose of 10 mg/kg every two weeks.

In certain embodiments, an anti-PD-1 antibody is administered at a flat dose. In embodiments, the flat dose of the anti-PD-1 antibody is a dose (e.g., flat dose) of at least about 100-600 mg, at least about 400-500 mg, such as, at least about 480 mg, or at least about 100-300 mg, such as, at least about 200-300 mg, at least about 220-260 mg, at least about 230-250 mg or at least about 240 mg, such as at least about 60 mg, at least about 80 mg, at least about 100 mg, at least about 120 mg, at least about 140 mg, at least about 160 mg, at least about 180 mg, at least about 200 mg, at least about 220 mg, at least about 240 mg, at least about 260 mg, at least about 280 mg, at least about 300 mg, at least about 320 mg, at least about 360 mg, at least about 400 mg, at least about 440 mg, at least about 480 mg, at least about 500 mg, at least about 550 mg, at least about 600 mg, at least about 650 mg, at least about 700 mg, at least about 750 mg, or at least about 800 mg. In one embodiment, the anti-PD-1 antibody is a dose (e.g., flat dose) of at least about 240 mg or at least about 480 mg, e.g., 240 mg to 480 mg, once about every 2 to 4 weeks. In other embodiments, the anti-PD-1 antibody or antigen-binding portion thereof is administered at a dose higher than, i.e., at least about, 240 mg. In a particular embodiment, the anti-PD-1 antibody is administered a flat dose of about 360 mg once about every 3 weeks.

In certain embodiments, an anti-PD-1 antibody is administered at a flat dose. In embodiments, the flat dose of the anti-PD-1 antibody is a dose (e.g., flat dose) of about 100-600 mg, about 400-500 mg, such as, about 480 mg, or about 100-300 mg, such as, about 200-300 mg, about 220-260 mg, about 230-250 mg or about 240 mg, such as about 60 mg, about 80 mg, about 100 mg, about 120 mg, about 140 mg, about 160 mg, about 180 mg, about 200 mg, about 220 mg, about 240 mg, about 260 mg, about 280 mg, about 300 mg, about 320 mg, about 360 mg, about 400 mg, about 440 mg, about 480 mg, about 500 mg, about 550 mg, about 600 mg, about 650 mg, about 720 mg, about 750 mg, or about 800 mg. In one embodiment, the anti-PD-1 antibody is a dose (e.g., flat dose) of about 240 mg or about 480 mg, e.g., 240 mg to 480 mg, once about every 2 to 4 weeks. In other embodiments, the anti-PD-1 antibody or antigen-binding portion thereof is administered at a dose higher than, i.e., about 240 mg. In a particular embodiment, the anti-PD-1 antibody is administered a flat dose of about 360 mg once about every 3 weeks.

In some embodiments, the anti-PD-1 antibody is administered in a fixed dose with the anti-CD30 antibody. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg anti-PD-1 antibody to anti-CD30 antibody.

When used in combinations with other anti-cancer agents, the dosage of an anti-PD-1 antibody can be lowered compared to the monotherapy dose. For example, a dosage of nivolumab that is significantly lower than the typical 3 mg/kg, but not less than 0.001 mg/kg, for instance 0.1 mg/kg or less every 3 or 4 weeks, is regarded as a subtherapeutic dosage. The subtherapeutic doses of an anti-PD-1 antibody used in the methods herein are higher than 0.001 mg/kg and lower than 3 mg/kg. In some embodiments, a subtherapeutic dose is about 0.001 mg/kg to about 1 mg/kg, about 0.01 mg/kg to about 1 mg/kg, about 0.1 mg/kg to about 1 mg/kg, or about 0.001 mg/kg to about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%). (Brahmer et al., *J Clin Oncol* 28:3167-75 2010). In some embodiments, 0.3 mg/kg dosing can allow for sufficient exposure to lead to maximal biologic activity. In a particular embodiment, the anti-CD30 antibody, e.g., BV, is administered at a dose of 1.8 mg/kg once every 3 weeks.

Although higher nivolumab monotherapy dosing up to 10 mg/kg every two weeks has been achieved without reaching the maximum tolerated does (MTD), the significant toxicities reported in other trials of checkpoint inhibitors plus anti-angiogenic therapy (see, e.g., Johnson et al., 2013; Rini et al., 2011) support the selection of a nivolumab dose lower than 10 mg/kg.

In some embodiments, the anti-CD30 antibody (e.g., brentuximab vedotin) is administered at a weight-based dose. For administration of an anti-CD30 antibody (e.g., brentuximab vedotin), the dosage can range from about 0.01 mg/kg to about 20 mg/kg, about 0.05 mg/kg to about 20 mg/kg, about 0.1 mg/kg to about 20 mg/kg, about 0.1 mg/kg to about 15 mg/kg, about 0.1 mg/kg to about 10 mg/kg, about 0.1 mg/kg to about 5 mg/kg, about 0.1 mg/kg to about 4 mg/kg, about 0.1 mg/kg to about 3 mg/kg, about 0.1 to about 2 mg/kg, about 1 to about 10 mg/kg, about 1 to about 10 mg/kg, about 1 to about 8 mg/kg, about 1 to about 5 mg/kg, about 1 to about 3 mg/kg, about 1 to about 2 mg/kg of the subject's body weight. For example, dosages can be about 0.05 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2.0 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, or about 20 mg/kg of the subject's body weight.

In some embodiments, the dosage of the anti-CD30 antibody (e.g., brentuximab vedotin) is 0.1 mg/kg body weight. In other embodiments, the dosage of the anti-CD30 antibody (e.g., brentuximab vedotin) is 0.2 mg/kg body weight. In other embodiments, the dosage of the anti-CD30 antibody (e.g., brentuximab vedotin) is 0.3 mg/kg body weight. In other embodiments, the dosage of the anti-CD30 antibody (e.g., brentuximab vedotin) is 0.4 mg/kg body weight. In other embodiments, the dosage of the anti-CD30 antibody (e.g., brentuximab vedotin) is 0.5 mg/kg body weight. In other embodiments, the dosage of the anti-CD30 antibody (e.g., brentuximab vedotin) is 0.6 mg/kg body weight. In other embodiments, the dosage of the anti-CD30 antibody (e.g., brentuximab vedotin) is 0.7 mg/kg body weight. In other embodiments, the dosage of the anti-CD30 antibody (e.g., brentuximab vedotin) is 0.8 mg/kg body weight. In other embodiments, the dosage of the anti-CD30 antibody (e.g., brentuximab vedotin) is 0.9 mg/kg body weight. In other embodiments, the dosage of the anti-CD30 antibody (e.g., brentuximab vedotin) is 1.0 mg/kg body weight. In other embodiments, the dosage of the anti-CD30 antibody (e.g., brentuximab vedotin) is 1.1 mg/kg body weight. In other embodiments, the dosage of the anti-CD30 antibody (e.g., brentuximab vedotin) is 1.2 mg/kg body weight. In other embodiments, the dosage of the anti-CD30 antibody (e.g., brentuximab vedotin) is 1.3 mg/kg body weight. In other embodiments, the dosage of the anti-CD30 antibody (e.g., brentuximab vedotin) is 1.4 mg/kg body weight. In other embodiments, the dosage of the anti-CD30 antibody (e.g., brentuximab vedotin) is 1.5 mg/kg body weight. In other embodiments, the dosage of the anti-CD30 antibody (e.g., brentuximab vedotin) is 1.6 mg/kg body weight. In other embodiments, the dosage of the anti-CD30 antibody (e.g., brentuximab vedotin) is 1.7 mg/kg body weight. In other embodiments, the dosage of the anti-CD30 antibody (e.g., brentuximab vedotin) is 1.8 mg/kg body weight. In other embodiments, the dosage of the anti-CD30 antibody (e.g., brentuximab vedotin) is 1.9 mg/kg body weight. In other embodiments, the dosage of the anti-CD30 antibody (e.g., brentuximab vedotin) is 2.0 mg/kg body weight. In other embodiments, the dosage of the anti-CD30 antibody (e.g., brentuximab vedotin) is 2.1 mg/kg body weight. In other embodiments, the dosage of the anti-CD30 antibody (e.g., brentuximab vedotin) is 2.2 mg/kg body weight. In other embodiments, the dosage of the anti-CD30 antibody (e.g., brentuximab vedotin) is 2.3 mg/kg body weight. In other embodiments, the dosage of the anti-CD30 antibody (e.g., brentuximab vedotin) is 2.4 mg/kg body weight. In other embodiments, the dosage of the anti-CD30 antibody (e.g., brentuximab vedotin) is 2.5 mg/kg body weight. In other embodiments, the dosage of the anti-CD30 antibody (e.g., brentuximab vedotin) is about 5 mg/kg body weight. In other embodiments, the dosage of the anti-CD30 antibody (e.g., brentuximab vedotin) is about 10 mg/kg body weight.

In certain embodiments, an anti-CD30 antibody (e.g., brentuximab vedotin) is administered at a flat dose. In some embodiments, the flat dose of the anti-CD30 antibody is a dose (e.g., flat dose) of at least about 1-1500 mg, at least about 10-1000 mg, such as, at least about 50-800 mg, at least about 100-600 mg, at least about 100-400 mg or at least about 100-200 mg, such as at least about 1 mg, at least about 3 mg, at least about 5 mg, at least about 8 mg, at least about 10 mg, at least about 20 mg, at least about 30 mg, at least about 40 mg, at least about 50 mg, at least about 60 mg, at least about 70 mg, at least about 80 mg, at least about 90 mg, at least about 100 mg, at least about 110 mg, at least about 120 mg, at least about 130 mg, at least about 140 mg, at least about 150 mg, at least about 160 mg, at least about 170 mg, at least about 180 mg, at least about 190 mg, at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, at least about 600 mg, at least about 700 mg, at least about 800 mg, at least about 900 mg, at least about 1000 mg, at least about 1100 mg, at least about 1200 mg, at least about 1300 mg, at least about 1400 mg, or at least about 1500 mg.

In certain embodiments, an anti-CD30 antibody (e.g., brentuximab vedotin) is administered at a flat dose. In some embodiments, the flat dose of the anti-CD30 antibody is a dose (e.g., flat dose) of about 1-1500 mg, about 10-1000 mg, such as, about 50-800 mg, about 100-600 mg, about 100-400 mg or about 100-200 mg, such as about 1 mg, about 3 mg, about 5 mg, about 8 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, about 500 mg, about 600 mg, about 700 mg, about 800 mg, about 900 mg, about 1000 mg, about 1100 mg, about 1200 mg, about 1300 mg, about 1400 mg, or about 1500 mg.

An exemplary treatment regime entails administration once per week, once about every 2 weeks, once about every 3 weeks, once about every 4 weeks, once about a month, once about every 3-6 months or longer. In certain embodiments, the anti-CD30 antibody (e.g., brentuximab vedotin) is administered once about every 3 weeks.

In some embodiments, a subtherapeutic dose of an anti-CD30 antibody (e.g., brentuximab vedotin) is used in the methods herein. The subtherapeutic dosages of an anti-CD30 antibody (e.g., brentuximab vedotin) used in the methods herein are higher than 0.001 mg/kg and lower than 10 mg/kg. In some embodiments, the subtherapeutic dose is about 0.001 mg/kg-about 10 mg/kg, about 0.01 mg/kg-about 10 mg/kg, about 0.01 mg/kg-about 1 mg/kg, about 0.1 mg/kg-about 1 mg/kg, or about 0.001 mg/kg-about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.2 mg/kg, at least about 0.3 mg/kg, at least about 0.4 mg/kg, at least about 0.5 mg/kg, at least about 0.6 mg/kg, at least about 0.7 mg/kg, at least about 0.8 mg/kg, at least about 0.9 mg/kg, at least about 1 mg/kg, at least about 1.1 mg/kg, at least about 1.2 mg/kg, at least about 1.3 mg/kg, at least about 1.4 mg/kg, at least about 1.5 mg/kg, at least about 1.6 mg/kg, or at least about 1.7 mg/kg body weight.

In certain embodiments, at least about 0.1 mg/kg to about 5 mg/kg of the anti-CD30 antibody (e.g., brentuximab vedotin) and at least about 240 mg of the anti-PD-1 antibody are administered to the subject once about every three weeks. In certain embodiments, at least about 0.1 mg/kg of the anti-CD30 antibody (e.g., brentuximab vedotin) and at least about 240 mg of the anti-PD-1 antibody are administered to the subject once about every three weeks. In certain embodiments, at least about 0.2 mg/kg of the anti-CD30 antibody (e.g., brentuximab vedotin) and at least about 240 mg of the anti-PD-1 antibody are administered to the subject once about every three weeks. In certain embodiments, at least about 0.3 mg/kg of the anti-CD30 antibody (e.g., brentuximab vedotin) and at least about 240 mg of the anti-PD-1 antibody are administered to the subject once about every three weeks. In certain embodiments, at least about 0.4 mg/kg of the anti-CD30 antibody (e.g., brentuximab vedotin) and at least about 240 mg of the anti-PD-1 antibody are administered to the subject once about every three weeks. In certain embodiments, at least about 0.5 mg/kg of the anti-CD30 antibody (e.g., brentuximab vedotin) and at least about 240 mg of the anti-PD-1 antibody are administered to the subject once about every three weeks. In certain embodiments, at least about 0.6 mg/kg of the anti-CD30 antibody (e.g., brentuximab vedotin) and at least about 240 mg of the anti-PD-1 antibody are administered to the subject once about every three weeks. In certain embodiments, at least about 0.7 mg/kg of the anti-CD30 antibody (e.g., brentuximab vedotin) and at least about 240 mg of the anti-PD-1 antibody are administered to the subject once about every three weeks. In certain embodiments, at least about 0.8 mg/kg of the anti-CD30 antibody (e.g., brentuximab vedotin) and at least about 240 mg of the anti-PD-1 antibody are administered to the subject once about every three weeks. In certain embodiments, at least about 0.9 mg/kg of the anti-CD30 antibody (e.g., brentuximab vedotin) and at least about 240 mg of the anti-PD-1 antibody are administered to the subject once about every three weeks. In certain embodiments, at least about 1 mg/kg of the anti-CD30 antibody (e.g., brentuximab vedotin) and at least about 240 mg of the anti-PD-1 antibody are administered to the subject once about every three weeks. In certain embodiments, at least about 1.1 mg/kg of the anti-CD30 antibody (e.g., brentuximab vedotin) and at least about 240 mg of the anti-PD-1 antibody are administered to the subject once about every three weeks. In certain embodiments, at least about 1.2 mg/kg of the anti-CD30 antibody (e.g., brentuximab vedotin) and at least about 240 mg of the anti-PD-1 antibody are administered to the subject once about every three weeks. In certain embodiments, at least about 1.3 mg/kg of the anti-CD30 antibody (e.g., brentuximab vedotin) and at least about 240 mg of the anti-PD-1 antibody are administered to the subject once about every three weeks. In certain embodiments, at least about 1.4 mg/kg of the anti-CD30 antibody (e.g., brentuximab vedotin) and at least about 240 mg of the anti-PD-1 antibody are administered to the subject once about every three weeks. In certain embodiments, at least about 1.5 mg/kg of the anti-CD30 antibody (e.g., brentuximab vedotin) and at least about 240 mg of the anti-PD-1 antibody are administered to the subject once about every three weeks. In certain embodiments, at least about 1.6 mg/kg of the anti-CD30 antibody (e.g., brentuximab vedotin) and at least about 240 mg of the anti-PD-1 antibody are administered to the subject once about every three weeks. In certain embodiments, at least about 1.7 mg/kg of the anti-CD30 antibody (e.g., brentuximab vedotin) and at least about 240 mg of the anti-PD-1 antibody are administered to the subject once about every three weeks. In certain embodiments, at least about 1.8 mg/kg of the anti-CD30 antibody (e.g., brentuximab vedotin) and at least about 240 mg of the anti-PD-1 antibody are administered to the subject once about every three weeks. In certain embodiments, at least about 1.9 mg/kg of the anti-CD30 antibody (e.g., brentuximab vedotin) and at least about 240 mg of the anti-PD-1 antibody are administered to the subject once about every three weeks. In certain embodiments, at least about 2 mg/kg of the anti-CD30 antibody (e.g., brentuximab vedotin) and at least about 240 mg of the anti-PD-1 antibody are administered to the subject once about every three weeks. In certain embodiments, at least about 3 mg/kg of the anti-CD30 antibody (e.g., brentuximab vedotin) and at least about 240 mg of the anti-PD-1 antibody are administered to the subject once about every three weeks. In certain embodiments, at least about 4 mg/kg of the anti-CD30 antibody (e.g., brentuximab vedotin) and at least about 240 mg of the anti-PD-1 antibody are administered to the subject once about every three weeks. In certain embodiments, at least about 5 mg/kg of the anti-CD30 antibody (e.g., brentuximab vedotin) and at least about 240 mg of the anti-PD-1 antibody are administered to the subject once about every three weeks. In certain embodiments, at least about 10 mg/kg of the anti-CD30 antibody (e.g., brentuximab vedotin) and at least about 240 mg of the anti-PD-1 antibody are administered to the subject once about every three weeks. In embodiments, the anti-CD30 antibody is brentuximab vedotin. In some embodiments, the anti-PD-1 antibody is nivolumab.

In certain embodiments, the combination of an anti-PD-1 antibody (e.g., nivolumab) and an anti-CD30 antibody (e.g., brentuximab vedotin) is administered intravenously to the subject once about every 3 weeks for a total of nine weeks. In some embodiments, the nine week cycle is repeated 3 or 4 times. In embodiments, the subject is treated with a combination of an anti-PD-1 antibody (e.g., nivolumab) and an anti-CD30 antibody (e.g., brentuximab vedotin) every 3 weeks for a total of nine weeks and 3 nine-week cycles are performed. In embodiments, the subject is treated with a combination of an anti-PD-1 antibody (e.g., nivolumab) and an anti-CD30 antibody (e.g., brentuximab vedotin) every 3 weeks for a total of nine weeks and 4 nine-week cycles are performed. In embodiments, a subject is treated with the anti-PD-1 antibody for 12 nine-week cycles.

In certain embodiments, the anti-CD30 antibody (e.g., brentuximab vedotin) is administered (e.g., intravenously) to a subject on day 1 of the first cycle (cycle 1 day 1); the anti-PD-1 antibody (e.g., Nivolumab) is administered (e.g., intravenously) to the subject on day 8 of the cycle (cycle 1 day 8); and a combination of an anti-CD30 antibody (e.g., brentuximab vedotin) and an anti-PD-1 antibody (e.g., Nivolumab) is administered (e.g., intravenously) on day 1 of each of cycles 2-4. In some embodiments, each cycle is two weeks, 15 days, three weeks, four weeks, a month, five weeks, or six weeks. In one particular embodiment, the subject is treated with about 1.8 mg/kg of an anti-CD30 antibody (e.g., brentuximab vedotin) on cycle 1 day 1 (e.g., 21 day cycle); about 3 mg/kg of an anti-PD-1 antibody (e.g., Nivolumab) on cycle 1 day 8; and a combination of an anti-CD30 antibody (e.g., brentuximab vedotin) and an anti-PD-1 antibody (e.g., Nivolumab) on day 1 of each of cycles 2-4. In one particular embodiment, the combination of an anti-CD30 antibody (e.g., brentuximab vedotin) and an anti-PD-1 antibody (e.g., Nivolumab) comprises a dose of about 1.8 mg/kg of an anti-CD30 antibody (e.g., brentuximab vedotin) and a dose of about 3 mg/kg of an anti-PD-1 antibody (e.g., Nivolumab).

Treatment is continued as long as clinical benefit is observed or until unacceptable toxicity or disease progression occurs. In certain embodiments, the anti-PD-1 antibody can be administered at the dosage that has been shown to produce the highest efficacy as monotherapy in clinical trials, e.g., about 3 mg/kg of nivolumab administered once about every three weeks (Topalian et al., 2012 *N Engl J Med* 366:2443-54; Topalian et al., 2012 *Curr Opin Immunol* 24:207-12), at a flat dose of 240 mg, or at a significantly lower dose, i.e., at a subtherapeutic dose.

In certain embodiments, the subject is treated with a combination of an anti-PD-1 antibody and an anti-CD30 antibody once about every 3 weeks for a set period of time followed by a monotherapy of an anti-PD-1 antibody or a monotherapy of an anti-CD30 antibody. In some embodiments, the subject is treated with a combination of an anti-PD-1 antibody and an anti-CD30 antibody once about every 3 weeks for about 6 weeks followed by a monotherapy of an anti-PD-1 antibody or a monotherapy of an anti-CD30 antibody. In some embodiments, the subject is treated with a combination of an anti-PD-1 antibody and an anti-CD30 antibody once about every 3 weeks for about 9 weeks followed by a monotherapy of an anti-PD-1 antibody or a monotherapy of an anti-CD30 antibody. In some embodiments, the subject is treated with a combination of an anti-PD-1 antibody and an anti-CD30 antibody once about every 3 weeks for about 12 weeks followed by a monotherapy of an anti-PD-1 antibody or a monotherapy of an anti-CD30 antibody. In some embodiments, the subject is treated with a combination of an anti-PD-1 antibody and an anti-CD30 antibody once about every 3 weeks for about 24 weeks followed by a monotherapy of an anti-PD-1 antibody or a monotherapy of an anti-CD30 antibody. In some embodiments, the subject is treated with a combination of an anti-PD-1 antibody and an anti-CD30 antibody once about every 3 weeks for about 48 weeks followed by a monotherapy of an anti-PD-1 antibody or a monotherapy of an anti-CD30 antibody. The monotherapy of the anti-PD-1 antibody can be administered by any route disclosed herein at any dose disclosed herein. In one embodiment, the monotherapy of the anti-PD-1 antibody is administered intravenously at a flat dose of 240 mg. In another embodiment, the monotherapy of the anti-PD-1 antibody is administered intravenously at a dose of 3 mg/kg or 6 mg/kg. The monotherapy of the anti-CD30 antibody can be administered by any route disclosed herein at any dose disclosed herein. In one embodiment, the monotherapy of the anti-CD30 antibody, e.g., brentuximab vedotin, is administered intravenously at a dose of 1.8 mg/kg.

Dosage and frequency vary depending on the half-life of the antibody in the subject. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is typically administered at relatively infrequent intervals over a long period of time. Some patients continue to receive treatment for the rest of their lives. In therapeutic applications, a relatively high dosage at relatively short intervals is sometimes required until progression of the disease is reduced or terminated, and until the patient shows partial or complete amelioration of symptoms of disease. Thereafter, the patient can be administered a prophylactic regime.

Actual dosage levels of the active ingredients in the pharmaceutical compositions of the present disclosure can be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present disclosure employed, the route of administration, the time of administration, the rate of excretion of the particular compound being employed, the duration of the treatment, other drugs, compounds and/or materials used in combination with the particular compositions employed, the age, sex, weight, condition, general health, and prior medical history of the patient being treated, and like factors well known in the medical arts. A composition of the present disclosure can be administered via one or more routes of administration using one or more of a variety of methods well known in the art. As will be appreciated by the skilled artisan, the route and/or mode of administration will vary depending upon the desired results.

Kits

Also within the scope of the present disclosure are kits comprising an anti-PD-1 antibody and an anti-CD30 antibody for therapeutic uses. Kits typically include a label indicating the intended use of the contents of the kit and instructions for use. The term label includes any writing, or recorded material supplied on or with the kit, or which otherwise accompanies the kit. Accordingly, this disclosure provides a kit for treating a subject afflicted with a cancer, the kit comprising: (a) a dosage ranging from about 4 mg to about 500 mg of an anti-PD-1 antibody or antigen-binding portion thereof; (b) a dosage ranging from about 0.1 mg to about 500 mg of an anti-CD30 antibody or antigen-binding portion thereof; and (c) instructions for using the anti-PD-1 antibody and the anti-CD30 antibody in any of the combination therapy methods disclosed herein. In certain embodiments, the anti-PD-1 antibody, the anti-CD30 can be co-packaged in unit dosage form. In certain embodiments for treating human patients, the kit comprises an anti-human PD-1 antibody disclosed herein, e.g., nivolumab, pembrolizumab, MEDI0680 (formerly AMP-514), AMP-224, or BGB-A317. In other embodiments, the kit comprises an anti-human CD30 antibody disclosed herein, e.g., brentuximab vedotin.

The present disclosure is further illustrated by the following examples which should not be construed as further limiting. The contents of all references cited throughout this application are expressly incorporated herein by reference.

EXAMPLES

Example 1

A phase 1/2 open-label, international, multicenter study (NCT02581631), is underway to investigate the safety and efficacy of nivolumab combined with BV in patients with relapsed/refractory NHL.

Background

Treatment options for patients with relapsed, refractory non-Hodgkin lymphoma (NHL) are limited. Nivolumab is a fully human IgG4 monoclonal antibody immune checkpoint inhibitor that targets programmed death receptor-1 (PD-1) to restore active T-cell immune responses against the tumor (FIG. 1). Nivolumab has approval in the United States as treatment for metastatic melanoma, metastatic non-small cell lung cancer, and advanced renal cell carcinoma. Safety and tolerability of nivolumab is consistent across both solid and hematologic tumor types. While PD-1 blockade has shown encouraging activity in aggressive B-cell and T-cell NHL—a phase 1 trial demonstrated an objective response rate (ORR) of 36% in heavily pretreated patients with relapsed, refractory diffuse large B-cell lymphoma (DLBCL)—the majority of patients either do not respond or progress after an initial response. Combination therapy with therapeutic agents such as antibody-drug conjugates can increase the frequency and durability of responses, through both direct cell killing and immunogenic consequences of cell death.

Figure 2:
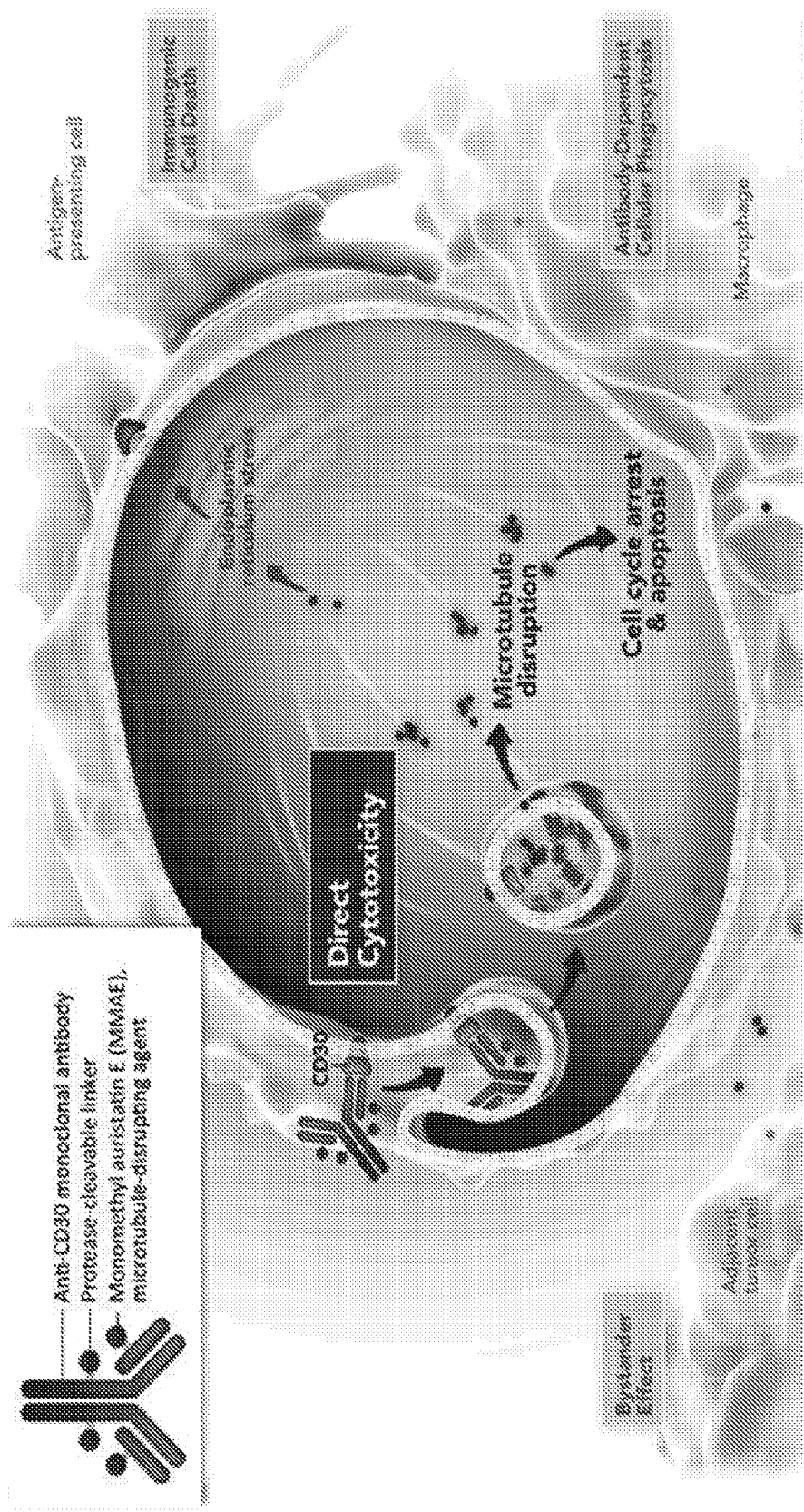
FIG. 2 shows a schematic drawing of the mechanism of action of brentuximab vedotin and secondary effects.

Brentuximab vedotin (BV) is a CD30-directed antibody-drug conjugate that has shown anti-tumor activity in a range of lymphoid malignancies. BV works primarily by inducing cell cycle arrest and apoptotic death in CD30-expressing cells. BV may also mediate immunogenic cell death, bystander-killing effects, and antibody-dependent cellular phagocytosis (FIG. 2). Gardai S J, et al. *Cancer Res* 2015; 75(Suppl. 15):2469 [abstract]; Li F et al. *Cancer Res* 2016; 76:2710-2719; and Oflazoglu E, et al. *Blood* 2007; 110: 4370-4372.

In studies of patients with CD30+ relapsed, refractory DLBCL, CD30+ relapsed, refractory peripheral T-cell lymphoma (PTCL), and CD30+ cutaneous T-cell lymphoma (CTCL) treated with BV, ORR observed was 44%, 41%, and 73%, respectively. BV is approved in the United States as treatment for cHL after autologous stem cell transplant (ASCT) failure, or after failure of ≥2 prior chemotherapy regimens in non-ASCT candidates, and for systemic anaplastic large cell lymphoma after failure of ≥1 chemotherapy regimen. BV elicits its effect by inducing cell cycle arrest and apoptotic death in CD30-expressing cells, and can also mediate immunogenic cell death, bystander effects, and antibody-dependent cellular phagocytosis. As BV can mediate immunogenic cell death, it could synergize with PD-1 blockade. We hypothesize that nivolumab and BV can induce frequent and durable responses in patients with CD30+ relapsed, refractory T-cell NHL and diffuse large B-cell lymphoma (DLBCL).

Study Rationale

Patients with relapsed, refractory NHLs after progression following systemic therapy represent an area of substantial unmet medical need. BV can provide synergy with immune checkpoint inhibitors by inducing immunogenic cell death, which can upregulate the expression of the costimulatory molecule CD86 and MHC class II antigens on antigen-presenting cells in the tumor microenvironment. We hypothesize that the complementary mechanisms of actions of nivolumab in combination with BV could provide frequent and durable responses for patients with CD30+ relapsed, refractory NHL.

Study Design

Figure 3:
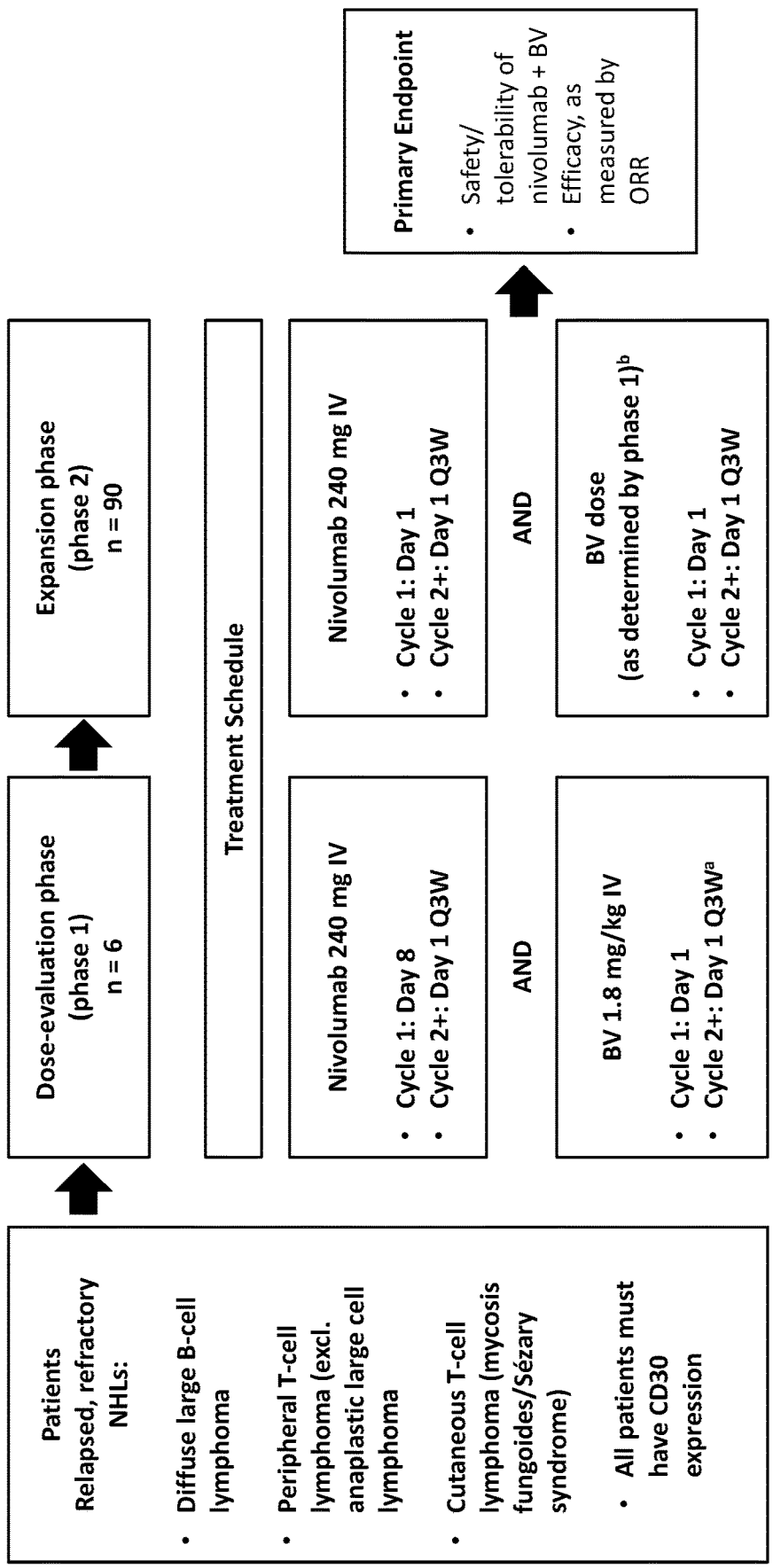
FIG. 3 shows the study design and treatment schedule for a Phase I/II clinical trial of brentuximab vedotin (BV) in combination with nivolumab.
Figure 4:
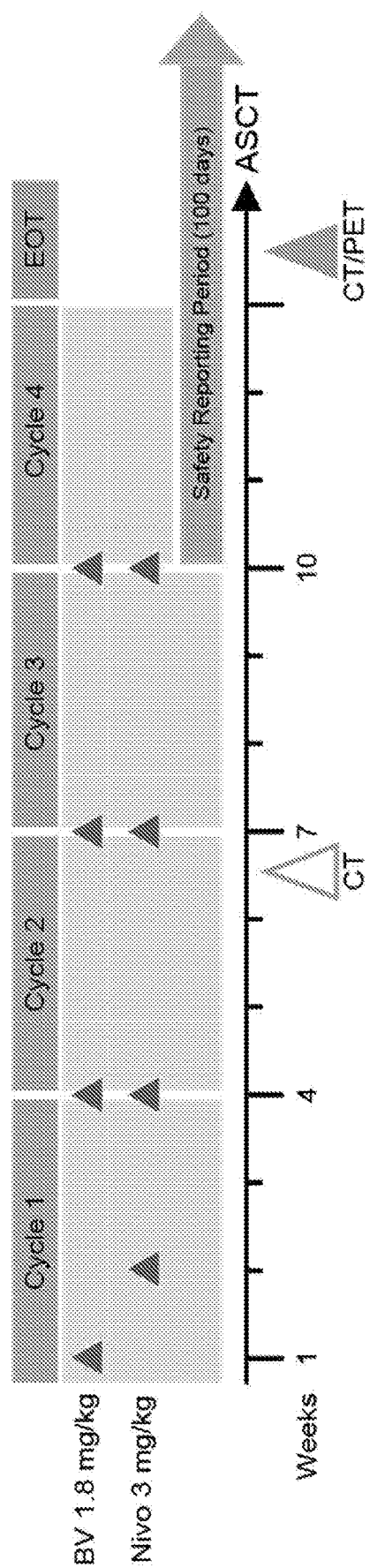
FIG. 4 shows the treatment schedule for a Phase I/II clinical trial of brentuximab vedotin (BV) in combination with nivolumab.

The design of the present single-arm, phase 1/2 multi-center study is shown in FIG. 3. Treatment continues in 3-week cycles until disease progression or unacceptable toxicity. Both nivolumab and BV are administered as 30-minute IV infusions. For cycles in which both treatments are given on the same day, the schedule is as follows: BV infusion, 30-minute rest, nivolumab infusion. Planned enrollment is for 96 patients: 6 in phase 1 and 90 in phase 2; recruitment will be equal across the 3 subtypes. Key inclusion and exclusion criteria are shown in Table 1.

TABLE 1

Key Inclusion/Exclusion Criteria

| Inclusion | Exclusion |
| --- | --- |
| Patients with relapsed, refractory NHLs, including DLBCL, PTCL, CTCL, PMBL, and MGZL | NHL involving the CNS |
| Expression of CD30 on ≥1% of tumor cells, confirmed via immunohistochemical analysis | History of progressive multifocal leukoencephalopathy |
| Age ≥ 15 years for patients with PMBL, ≥18 years for other histologies | Any active grade 3+ infection within 2 weeks prior to the first dose of BV |
| ECOG PS score of 0 or 1 | Pre-existing neuropathy of grade >2 |
| Tumor tissue (biopsy) for biomarker analysis | Prior BV exposure |
| Measurable disease according to 2014 Lugano Classification for patients with DLBCL, PTCL, PMBL, and MGZL | Prior exposure to immune checkpoint inhibitor |
| | Suspected or known autoimmune disease |

CNS = central nervous system;
ECOG PS = Eastern Cooperative Oncology Group Performance Status;
IHC = immunohistochemistry Objectives The primary objectives of the present study are two-fold. First, safety and tolerability of nivolumab in combination with BV will be evaluated in patients with relapsed, refractory NHLs. Second, the clinical benefit of nivolumab in combination with BV will be assessed in patients with relapsed, refractory NHLs, as measured by objective response rate (ORR; patients achieving a best overall response of either partial response or complete response).

The secondary objectives are to measure the duration of response, the complete response (CR) rate and duration of CR, and the progression free survival (PFS) and overall survival rate. In addition, exploratory objectives include (i) indeterminate response (IR) per Lymphoma Response to Immunomodulatory therapy Criteria (LYRIC); (ii) assessment of CD30 expression and PD-L1/2 status, and correlation with response, and (iii) identification of biomarkers of response or resistance to the BV and nivolumab combination regimen.

After the administration of BV and nivolumab, the patients will show improved overall response rates, increased overall survival, increased progression free survival, decreased tumor burden, decreased occurrence of drug-related adverse events or any combination thereof.

Example 2

A phase 1/2 study (NCT02572167) is ongoing to assess the safety profile and antitumor activity of BV administered in combination with nivolumab in patients with relapsed or refractory Hodgkin lymphoma (HL). Patients will be treated for up to four 21-day cycles with BV 1.8 mg/kg and nivolumab 3 mg/kg. Patients will be administered 1.8 mg/kg BV on Cycle 1 Day 1, and 3 mg/kg nivolumab on Cycle 1 Day 8. For cycles 2 through 4, BV and nivolumab will be administered on Day 1 of each cycle at the same doses, e.g., 1.8 mg/kg BV and 3 mg/kg nivolumab. Both BV and nivolumab will be administered by IV injection. After completion of the Cycle 4 response assessment (EOT), patients will be eligible to undergo ASCT. Responses were assessed using the 2014 Lugano classification (Cheson et al., J Clin Oncol 2014; 32(27):3059-68).

There will be two parts to this study. In Part 1, the safety of combination treatment will be evaluated by a Safety Monitoring Committee (SMC) prior to expansion of enrollment to evaluate treatment effect in Part 2. Part 2 of the study will further characterize safety and evaluate the antitumor activity of BV combined with nivolumab by enrolling patients at the recommended dose schedule determined in Part 1. Key inclusion and exclusion criteria are shown in Table 2. Patients were excluded if they previously received more than one line of anti-cancer therapy; BV or any immuno-oncology therapy affecting the PD-1, CTLA4, or CD137 pathways; and/or Allogeneic or autologous stem cell transplant (ASCT).

TABLE 2

Key Inclusion/Exclusion Criteria

| Inclusion | Exclusion |
|---|---|
| Relapsed or refractory Hodgkin lymphoma following failure of standard frontline chemotherapy for the treatment of classical Hodgkin lymphoma | Previously treated with BV, immune-oncology agents, or received an allogeneic or autologous stem cell transplant |
|  | Documented history of a cerebral vascular event |
| Eastern Cooperative Oncology Group (ECOG) performance status of 0 or 1 | History of another invasive malignancy that has not been in remission for at least 3 years |
| Age 18 years or older | History of progressive multifocal leukoencephalopathy (PML) |

The primary outcome measures of the present study are two-fold. First, safety and tolerability of nivolumab in combination with BV will be evaluated in patients with relapsed or refractory HL. Second, the clinical benefit of nivolumab in combination with BV will be assessed in patients with relapsed or refractory HL, as measured by complete response (CR) rate (CRR; patients achieving a best overall response of complete response) following the completion of study treatment, AE incidence, and severity.

The secondary outcome measures are to measure objective response rate (ORR), the duration of response, the duration of complete response (CR) and objective response, and the progression free survival (PFS) post-autologous stem cell transplant. In addition, exploratory objectives include assessment of CD30 expression and correlation with response and to identification of biomarkers of response or resistance to the BV and nivolumab combination regimen.

After the administration of BV and nivolumab, the patients will show improved overall response rates, increased overall survival, increased progression free survival, decreased tumor burden, decreased occurrence of drug-related adverse events or any combination thereof.

Results

Target enrollment of approximately 55 adult patients with classical Hodgkin lymphoma (cHL) that had relapsed or was refractory (RR) to frontline chemotherapy was met and patient information is provided below in Tables 3 and 4.

TABLE 3

Patient Characteristics

| Patient demographics and disease characteristics | N = 62 |
|---|---|
| Median age, years (range) | 36 (18-69) |
| Gender (M/F) | 30/32 |

TABLE 3-continued

Patient Characteristics

| Patient demographics and disease characteristics | N = 62 |
|---|---|
| Disease status relative to frontline tx, n (%) | |
| Primary refractory | 28 (45) |
| Relapsed, remission duration ≤ 1 year | 19 (31) |
| Bulky disease at baseline, n (%) | 8 (13) |
| Extranodal disease at baseline, n (%) | 16 (26) |
| Disease stage at initial diagnosis, n (%) | |
| I/II | 37 (60) |
| III/IV | 24 (39) |

TABLE 3-continued

Patient Characteristics

| Patient demographics and disease characteristics | N = 62 |
|---|---|
| Unknown | 1 (2) |
| Median prior therapies[a] (range) | 1 (1-3) |
| Prior chemotherapy regimens, n (%) | |
| ABVD | 56 (90) |
| BEACOPP | 2 (3) |
| Stanford V | 2 (3) |
| Other[b] | 6 (10) |
| Prior radiation | 9 (15) |

TABLE 4

Patient Disposition

| Patient disposition[c] | N = 62 n (%) |
|---|---|
| Received ≥ 1 dose of both study drugs, n (%) | 61 (98) |
| Remain on tx | 0 |
| Completed tx | 58 (94) |
| Reason for tx discontinuation[d] | |
| Patient decision | 2 (3) |
| Adverse event | 1 (2) |
| Investigator decision | 1 (2) |
| Received alternative salvage regimen | 12 (19) |
| ICE[e] | 9 (15) |
| GEMOX | 1 (2) |

TABLE 4-continued

Patient Disposition

| Patient disposition[c] | N = 62<br>n (%) |
|---|---|
| BeGEV | 1 (2) |
| Nivolumab | 1 (2) | a Includes radiation
b ABVD + AVD (3 pts), ABVE-PC (2 pts), R-ABVD (1 pt)
[c]1 pt discontinued before receiving study drug
[d]Pts who did not receive study drug still provided a reason for tx discontinuation
[e]2 of 9 pts who received ICE also received other regimens; 1 pt received 3 other salvage regimens: carboplatin/gemcitabine/decadron (not evaluable), followed by BV (PD), followed by gemcitabine/oxaliplatin (PD), and 1 pt had HL and FL and received bendamustine/rituximab Initially, twenty-five patients (60% female) with a median age of 32 years (range, 18-69) were enrolled to date. Sixty percent of patients have relapsed disease, 36% have primary refractory disease (failure to achieve complete response (CR) with frontline therapy, or relapse within 3 months of completing frontline therapy), and 1 patient (4%) has unknown status. At the time of enrollment, 32% of patients presented with extranodal disease and 16% with bulky disease.

Currently, sixty-two patients (52% female) with a median age of 36 years (range, 18-69) have been enrolled to date. Thirty-one percent of patients have relapsed disease, and forty-five percent of patients have primary refractory disease. At the time of enrollment, 26% of patients presented with extranodal disease and 13% with bulky disease.

At the time of the previous data extract, 23 patients had received treatment. An increased incidence of infusion-related reactions (IRRs) was observed at the start of combination treatment in Cycle 2 during the BV infusion leading to 1 dose delay. Premedication with corticosteroids (hydrocortisone 100 mg or equivalent) and antihistamines at Cycles 2-4 was instituted through a protocol amendment.

At the time of the previous data extract, six patients have completed combination treatment, and all have achieved an objective response rate (ORR, 100%), with 3 of 6 achieving a complete metabolic response (CmR, 50%). All 6 patients have proceeded directly to ASCT. The median number of CD34+ cells collected was 12.9×10^6 cells/kg (range, 5-26) in a mean number of 1.7 apheresis sessions (range, 1-2).

Figure 5B:
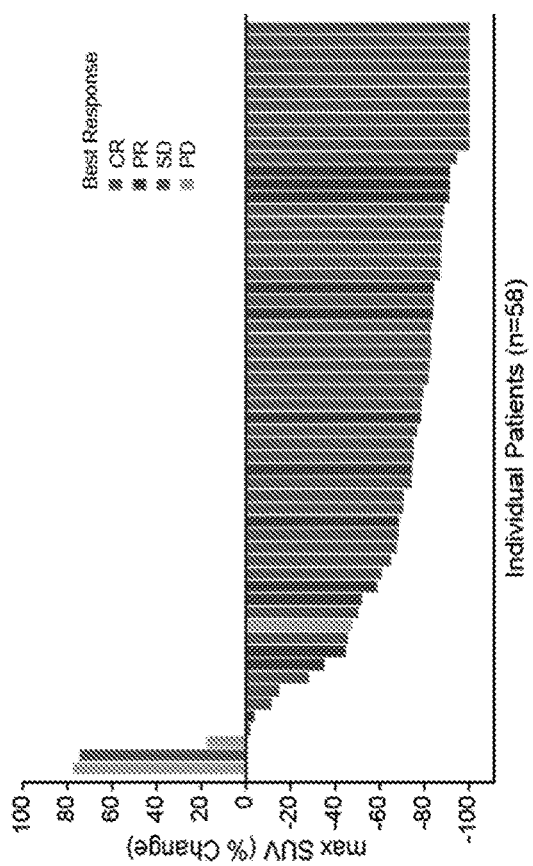
FIGS. 5A and 5B show the tumor response of patients treated with brentuximab vedotin (BV) in combination with nivolumab. CR means complete response; PR means partial response; SD means no metabolic response; and PD means progressive disease.
Figure 5A:
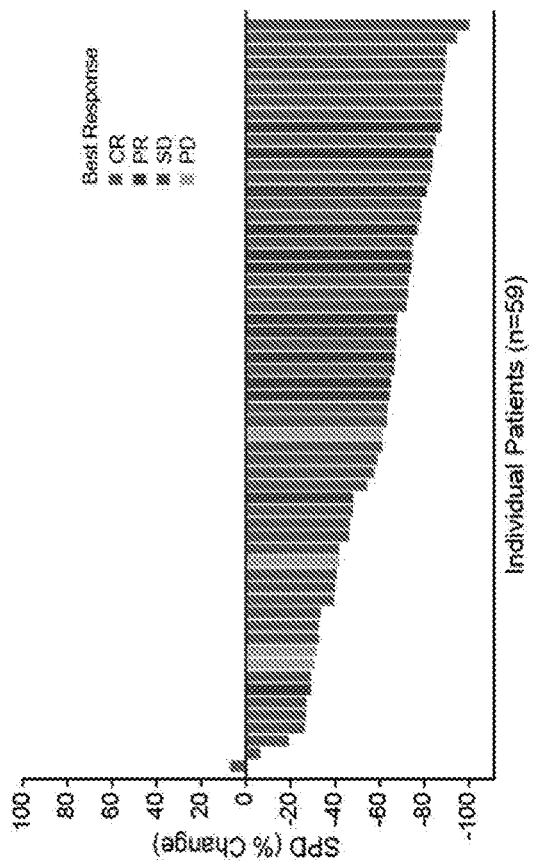

Currently, fifty-nine patients (95%) have completed combination treatment, with a high objective response rate (85%) with 63% complete responses (FIGS. 5A and 5B). Additional information about patient responses is provided in Table 5 below. Thirty-seven patients have proceeded to ASCT.

TABLE 5

| | N = 59<br>n (%) |
|---|---|
| Complete response (CR) | 37 (63) |
| Deauville ≤ 2 | 29 (49) |
| Deauville 3 | 7 (12) |
| Deauville 5[a] | 1 (2) |
| Partial response (PR) | 13 (22) |
| Deauville 4 | 7 (12) |
| Deauville 5 | 6 (10) |
| No metabolic response (SD) | 5 (8) |
| Deauville 5 | 5 (8) |
| Progressive disease (PD) | 3 (5) |

TABLE 5-continued

| | N = 59<br>n (%) |
|---|---|
| Deauville 5 | 2 (3) |
| Missing | 1 (2) |
| Clinical Progression (CP) | 1 (2) |

[a]1 patient had uptake in lymph node, but no evidence of disease was found on biopsy Priming of the immune system was indicated by an increase in pro-inflammatory cytokine and chemokine levels after BV dosing with high levels maintained following concurrent BV and nivolumab administration (FIGS. 6A-6D).

Additionally, an initial reduction in some T helper subsets (including Tregs) (FIG. 7A) and activated and proliferating CD4+ T cells (FIGS. 7B and 7C) after single agent BV administration, is followed by an expansion after combination dosing.

BV and nivolumab in combination were well tolerated in patients with relapsed refractory cHL. Potential immune-mediated AEs requiring steroids occurred in <10% of patients (FIG. 8). And although IRRs occurred relatively frequently (41% of patients), most frequently during the Cycle 2 BV infusion and required dose interruptions in 25% of patients, the maximum severity was Grade 3 which occurred in less than 5% of patients (FIG. 9).

Mandatory premedication with low-dose corticosteroids (hydrocortisone 100 mg or equivalent) and antihistamine at Cycles 2-4 was instituted. The rate of IRRs at Cycle 2 was equivalent before and after instituting premedication, i.e., 5 of 15 patients (33%) developed IRRs without premedication, whereas 15 of 45 patients (33%) developed IRRs with premedication. The rate of IRRs at Cycles 3-4 was low irrespective of premedication requirements.

Pre-ASCT treatment-emergent AEs occurred in 98% of patients at the following frequencies: Grade 1 (25%), Grade 2 (36%), Grade 3 (33%; anemia most frequent at 8%), and Grade 4 (5%). Treatment-related SAEs occurred in 5 patients (8%): pneumonitis and pyrexia each occurred in 2 patients; and colitis, malaise, nausea, pneumonia, respiratory failure, and sepsis each occurred in 1 patient. No unusual post-ASCT toxicities were reported.

Systemic steroids for potential immune-mediated AEs were required in 7% of patients. Each of the following was experience by 1 patient: Grade 4 pneumonitis and colitis (related to BV and nivolumab, 2 patients or 3%), Grade 2 pneumonitis (id.), Grade 3 diarrhea and Grade 2 colitis, and Grade 3 AST elevation.

Preliminary biomarker data indicate a BV-induced decrease in the percentage of CD4+ T regulatory ($T_{reg}$) cells at Cycle 1 Day 8, with no effect on proliferating CD8+ T cells. At Cycle 1, nivolumab induced a robust expansion of T cells one week after dosing (2 weeks after BV dosing), with no significant change observed in the percentage of CD4+ Th1 cells compared to baseline for most patients (5 of 6, 83%).

Early data suggest the combination of BV and nivolumab is an active and well-tolerated salvage therapy in patients with relapsed or refractory (R/R) Hodgkin lymphoma (HL). While an elevated incidence of IRRs has been observed, toxicities with this regimen appear to be tolerable overall. The preliminary antitumor activity suggests this combination can be a promising option for R/R HL patients.

The promising activity of the BV and nivolumab combination supports further exploration of this novel regimen for RR cHL patients.

Example 3

A randomized, open-label, Phase 3 trial of nivolumab plus brentuximab vedotin versus brentuximab vedotin alone in participants with relapsed refractory or ineligible for autologous stem cell transplant (ASCT) advanced stage classical Hodgkin Lymphoma is planned.

Background

The programmed death-1 (PD-1) cell surface membrane receptor is a member of the CD28 family of T-cell co-stimulatory receptors. PD-1 expression is a marker of T cell exhaustion and is associated with immune evasion in tumors. Hodgkin Lymphoma (HL) is characterized by genetic predisposition for over expression of programmed death (PD)-1 ligands. There are multiple mechanisms identified for upregulation of PD-L1 and PD-L2 in HL. Additionally CD30 is a cell membrane protein of the tumor necrosis factor family. CD30 is highly expressed in HL on the Reed Sternberg cells. Given the abundant expression of PD-1 ligands and CD30 in HL, the two proteins provide opportunity to target specific molecules associated with tumor growth and progression. Ongoing trials with the combination of brentuximab vedotin (BV) and nivolumab appear promising. Nivolumab and BV have demonstrated encouraging single agent activity in the treatment of relapsed HL. Since both drugs are effective as single agents, it is likely that the combination may have better efficacy as compared to either agent alone. A Phase 1/2 trial of the BV and nivolumab combination is ongoing in adults with Relapsed/Refractory Hodgkin Lymphoma after failure of first-line therapy. In this study, patients have been treated for a total of 4 cycles with combination regimen. Overall, the combination has been well tolerated with none of the participants requiring dose discontinuation due to toxicities. All patients were able to tolerate 4 cycles of combination regimen. The majority of adverse events including immune-related adverse events were low grades (1 and 2). Preliminary results are indicative of a highly efficacious regimen in a sample size n=20, with an Objective Overall Response Rate of 90% and Complete Metabolic Response of 62%. Similar findings have been observed in another ongoing trial. The preliminary data from the E4412 trial with a sample size (N=10) for relapsed/refractory patients has demonstrated an ORR of 100% and CR of 63%. Although the studies are ongoing and numbers are small, preliminary findings are suggestive of an effective and tolerable regimen in a refractory patient population with high unmet need.

It is therefore anticipated that combination therapy could potentially be more effective in the salvage treatment setting than administration of either agent alone. The combination may result in demonstrating higher clinical benefit, which can translate into improved disease control in a patient population where outcome is poor. Moreover, both agents are well tolerated, have few overlapping toxicities, and can be infused in the outpatient setting.

Study Population

Males and females, ages 18 and above with relapsed/refractory cHL and with one of the following:

a) Autologous Stem Cell Transplant (ASCT) ineligible patients

Chemo-resistant disease (unable to achieve CR or PR to salvage chemotherapy) or any significant coexisting medical condition (cardiac, renal, pulmonary, or hepatic dysfunction) are likely to have a negative impact on tolerability of ASCT. Note: Sponsor review and approval of participants<65 years of age who are not ASCT candidates is required before randomization. Participants must have received at least 2 prior chemotherapy regimens (BV can be included as one regimen).

b) Patients after failure of ASCT:

Documented absence of CR after 90 days from stem cell infusion for the most recent ASCT Documented relapsed disease (after CR) or disease progression (after PR or SD)

Both for a) and b), participants who are naïve to BV or who were sensitive to the most recent BV treatment are eligible. Participants must demonstrate BV sensitivity as defined by documented PR or CR from the most recent BV treatment, and by no disease progression during the most recent BV treatment or no early relapse within 3 months after last dose of the most recent BV based on medical record. For b), prior treatment with BV may have been as a single agent or in combination with chemotherapy and may have occurred during any line of therapy (e.g., induction, salvage, or consolidation post-ASCT). Of note, documentation of response following consolidation therapy with BV is not required, as it is assumed that the patients are in remission at the time of consolidation.

Other key inclusion criteria include ECOG PS 0-1 and biopsy confirmation of cHL prior to initiation of study drug. Key exclusion criteria include known CNS lymphoma, nodular lymphocyte-predominant HL, and active interstitial pneumonitis or CT evidence of Grade 1 pneumonitis.

Objectives and Endpoints

The primary and secondary objectives of the study, and the endpoints of the study, are set forth in Table 6 below. The primary objectives in the study will be measured by the primary endpoint of PFS assessed by BICR. The secondary objectives in the study will be measured by: (1) CRR, ORR, DOR, and DOCR assessed by BICR; (2) PFS assessed by investigator; and (3) OS.

TABLE 6

| Objectives/Endpoints | |
|---|---|
| Objectives | Endpoints |
| Primary | |
| To compare progression free survival of nivolumab + BV vs. BV based on BICR assessments | Progression Free Survival (PFS): defined as time from date of randomization to death, or disease progression. |
| Secondary | |
| To compare the complete response rate of nivolumab + BV vs. BV based on BICR assessments | Complete Response Rate (CRR): defined as proportion of participants who have achieved complete response |

TABLE 6-continued

Objectives/Endpoints

| Objectives | Endpoints |
| --- | --- |
| To assess objective response rate and duration of response based on BICR<br>To assess duration of complete response based on BICR<br>To assess overall survival of participants treated with nivolumab + BV vs BV<br>To assess PFS based on investigator assessments | (Lugano 2014 conference)<br>Objective Response Rate (ORR): defined as the proportion of participants who have achieved complete response or partial response (Lugano 2014 classification)<br>Duration of response or duration of complete response (DOR or DOCR): defined as the time from first response or complete response to the date of initial objectively documented progression as determined using the 2014 Lugano classification or death due to any cause<br>Overall Survival (OS): defined as the time between the date of randomization and the date of death.<br>PFS defined as the above but assessed by investigator. |

The primary endpoint PFS based on BICR assessment will be compared in two randomized arms via a two-sided, log-rank test stratified by the same factors used in randomization. Participants who die without a reported progression will be considered to have progressed on the date of their Overall Design This is a 1:1 randomized, open-label phase 3 study in advanced cHL participants 18 years old who are relapsed refractory or ineligible for autologous stem cell transplant (ASCT). Patients will be balanced in the 2 groups in regards to prior therapies. Approximately 340 participants will be treated in one of two arms: (1) nivolumab 360 mg IV every 3 weeks until progression or unacceptable toxicity (except for patients in CR who can discontinue at 2 years) plus BV 1.8 mg/kg IV every 3 weeks for 16 cycles, or until progression or unacceptable toxicity, whichever occurs first, or (2) BV alone 1.8 mg/kg every 3 weeks for 16 cycles, or until progression or unacceptable toxicity, whichever occurs first. Treatment may also be discontinued if the participant meets other criteria for discontinuation of study drug outlined in Section 8.1 of the protocol. Participants receiving nivolumab who achieve CR may discontinue treatment after a maximum of 2 years of therapy, provided that there is no prohibitive toxicity. Participants can be BV-naïve, or can have prior BV treatment as a single agent or in combination in any line of therapy. Randomization stratification will be performed on the following two factors: (1) Prior ASCT status (YES/NO); (2) Prior BV use (YES/NO). Participants will be balanced based on the stratification factors per arm.

Participants will undergo screening evaluations to determine eligibility within 28 days prior to first dose. Each 21-day dosing period will constitute a cycle.

Any participant who discontinues the study treatment prior to progression will be followed for progression, then survival, in the follow up phase of the study.

Approximately 400 participants will be screened and then, with an estimated screen failure rate of 15%, the planned sample size for this study will be approximately 340 randomized participants. The sample size of the study accounts for the primary efficacy endpoint, PFS. PFS will be evaluated for treatment effect at the overall alpha level of 0.05 (two-sided) with 90% power.

Sample size determination for PFS provides approximately 340 participants will be randomized to nivolumab+BV and BV arms in a 1:1 ratio, i.e., such that 170 participants will be assigned to the nivolumab+BV arm, and 170 participants will be assigned to the BV arm. For the comparison of PFS between the two treatment arms, the study requires at least 187 PFS events to ensure that a two-sided 5% type I error sequential test procedure will have 90% power to detect a hazard ratio (HR) of 0.62, corresponding to a median PFS of 15 vs 9.3 months for the nivolumab+BV and BV arms, respectively.

One formal PFS interim analysis will be conducted when at least 131 PFS events (70% of the final PFS events) have been observed and also requires a minimum follow-up of 9 months from Last Patient First Visit (LPFV).

Assuming an accrual rate of 10 participants enrolled per month, the accrual will take approximately 30.5 months. The final analysis for PFS is expected to take place 46 months after the first participant's randomization date (30.5 months of accrual+15.5 months of follow-up). This projection is based on an assumption that the progression free survival rates are 28% and 45.4% at 24 months in BV arm and nivolumab+BV arm, and very few events will occur after two years of treatment in both arms. The interim analysis for PFS is expected to take place 40 months after the first participant's randomization date.

East version 6.3 was used for sample size/power computations.

Figure 10:
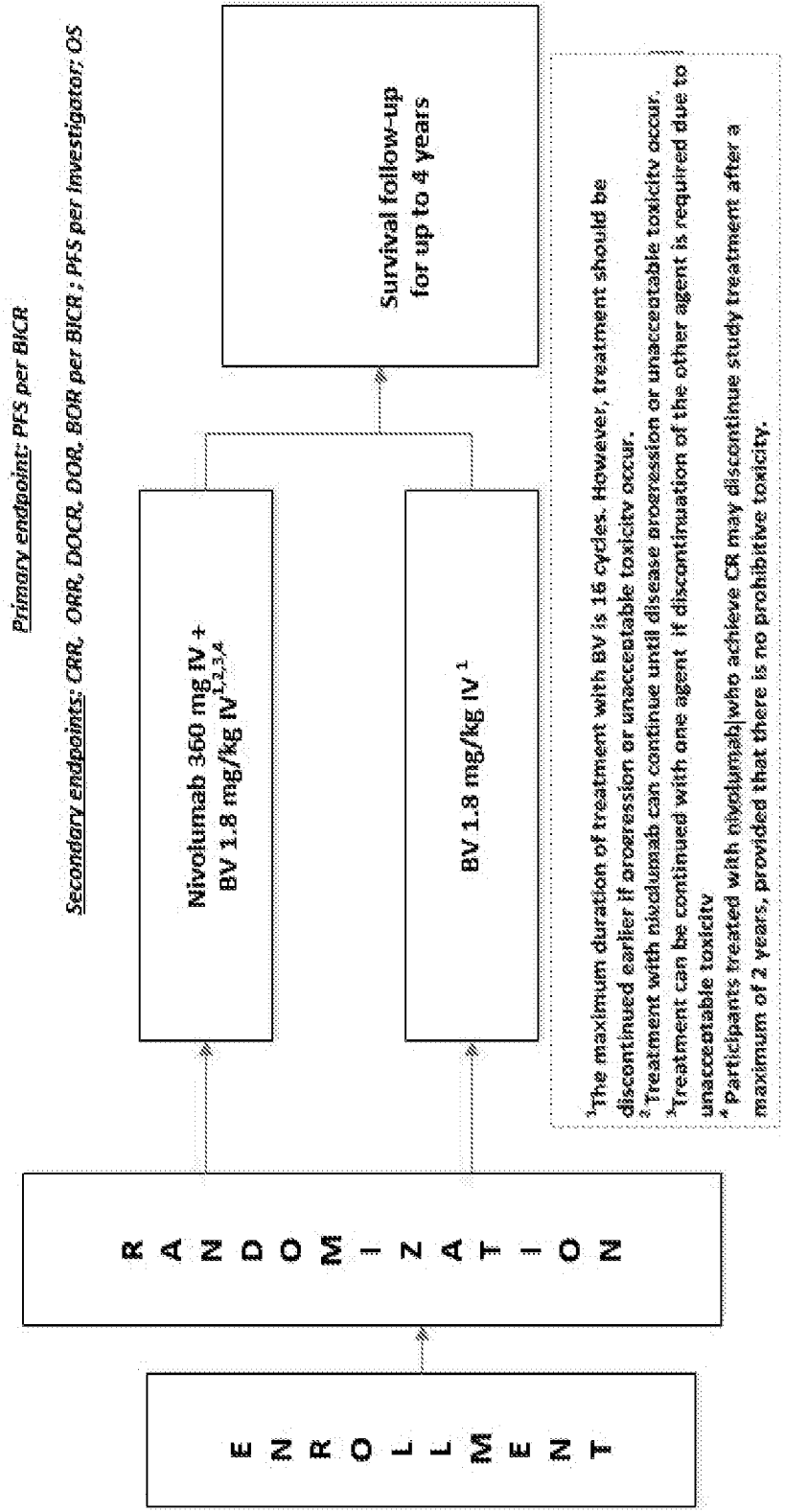
FIG. 10 shows the study design and treatment schedule for a Phase III clinical trial of brentuximab vedotin (BV) in combination with nivolumab.

The treatment arms and duration are shown in FIG. 10. The study treatment includes (1) a Randomized Investigational Arm: Nivolumab (360 mg flat dose) every 3 weeks until progression or unacceptable toxicity+BV (1.8 mg/kg) every 3 weeks for 16 cycles, progression, or unacceptable toxicity, whichever occurs first; and (2) a Randomized Control Arm: BV (1.8 mg/kg) every 3 weeks for 16 cycles, progression, or unacceptable toxicity, whichever occurs first. Further information about preparations and routes of administration for nivolumab and BV is provided in Table 7 below.

TABLE 7

| | Study Drug | |
|---|---|---|
| Medication | Potency | IP/Non-IP |
| Nivolumab (BMS-936558) Solution for Injection | 100 mg (10 mg/mL) and 40 mg (10 mg/mL) | IP |
| Brentuximab Vedotin Powder for Solution for Injection | 50 mg | IP |

Other medications used as support medication for preventative, diagnostic, or therapeutic reasons, as components of the standard of care for a given diagnosis, may be considered as non-investigational products.

Example 4

BV-Killed A20 Mouse Lymphoma Immunization Confers Anti-Tumor Protection

A20 mouse lymphoma cells were transfected with plasmid constructs encoding human TNFRSF8 (NM_001243.4) and sgRNA/Cas9 for control under the endogenous promoter of murine Tnfrsf8. Fluorescence activated cell sorting (FACS) yielded a clonal population of A20 cells that stably expressed human CD30, to be referenced as $A20^{hcD30}$, in order to be susceptible to brentuximab vedotin treatment.

$A20^{hcD30}$ cells were cultured in RPMI 1640 with 10% FBS, 10 mM HEPES, 1 mM sodium pyruvate, penicillin (100 U/ml), and streptomycin (100 μg/ml). $A20^{hcD30}$ cells were treated with 1 μg/ml BV or 100 nM mc-vc-MMAE for 4 days. In order to prepare dying cells for immunization, treated $A20^{hcD30}$ cells were overlaid atop Histopaque, and centrifuged at 2000 g for 30 minutes. Dead and dying cells were pelleted underneath the Histopaque layer, and viability was assessed to be <20% live cells by trypan blue exclusion. Flash-frozen $A20^{hcD30}$ cells were prepared by submerging cells in liquid nitrogen for 10 seconds, followed by immersion in 37° C. water until completely thawed. The liquid nitrogen freeze-thaw process was repeated 5 times. Dead and dying $A20^{hcD30}$ cells were resuspended in PBS and $2 \times 10^6$ cells were injected into the peritoneum of immune-competent Balb/c mice. 7 days later, mice received a second immunization with dead and dying cells prepared in the same manner.

Figure 11:
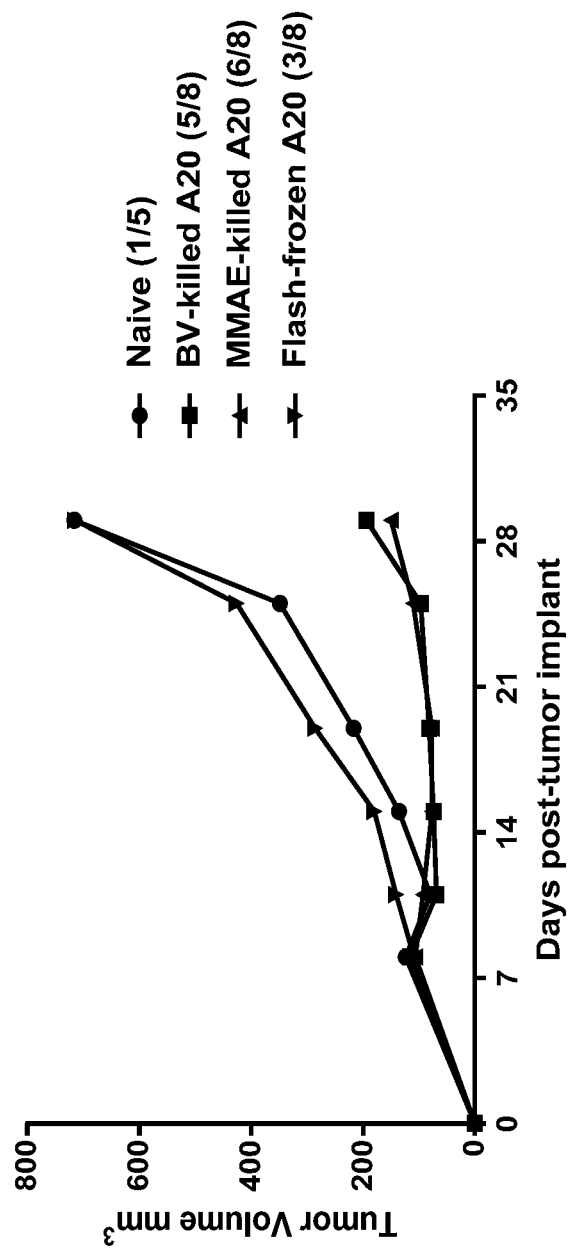
FIG. 11 shows BV-killed A20 mouse lymphoma immunization confers anti-tumor protection.

14 days after initial immunization, mice were subcutaneously implanted with $5 \times 10^6$ wild-type A20 cells and monitored for tumor growth. As shown in FIG. 11, mice that were immunized with BV-killed or mc-vc-MMAE-killed $A20^{hcD30}$ cells delayed tumor growth, and increased survival of tumor-bearing mice. As these effects occurred in the absence of any administered therapeutic, the presence of cells killed by BV or MMAE were sufficient to generate long-lasting protective immune memory against subsequent A20 lymphoma challenge.

T Cell Transfer Provides Protective Immunity

Immune-competent Balb/c mice were immunized with BV-killed or flash-frozen-killed $A20^{hcD30}$ cells as previously described. 16 weeks after initial immunization, spleens were harvested from immunized mice or naïve Balb/c mice, and manually homogenized. Splenic homogenates were combined from 4 mice per immunization, and CD3+ T cells were isolated using EasySep Mouse T cell Enrichment Kit (Stem Cell Technologies). $1 \times 10^6$ CD3+ T cells were administered intravenously into A20 tumor-bearing mice.

Figure 12B:
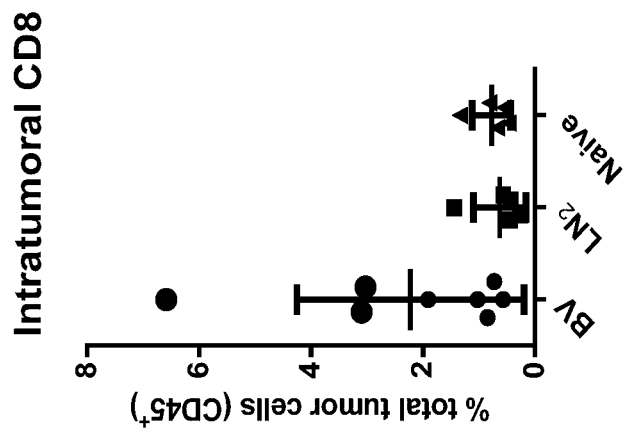
FIGS. 12A and 12B show T cell transfer from mice immunized with BV-killed cells provides protective immunity.
Figure 12A:
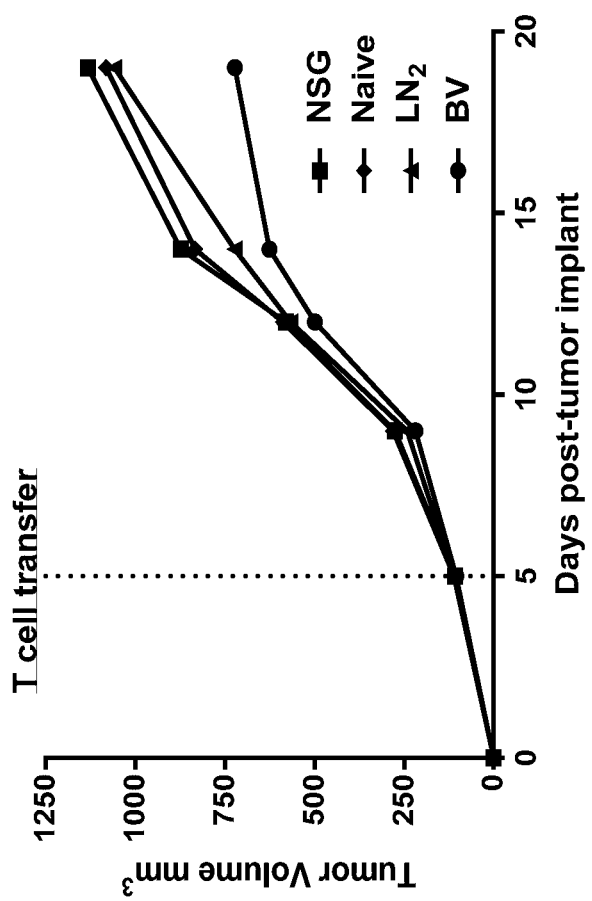

$4 \times 10^6$ wild-type A20 cells were subcutaneously implanted into immunodeficient NOD/SCID/γ-chain-deficient (NSG) mice. 5 days after implant, mice harboring tumors~100 mm³ were randomized, and received $1 \times 10^6$ T cells from mice as described above. As shown in FIG. 12A, NSG mice that received T cells from mice immunized with BV-killed cells slowed tumor growth, as well as increased CD8 T cells within the tumor (FIG. 12B). The capacity of T cells to provide robust anti-tumor immunity long after immunization demonstrates that tumor death from BV elicits strong immune memory that is mediated by T cells.

PD-1 Inhibition Potentiates Protective Immunity Conferred by BV

Figure 13:
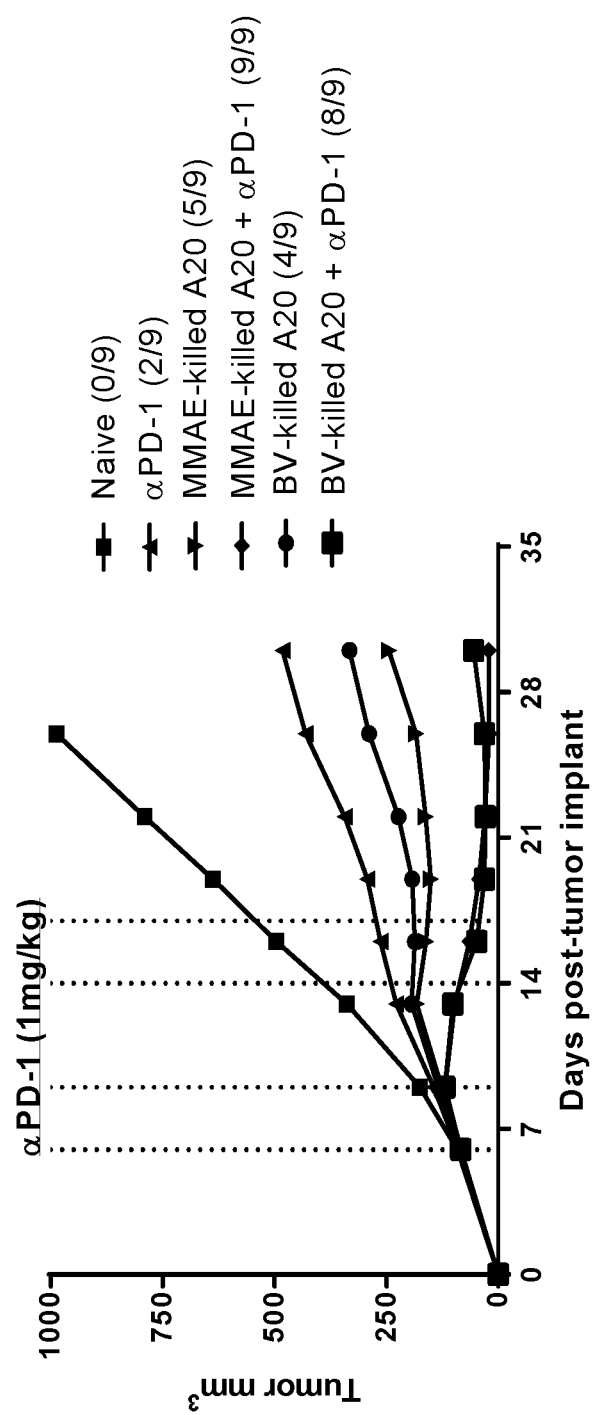
FIG. 13 shows improved tumor clearance and survival associated with BV and nivolumab combination therapy.

Balb/c mice were immunized with BV- or MMAE-killed $A20^{hcD30}$ cells as described above. 14 days after initial immunization, mice were subcutaneously implanted with $5 \times 10^6$ wild-type A20 cells. Anti-murine PD-1 (1 mg/kg, BioLegend) was administered intravenously on days 6, 9, 14, and 17 after A20 tumor challenge. Immunization with BV- or MMAE-killed $A20^{hcD30}$ cells conferred protective anti-tumor immunity. As shown in FIG. 13, combination with anti-PD-1 therapy augmented protective immunity and improved tumor clearance and survival.

T Cell and NK Cell Infiltration into Autologous Tumors in a Humanized Mouse Model.

Figure 14A:
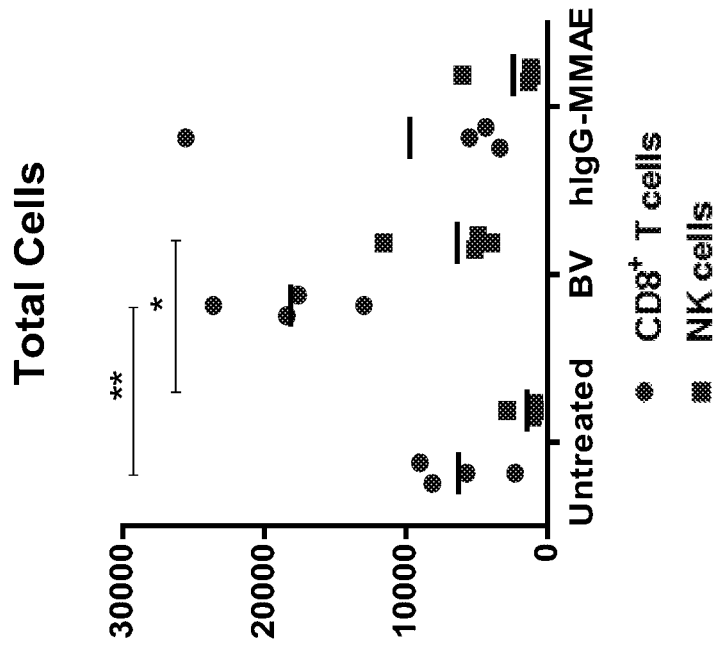
Figure 14B:
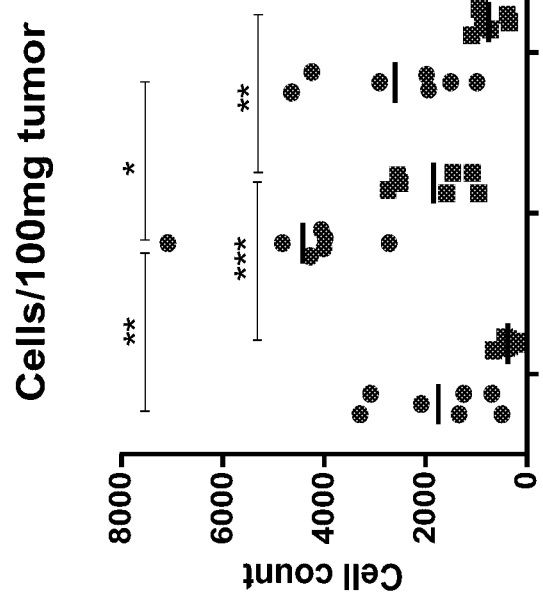

Epstein Barr virus (EBV) transformed lymphoblastoid cell Lines (LCL) were implanted subcutaneously into NSG mice. When LCL tumor volumes reached 250 mm³, mice received a single suboptimal dose of BV or control hIgG-MMAE (1 mg/kg, i.p). Three days following dosing, $2.0 \times 10^6$ autologous peripheral blood mononuclear cells (PBMC) were adoptively transferred to mice via tail vein injection. Eleven days following transfer of PBMC, tumors were harvested, weighed, and manually dissociated through a 70 μm cell strainer. Following centrifugation, individual tumor cell pellets were resuspended in 4 ml of RPMI+10% FCS, and 200 ul of the cell suspension was used for staining and analysis by flow cytometry (FACS). Tumor cell suspensions were stained with Zombie Aqua Viability Dye (Biolegend) followed by staining with fluorescently labeled antibodies targeting human CD19, CD2, CD8, CD4, CD56, human CD45, PD-L1, PD-1, and murine CD45.1 (1:50 dilution, Biolegend) in staining buffer (SB: PBS, 2% FCS, 1% NRS, 0.05% $NaN_3$) at 4° C. for 30 minutes. Cells were washed and resuspended in 120 μl of SB for plate-based FACS using an Attune NXT flow cytometer. All events were collected from 80 μl of sample, and FACS-measured cell concentrations were used to calculate numbers of infiltrating immune cells. CD8+ T cells were identified as viability dye$^{neg}$, hCD45+, mCD45.1-, CD2+, CD8+ cells. NK cells were identified as viability dye$^{neg}$, hCD45+, mCD45.1-, CD2+, CD56+ cells. FIG. 14A shows calculated cell counts relative to tumor mass, or alternatively, as a calculated total cell count (FIG. 14B). FIG. 14C shows CD8+ T cells recovered from tumors expressed increased levels of PD-1, and LCL tumor cells expressed heightened levels of PD-L1 relative to their resting/normal PBMC counterparts (FIG. 14D). Treatment of mice harboring established LCL tumors with a suboptimal dose of BV enhanced intratumoral accumulation of human cytotoxic cells consistent with the induction of an anti-tumor inflammatory response.

BV Enhances Immune-Mediated Tumor Clearance Alone and in Combination with Nivolumab in the Humanized LCL Tumor Model.

Figure 15A:
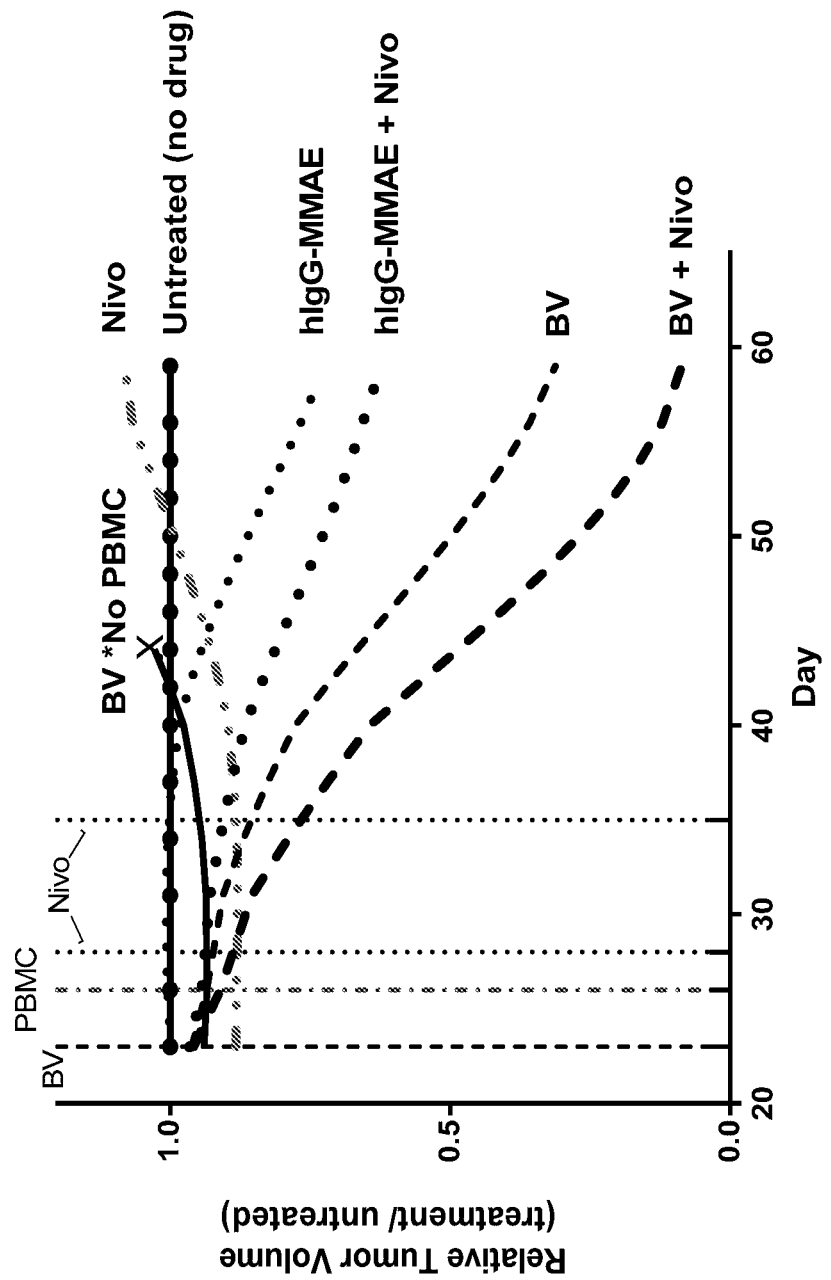

Epstein Barr virus (EBV) transformed lymphoblastoid cell lines (LCL) were implanted subcutaneously into NSG mice. When LCL tumors averaged 250 mm³, mice received a single suboptimal dose of BV or control hIgG-MMAE (1 mg/kg, i.p). Three days following dosing, $2 \times 10^6$ autologous PBMC were adoptively transferred to mice via tail vein injection. Mice received two doses of nivolumab (10 mg/kg, i.p.) 2 and 7 days after adoptive transfer of PBMC. FIG. 15A shows treatment group tumor volume over time, relative to untreated (no drug) control. Notably, mice receiving a suboptimal dose of BV without the addition of PBMC (solid line, top) did not reject tumors and were removed from the study when tumors exceeded 2000 mm$^3$. All other treatment groups received autologous PBMC and showed tumor regression, highlighting the role of immune-mediated tumor clearance in this model. A single, suboptimal dose of BV administered 3 days prior to transfer of PBMC resulted in enhanced immune-mediated tumor clearance compared to mice receiving control hIgG-MMAE or nivolumab alone. Importantly, mice receiving a combination of BV and nivolumab showed the most rapid tumor clearance of any treatment group. The significance of these differences is reflected in a comparison of mean tumor volumes at day 50, during active tumor clearance (FIG. 15B). Taken together, results obtained from this humanized model support the conclusion that in addition to direct tumor cell killing, BV drives an inflammatory response that enhances immune-mediated cellular cytotoxicity and pairs well with nivolumab.

What is claimed is:

1. A method of treating a human subject afflicted with a Hodgkin lymphoma, comprising:
   (a) administering to the human subject about 3 mg/kg of an antibody or an antigen-binding portion thereof that binds specifically to a Programmed Death-1 receptor (PD-1) and inhibits PD-1 activity (anti-PD-1 antibody) once every three weeks; and
   (b) administering to the human subject about 1.8 mg/kg of brentuximab vedotin once every three weeks;
   wherein (i) brentuximab vedotin is administered to the human subject on day 1 of a first 21-day cycle; and
   (ii) the anti-PD-1 antibody is administered to the human subject on day 8 of the first 21-day cycle;
   wherein a combination of brentuximab vedotin and the anti-PD-1 antibody is administered on day 1 of each of a second 21-day cycle, a third 21-day cycle; and a fourth 21-day cycle, wherein the second 21-day cycle, the third 21-day cycle, and the fourth 21-day cycle follow in succession after the first 21-day cycle; and
   wherein the Hodgkin lymphoma comprises one or more cells that express CD30.

2. The method of claim 1, wherein the Hodgkin lymphoma is classical Hodgkin lymphoma (cHL).

3. The method of claim 1, wherein at least about 0.1% of the Hodgkin lymphoma cells express CD30.

4. The method of claim 1, wherein at least about 5% of the Hodgkin lymphoma cells express CD30.

5. The method of claim 1, wherein the anti-PD-1 antibody comprises nivolumab.

6. The method of claim 1, wherein the Hodgkin lymphoma comprises one or more cells that express PD-L1, PD-L2, or both PD-L1 and PD-L2.

7. The method of claim 1, wherein the human subject exhibits progression-free survival of at least about one month after the initial administration of the anti-PD-1 antibody and/or brentuximab vedotin.

8. The method of claim 1, wherein the Hodgkin lymphoma is relapsed Hodgkin lymphoma or refractory Hodgkin lymphoma.

9. The method of claim 8, wherein the relapsed Hodgkin lymphoma is relapsed Hodgkin lymphoma after autologous stem cell transplant (ASCT) or relapsed Hodgkin lymphoma in a human subject ineligible for ASCT.

10. The method of claim 1, wherein the anti-PD-1 antibody comprises pembrolizumab.

* * * * *